US010792356B2

(12) United States Patent
Moore et al.

(10) Patent No.: US 10,792,356 B2
(45) Date of Patent: Oct. 6, 2020

(54) RECOMBINANT RSV WITH SILENT MUTATIONS, VACCINES, AND METHODS RELATED THERETO

(71) Applicants: Emory University, Atlanta, GA (US); Children's Healthcare of Atlanta, Inc., Atlanta, GA (US)

(72) Inventors: Martin L. Moore, Decatur, GA (US); Jia Meng, Atlanta, GA (US); Anne Hotard, Atlanta, GA (US); Elizabeth Littauer, Decatur, GA (US); Christopher C. Stobart, Decatur, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 16/263,915

(22) Filed: Jan. 31, 2019

(65) Prior Publication Data

US 2019/0224306 A1 Jul. 25, 2019

Related U.S. Application Data

(62) Division of application No. 14/775,671, filed as application No. PCT/US2014/027447 on Mar. 14, 2014, now Pat. No. 10,232,032.

(60) Provisional application No. 61/890,500, filed on Oct. 14, 2013, provisional application No. 61/781,228, filed on Mar. 14, 2013.

(51) Int. Cl.

| | |
|---|---|
| ***A61K 39/155*** | (2006.01) |
| ***C12N 7/00*** | (2006.01) |
| ***C07K 14/005*** | (2006.01) |
| ***A61K 39/12*** | (2006.01) |
| ***A61K 45/06*** | (2006.01) |
| *A61K 39/00* | (2006.01) |

(52) U.S. Cl.

CPC ............ *A61K 39/155* (2013.01); *A61K 39/12* (2013.01); *A61K 45/06* (2013.01); *C07K 14/005* (2013.01); *C12N 7/00* (2013.01); *A61K 2039/5254* (2013.01); *A61K 2039/55* (2013.01); *A61K 2039/58* (2013.01); *C12N 2760/18522* (2013.01); *C12N 2760/18534* (2013.01); *C12N 2760/18562* (2013.01); *C12N 2800/22* (2013.01)

(58) Field of Classification Search

None

See application file for complete search history.

(56) References Cited

U.S. PATENT DOCUMENTS

| | | | |
|---|---|---|---|
| 5,618,682 | A | 4/1997 | Scheirer |
| 5,674,713 | A | 10/1997 | Mcelroy et al. |
| 5,922,326 | A | 7/1999 | Murphy et al. |
| 5,976,796 | A | 11/1999 | Szalay et al. |
| 5,993,824 | A | 11/1999 | Murphy et al. |
| 6,033,886 | A | 3/2000 | Conzelmann |
| 6,074,859 | A | 6/2000 | Hirokawa et al. |
| 6,214,805 | B1 | 4/2001 | Torrence et al. |
| 6,264,957 | B1 | 7/2001 | Collins |
| 6,689,367 | B1 | 2/2004 | Collins et al. |
| 6,699,476 | B1 | 3/2004 | Collins et al. |
| 6,713,066 | B1 | 3/2004 | Collins et al. |
| 6,790,449 | B2 | 9/2004 | Collins |
| 6,923,971 | B2 | 8/2005 | Krempl et al. |
| 7,465,574 | B2 | 12/2008 | Jin et al. |
| 7,485,440 | B2 | 2/2009 | Collins et al. |
| 7,572,904 | B2 | 8/2009 | Cheng et al. |
| 7,744,902 | B2 | 6/2010 | Krempl et al. |
| 7,846,455 | B2 | 12/2010 | Collins et al. |
| 8,163,530 | B2 | 4/2012 | Cheng et al. |
| 8,772,256 | B2 | 7/2014 | Graham |
| 8,846,051 | B2 | 9/2014 | Kew et al. |
| 9,011,876 | B2 | 4/2015 | Yagodich et al. |

(Continued)

FOREIGN PATENT DOCUMENTS

| | | |
|---|---|---|
| WO | 2006042156 | 4/2006 |
| WO | 2008121992 | 10/2008 |

(Continued)

OTHER PUBLICATIONS

Boyapalle, et al. Respiratory Syncytial Virus NS1 Protein Colocalizes with Mitochondrial Antiviral Signaling Protein Mavs following Infection. PLoS ONE 7(2): e29386. doi:10.1371/journal.pone.0029386 (Year: 2012).*

(Continued)

*Primary Examiner* — Shanon A. Foley

*Assistant Examiner* — Myron G Hill

(74) *Attorney, Agent, or Firm* — Meunier Carlin & Curfman LLC

(57) ABSTRACT

In certain embodiments, the disclosure relates to the polynucleotide sequences of respiratory syncytial virus (RSV). In certain embodiments, the disclosure relates to isolated or recombinant nucleic acids and polypeptides comprising desirable nucleic acid sequences and mutations disclosed herein. In certain embodiments, isolated or recombinant RSV comprising the nucleic acids and polypeptides disclosed herein (e.g., attenuated recombinant RSV) are also provided, as are immunogenic compositions including such nucleic acids, polypeptides, and RSV genomes that are suitable for use as vaccines. Attenuated or killed RSV containing these nucleic acids and mutation in the form of copied nucleic acids (e.g., cDNAs) are also contemplated.

14 Claims, 16 Drawing Sheets

Specification includes a Sequence Listing.

(56) References Cited

U.S. PATENT DOCUMENTS

| | | | |
|---|---|---|---|
| 9,107,939 | B2 | 8/2015 | Luytjes et al. |
| 9,476,032 | B2 | 10/2016 | Wimmer et al. |
| 9,492,525 | B2 | 11/2016 | Fattom et al. |
| 9,624,375 | B2 | 4/2017 | Wonneberger et al. |
| 2008/0118530 | A1 | 5/2008 | Kew et al. |
| 2012/0264217 | A1 | 10/2012 | Moore et al. |
| 2014/0271699 | A1 | 9/2014 | Kwong et al. |
| 2014/0356390 | A1 | 12/2014 | Kew et al. |
| 2015/0368622 | A1 | 12/2015 | Collins et al. |

FOREIGN PATENT DOCUMENTS

| | | | |
|---|---|---|---|
| WO | 2010053883 | A1 | 3/2010 |
| WO | 2012158613 | A1 | 11/2012 |
| WO | 2014124238 | A1 | 8/2014 |
| WO | 2014152534 | | 9/2014 |
| WO | 2014160463 | A1 | 10/2014 |

OTHER PUBLICATIONS

International Search Report in PCT Application No. PCT/US2014/027447 dated Aug. 4, 2014 (7 pages).

EMBL: U39661, Respiratory syncytial virus, complete genome. [online] Mar. 29, 1997.

NCBI, GenBank Accession No. ACO83297.1.

NCBI, GenBank Accession No.

Moore et al. (2009) J. Virology 80(9): 4185-4194.

Coleman et al. (2008) Science 320(5884): 1784-1787.

Spann et al. (2005) J. Virology 79(9): 5353-5362.

Buchholz et al. (2009) J. Virology 83(4): 1969-1980.

European Search Report in Application No. 14770291.4 dated Jan. 23, 2017 (10 pages).

First Office Action issued by the Japanese Patent Office, in Application No. 22016-502442, dated Jun. 5, 2018 (6 pages) English Translation.

Title: US-14-775-671-SEQ 4 Alignment versus 08-962-690-SEQ12, 17 pages, dated Sep. 28, 2017.

First Examination Report issued by the Australian Patent Office, in Application No. 2014239583, dated Jun. 18, 2019.

Office Action issued by the Chinese Patent Office, in Application No. 201480025415.2, dated Jun. 27, 2019.

International Search Report and Written Opinion issued for Application No. PCT/US2016/058976, dated Apr. 6, 2017, 11 pages.

International Preliminary Report on Patentability issued for Application No. PCT/US2016/058976, dated May 11, 2018.

Extended European Search Report issued for Application No. 16860742.2, dated May 7, 2019.

Burns, Cara Carthel, et al. "Modulation of poliovirus replicative fitness in HeLa cells by deoptimization of synonymous codon usage in the capsid region." Journal of virology 80.7 (2006): 3259-3272.

Clements, Mary Lou, et al. "Evaluation of bovine, cold-adapted human, and wild- type human parainfluenza type 3 viruses in adult volunteers and in chimpanzees." Journal of clinical microbiology 29.6 (1991): 1175-1182.

Collins, Peter L., and José A. Melero. "Progress in understanding and controlling respiratory syncytial virus: still crazy after all these years." Virus research 162.1-2 (2011): 80-99.

Collins, Peter L., et al. "Gene overlap and site-specific attenuation of transcription of the viral polymerase L gene of human respiratory syncytial virus." Proceedings of the National Academy of Sciences 84.15 (1987): 5134-5138.

Collins, Peter L., et al. "Nucleotide sequences for the gene junctions of human respiratory syncytial virus reveal distinctive features of intergenic structure and gene order." Proceedings of the National Academy of Sciences 83.13 (1986): 4594-4598.

Collins, Peter L., et al. "Production of infectious human respiratory syncytial virus from cloned cDNA confirms an essential role for the transcription elongation factor from the 5'proximal open reading frame of the M2 mRNA in gene expression and provides a capability for vaccine development." Proceedings of the National Academy of Sciences 92.25 (1995): 11563-11567.

DeWet, J. R., et al. "Subramani (1987)." Firefly luciferase gene: structure and expression in mammalian cells. Mol. Cell. Biol 7.725-737.

Glenn, Gregory M., et al. "A randomized, blinded, controlled, dose-ranging study of a respiratory syncytial virus recombinant fusion (F) nanoparticle vaccine in healthy women of childbearing age." The Journal of infectious diseases 213.3 (2015): 411-422.

Hotard et al. A stabilized respiratory syncytial virus reverse genetics system amenable to recombination-mediated mutagenesis. Virology 434, 129-136 (2012).

Hotard et al. Identification of residues in the human respiratory syncytial virus fusion protein that modulate fusion activity and pathogenesis. J Virol 89, 512-522 (2015).

Hotard, Anne L., et al. "Functional analysis of the 60-nucleotide duplication in the respiratory syncytial virus Buenos Aires strain attachment glycoprotein." Journal of virology 89.16 (2015): 8258-8266.

Iyer, Vidyashankara, et al. "Impact of formulation and particle size on stability and immunogenicity of oil-in-water emulsion adjuvants." Human vaccines & immunotherapeutics 11.7 (2015): 1853-1864.

Johnson, Philip R., et al. "The G glycoprotein of human respiratory syncytial viruses of subgroups A and B: extensive sequence divergence between antigenically related proteins." Proceedings of the National Academy of Sciences 84.16 (1987): 5625-5629.

Karron, R. A., et al. "A gene deletion that up-regulates viral gene expression yields an attenuated RSV vaccine with improved antibody responses in children. Sci Transl Med 7: 312ra175." (2015).

Karron, Ruth A., et al. "Identification of a recombinant live attenuated respiratory syncytial virus vaccine candidate that is highly attenuated in infants." The Journal of infectious diseases 191.7 (2005): 1093-1104.

Kim, Hyun Wha, et al. "Respiratory syncytial virus disease in infants despite prior administration of antigenic inactivated vaccine." American journal of epidemiology 89.4 (1969): 422-434.

Kim, Hyun Wha, et al. "Safety and antigenicity of temperature sensitive (TS) mutant respiratory syncytial virus (RSV) in infants and children." Pediatrics 52.1 (1973): 56-63.

Lemon, Ken, et al. "Recombinant subgroup B human respiratory syncytial virus expressing enhanced green fluorescent protein efficiently replicates in primary human cells and is virulent in cotton rats." Journal of virology 89.5 (2015): 2849-2856.

Maniatis, Tom, Stephen Goodbourn, and Janice A. Fischer. "Regulation of inducible and tissue-specific gene expression." Science 236.4806 (1987): 1237-1245.

Meng et al. Respiratory Syncytial Virus Attachment Glycoprotein Contribution to Infection Depends on the Specific Fusion Protein. Journal of virology 90, 245-253 (2015).

Meng, Jia, et al. "Refining the balance of attenuation and immunogenicity of respiratory syncytial virus by targeted codon deoptimization of virulence genes." MBio 5.5 (2014): e01704-14.

Merzlyak, Ekaterina M., et al. "Bright monomeric red fluorescent protein with an extended fluorescence lifetime." Nature methods 4.7 (2007): 555.

Mueller, Steffen, et al. "Reduction of the rate of poliovirus protein synthesis through large-scale codon deoptimization causes attenuation of viral virulence by lowering specific infectivity." Journal of virology 80.19 (2006): 9687-9696.

Murphy, Brian R., et al. "Enhanced pulmonary histopathology is observed in cotton rats immunized with formalin-inactivated respiratory syncytial virus (RSV) or purified F glycoprotein and challenged with RSV 3-6 months after immunization." Vaccine 8.5 (1990): 497-502.

NCBI, GenBank Accession No. AC083297.1, Apr. 20, 2009.

NCBI, GenBank Accession No. U50362.1, Jun. 30, 2004.

Needleman, Saul B., and Christian D. Wunsch. "A general method applicable to the search for similarities in the amino acid sequence of two proteins." Journal of molecular biology 48.3 (1970): 443-453.

(56) References Cited

OTHER PUBLICATIONS

Pearson, William R., and David J. Lipman. "Improved tools for biological sequence comparison." Proceedings of the National Academy of Sciences 85.8 (1988): 2444-2448.
Quan, Fu-Shi, et al. "Viruslike particle vaccine induces protection against respiratory syncytial virus infection in mice." Journal of Infectious Diseases 204.7 (2011): 987-995.
Randhawa, J. S., et al. "Nucleotide sequences of the genes encoding the putative attachment glycoprotein (G) of mouse and tissue culture-passaged strains of pneumonia virus of mice." Virology 207.1 (1995): 240-245.
Rostad, Christina A., et al. "A recombinant respiratory syncytial virus vaccine candidate attenuated by a low-fusion F protein is immunogenic and protective against challenge in cotton rats." Journal of virology 90.16 (2016): 7508-7518.
Shcherbo, Dmitry, et al. "Far-red fluorescent tags for protein imaging in living tissues." Biochemical journal 418.3 (2009): 567-574.
Smith, Temple F., and Michael S. Waterman. "Comparison of biosequences." Advances in applied mathematics 2.4 (1981): 482-489.
Stobart, Christopher C., et al. "Reverse Genetics of Respiratory Syncytial Virus." Human Respiratory Syncytial Virus. Humana Press, New York, NY, 2016. 141-153.
Voss, Stephan D., Uwe Schlokat, and Peter Gruss. "The role of enhancers in the regulation of cell-type-specific transcriptional control." Trends in Biochemical Sciences 11.7 (1986): 287-289.
Walsh, Edward E., et al. "Immunization with glycoprotein subunits of respiratory syncytial virus to protect cotton rats against viral infection." Journal of Infectious Diseases 155.6 (1987): 1198-1204.
Wright, Peter F., et al. "Administration of a highly attenuated, live respiratory syncytial virus vaccine to adults and children." Infection and Immunity37.1 (1982): 397-400.
Wright, Peter F., et al. "Evaluation of a live, attenuated respiratory syncytial virus vaccine in infants." The Journal of pediatrics 88.6 (1976): 931-936.
Office Action issued in Canadian Application No. 2,906,606, dated Jan. 27, 2020.
Written Opinion for Singaporean Application No. 11201803581V, dated Sep. 10, 2019.
Search Report for Singaporean Application No. 11201803581V, dated Sep. 10, 2019.
English Summary Office Action for Chinese Application No. 2014800254152, dated Oct. 8, 2019.
Office Action issued in U.S. Appl. No. 15/772,275, dated Mar. 19, 2020.

* cited by examiner

| AA | Codon | Human Brain Genes | A2 | 2-20 | Line19 | 3-2 | 3-4 | 12-21 |
|---|---|---|---|---|---|---|---|---|
| Ala | GCT | | | | | | | |
| | GCC | | | | | | | |
| | GCA | | | | | | | |
| | GCG | | | | | | | |
| Cys | TGT | | | | | | | |
| | TGC | | | | | | | |
| Asp | GAT | | | | | | | |
| | GAC | | | | | | | |
| Glu | GAA | | | | | | | |
| | GAG | | | | | | | |
| Phe | TTT | | | | | | | |
| | TTC | | | | | | | |
| Gly | GGT | | | | | | | |
| | GGC | | | | | | | |
| | GGA | | | | | | | |
| | GGG | | | | | | | |
| His | CAT | | | | | | | |
| | CAC | | | | | | | |
| Ile | ATT | | | | | | | |
| | ATC | | | | | | | |
| | ATA | | | | | | | |
| Lys | AAA | | | | | | | |
| | AAG | | | | | | | |
| Leu | TTA | | | | | | | |
| | TTG | | | | | | | |
| | CTT | | | | | | | |
| | CTC | | | | | | | |
| | CTA | | | | | | | |
| | CTG | | | | | | | |
| Asn | AAT | | | | | | | |
| | AAC | | | | | | | |

| AA | Codon | Human Brain Genes | A2 | 2-20 | Line19 | 3-2 | 3-4 | 12-21 |
|---|---|---|---|---|---|---|---|---|
| Pro | CCT | | | | | | | |
| | CCC | | | | | | | |
| | CCA | | | | | | | |
| | CCG | | | | | | | |
| Gln | CAA | | | | | | | |
| | CAG | | | | | | | |
| Arg | CGT | | | | | | | |
| | CGC | | | | | | | |
| | CGA | | | | | | | |
| | CGG | | | | | | | |
| | AGA | | | | | | | |
| | AGG | | | | | | | |
| Ser | TCT | | | | | | | |
| | TCC | | | | | | | |
| | TCA | | | | | | | |
| | TCG | | | | | | | |
| | AGT | | | | | | | |
| | AGC | | | | | | | |
| Thr | ACT | | | | | | | |
| | ACC | | | | | | | |
| | ACA | | | | | | | |
| | ACG | | | | | | | |
| Val | GTT | | | | | | | |
| | GTC | | | | | | | |
| | GTA | | | | | | | |
| | GTG | | | | | | | |
| Tyr | TAT | | | | | | | |
| | TAC | | | | | | | |

FIG. 1

Day 1 Day 3 Day 5 Day 7 Day 7 kRSV-A2

Mock kRSV-dNSh

FIG. 3

| Score | Expect | Method | Identities | Positives | Gaps |
|---|---|---|---|---|---|
| 1169 bits(3023) | 0.0 | Compositional matrix adjust. | 573/574(99%) | 574/574(100%) | 0/574(0%) |

```
Query  1     MELPILKANAITTILAAVTFCFASSQNITEEFYQSTCSAVSKGYLSALRTGWYTSVITIE
60           MELPILKANAITTILAAVTFCFASSQNITEEFYQSTCSAVSKGYLSALRTGWYTSVITIE
Sbjct  1     MELPILKANAITTILAAVTFCFASSQNITEEFYQSTCSAVSKGYLSALRTGWYTSVITIE
60

Query  61    LSNIKKNKCNGTDAKVKLMKQELDKYKNAVTELQLLMQSTPAANNRARRELPRFMNYTLN
120          LSNIKKNKCNGTDAKVKLMKQELDKYKNAVTELQLLMQSTPAANNRARRELPRFMNYTLN
Sbjct  61    LSNIKKNKCNGTDAKVKLMKQELDKYKNAVTELQLLMQSTPAANNRARRELPRFMNYTLN
120

Query  121   NTKKTNVTLSKKRKRRFLGFLLGVGSAIASGIAVSKVLHLEGEVNKIKSALLSTNKAVVS
180          NTKKTNVTLSKKRKRRFLGFLLGVGSAIASGIAVSKVLHLEGEVNKIKSALLSTNKAVVS
Sbjct  121   NTKKTNVTLSKKRKRRFLGFLLGVGSAIASGIAVSKVLHLEGEVNKIKSALLSTNKAVVS
180

Query  181   LSNGVSVLTSRVLDLKNYIDKQLLPIVNKQSCRISNIETVIEFQQKNNRLLEITREFSVN
240           LSNGVSVLTSRVLDLKNYIDKQLLPIVNKQSCRISNIETVIEFQQKNNRLLEITREFSVN
Sbjct  181   LSNGVSVLTSRVLDLKNYIDKQLLPIVNKQSCRISNIETVIEFQQKNNRLLEITREFSVN
240

Query  241   AGVTTPVSTYMLTNSELLSLINDMPITNDQKKLMSNNVQIVRQQSYSIMSIIKEEVLAYV
300          AGVTTPVSTYMLTNSELLSLINDMPITNDQKKLMSNNVQIVRQQSYSIMSIIKEEVLAYV
Sbjct  241   AGVTTPVSTYMLTNSELLSLINDMPITNDQKKLMSNNVQIVRQQSYSIMSIIKEEVLAYV
300

Query  301   VQLPLYGVIDTPCWKLHTSPLCTTNTKEGSNICLTRTDRGWYCDNAGSVSFFPQAEKCKV
360          VQLPLYGVIDTPCWKLHTSPLCTTNTKEGSNICLTRTDRGWYCDNAGSVSFFPQAEKCKV
Sbjct  301   VQLPLYGVIDTPCWKLHTSPLCTTNTKEGSNICLTRTDRGWYCDNAGSVSFFPQAEKCKV
360

Query  361   QSNRVFCDTMYSLTLPSEVNLCNVDIFNPKYDCKIMTSKTDVSSSVITSLGAIVSCYGKT
420          QSNRVFCDTMYSLTLPSEVNLCNVDIFNPKYDCKIMTSKTDVSSSVITSLGAIVSCYGKT
Sbjct  361   QSNRVFCDTMYSLTLPSEVNLCNVDIFNPKYDCKIMTSKTDVSSSVITSLGAIVSCYGKT
420

Query  421   KCTASNKNRGIIKTFSNGCDYVSNKGVDTVSVGNTLYYVNKQEGKSLYVKGEPIINFYDP
480         KCTASNKNRGIIKTFSNGCDYVSNKGVDTVSVGNTLYYVNKQEGKSLYVKGEPIINFYDP
Sbjct  421   KCTASNKNRGIIKTFSNGCDYVSNKGVDTVSVGNTLYYVNKQEGKSLYVKGEPIINFYDP
480

Query  481   LVFPSDEFDASISQVNEKINQSLAFIRKSDELLHNVNAGKSTTNIMITTIIIVIIVILLS
540          LVFPSDEFDASISQVNEKINQSLAFIRKSDELLHNVNAGKSTTNIMITTIIIVIIVILLS
Sbjct  481   LVFPSDEFDASISQVNEKINQSLAFIRKSDELLHNVNAGKSTTNIMITTIIIVIIVILLS
540

Query  541   LIAVGLLLYCKARSTPVTLSKDQLSGINNIAFSN   574
             LIAVGLLLYCKARSTP+TLSKDQLSGINNIAFSN
Sbjct  541   LIAVGLLLYCKARSTPITLSKDQLSGINNIAFSN   574
```

FIG. 9

| Score | Expect | Method | Identities | Positives | Gaps |
|---|---|---|---|---|---|
| 1160 bits(3001) | 0.0 | Compositional matrix adjust. | 570/574(99%) | 572/574(99%) | 0/574(0%) |

```
Query  1    MELPILKANAITTILAAVTFCFASSQNITEEFYQSTCSAVSKGYLSALRTGWYTSVITIE
60          MELPILKANAITTILAAVTFCFASSQNITEEFYQSTCSAVSKGYLSALRTGWYTSVITIE
Sbjct  1    MELPILKANAITTILAAVTFCFASSQNITEEFYQSTCSAVSKGYLSALRTGWYTSVITIE
60

Query  61   LSNIKKNKCNGTDAKVKLMKQELDKYKNAVTELQLLMQSTPAANNRARRELPRFMNYTLN
120         LSNIK+NKCNGTDAKVKLMKQELDKYKNAVTELQLLMQSTPAANNRARRELPRFMNYTLN
Sbjct  61   LSNIKENKCNGTDAKVKLMKQELDKYKNAVTELQLLMQSTPAANNRARRELPRFMNYTLN
120

Query  121  NTKKTNVTLSKKRKRRFLGFLLGVGSAIASGIAVSKVLHLEGEVNKIKSALLSTNKAVVS
180         NTKKTNVTLSKKRKRRFLGFLLGVGSAIASGIAVSKVLHLEGEVNKIKSALLSTNKAVVS
Sbjct  121  NTKKTNVTLSKKRKRRFLGFLLGVGSAIASGIAVSKVLHLEGEVNKIKSALLSTNKAVVS
180

Query  181  LSNGVSVLTSRVLDLKNYIDKQLLPIVNKQSCRISNIETVIEFQQKNNRLLEITREFSVN
240         LSNGVSVLTS+VLDLKNYIDKQLLPIVNKQSCRISNIETVIEFQQKNNRLLEITREFSVN
Sbjct  181  LSNGVSVLTSKVLDLKNYIDKQLLPIVNKQSCRISNIETVIEFQQKNNRLLEITREFSVN
240

Query  241  AGVTTPVSTYMLTNSELLSLINDMPITNDQKKLMSNNVQIVRQQSYSIMSIIKEEVLAYV
300         AGVTTPVSTYMLTNSELLSLINDMPITNDQKKLMSNNVQIVRQQSYSIMSIIKEEVLAYV
Sbjct  241  AGVTTPVSTYMLTNSELLSLINDMPITNDQKKLMSNNVQIVRQQSYSIMSIIKEEVLAYV
300

Query  301  VQLPLYGVIDTPCWKLHTSPLCTTNTKEGSNICLTRTDRGWYCDNAGSVSFFPQAEKCKV
360         VQLPLYGVIDTPCWKLHTSPLCTTNTKEGSNICLTRTDRGWYCDNAGSVSFFPQAE CKV
Sbjct  301  VQLPLYGVIDTPCWKLHTSPLCTTNTKEGSNICLTRTDRGWYCDNAGSVSFFPQAETCKV
360

Query  361  QSNRVFCDTMYSLTLPSEVNLCNVDIFNPKYDCKIMTSKTDVSSSVITSLGAIVSCYGKT
420         QSNRVFCDTM SLTLPSEVNLCNVDIFNPKYDCKIMTSKTDVSSSVITSLGAIVSCYGKT
Sbjct  361  QSNRVFCDTMNSLTLPSEVNLCNVDIFNPKYDCKIMTSKTDVSSSVITSLGAIVSCYGKT
420

Query  421  KCTASNKNRGIIKTFSNGCDYVSNKGVDTVSVGNTLYYVNKQEGKSLYVKGEPIINFYDP
480         KCTASNKNRGIIKTFSNGCDYVSNKGVDTVSVGNTLYYVNKQEGKSLYVKGEPIINFYDP
Sbjct  421  KCTASNKNRGIIKTFSNGCDYVSNKGVDTVSVGNTLYYVNKQEGKSLYVKGEPIINFYDP
480

Query  481  LVFPSDEFDASISQVNEKINQSLAFIRKSDELLHNVNAGKSTTNIMITTIIIVIIVILLS
540         LVFPSDEFDASISQVNEKINQSLAFIRKSDELLHNVNAGKSTTNIMITTIIIVIIVILLS
Sbjct  481  LVFPSDEFDASISQVNEKINQSLAFIRKSDELLHNVNAGKSTTNIMITTIIIVIIVILLS
540

Query  541  LIAVGLLLYCKARSTPVTLSKDQLSGINNIAFSN  574
            LIAVGLLLYCKARSTPVTLSKDQLSGINNIAFSN
Sbjct  541  LIAVGLLLYCKARSTPVTLSKDQLSGINNIAFSN  574
```

FIG. 10

| Score | Expect | Method | Identities | Positives | Gaps |
|---|---|---|---|---|---|
| 1160 bits(3002) | 0.0 | Compositional matrix adjust. | 569/574(99%) | | 0/574(0%) |

```
Query  1    MELPILKANAITTILAAVTFCFASSQNITEEFYQSTCSAVSKGYLSALRTGWYTSVITIE
60          MELPILKANAITTILAAVTFCFASSQNITEEFYQSTCSAVSKGYLSALRTGWYTSVITIE
Sbjct  1    MELPILKANAITTILAAVTFCFASSQNITEEFYQSTCSAVSKGYLSALRTGWYTSVITIE
60

Query  61   LSNIKKNKCNGTDAKVKLMKQELDKYKNAVTELQLLMQSTPAANNRARRELPRFMNYTLN
120         LSNIK+NKCNGTDAKVKLMKQELDKYKNAVTELQLLMQSTPAANNRARRELPRFMNYTLN
Sbjct  61   LSNIKENKCNGTDAKVKLMKQELDKYKNAVTELQLLMQSTPAANNRARRELPRFMNYTLN
120

Query  121  NTKKTNVTLSKKRKRRFLGFLLGVGSAIASGIAVSKVLHLEGEVNKIKSALLSTNKAVVS
180         NTKKTNVTLSKKRKRRFLGFLLGVGSAIASGIAVSKVLHLEGEVNKIKSALLSTNKAVVS
Sbjct  121  NTKKTNVTLSKKRKRRFLGFLLGVGSAIASGIAVSKVLHLEGEVNKIKSALLSTNKAVVS
180

Query  181  LSNGVSVLTSRVLDLKNYIDKQLLPIVNKQSCRISNIETVIEFQQKNNRLLEITREFSVN
240         LSNGVSVLTS+VLDLKNYIDKQLLPIVNKQSCRISNIETVIEFQQKNNRLLEITREFSVN
Sbjct  181  LSNGVSVLTSKVLDLKNYIDKQLLPIVNKQSCRISNIETVIEFQQKNNRLLEITREFSVN
240

Query  241  AGVTTPVSTYMLTNSELLSLINDMPITNDQKKLMSNNVQIVRQQSYSIMSIIKEEVLAYV
300          GVTTPVSTYMLTNSELLSLINDMPITNDQKKLMSNNVQIVRQQSYSIMSIIKEEVLAYV
Sbjct  241  VGVTTPVSTYMLTNSELLSLINDMPITNDQKKLMSNNVQIVRQQSYSIMSIIKEEVLAYV
300

Query  301  VQLPLYGVIDTPCWKLHTSPLCTTNTKEGSNICLTRTDRGWYCDNAGSVSFFPQAEKCKV
360         VQLPLYGVIDTPCWKLHTSPLCTTNTKEGSNICLTRTDRGWYCDNAGSVSFFPQAE CKV
Sbjct  301  VQLPLYGVIDTPCWKLHTSPLCTTNTKEGSNICLTRTDRGWYCDNAGSVSFFPQAETCKV
360

Query  361  QSNRVFCDTMYSLTLPSEVNLCNVDIFNPKYDCKIMTSKTDVSSSVITSLGAIVSCYGKT
420         QSNRVFCDTM SLTLPSEVNLCNVDIFNPKYDCKIMTSKTDVSSSVITSLGAIVSCYGKT
Sbjct  361  QSNRVFCDTMNSLTLPSEVNLCNVDIFNPKYDCKIMTSKTDVSSSVITSLGAIVSCYGKT
420

Query  421  KCTASNKNRGIIKTFSNGCDYVSNKGVDTVSVGNTLYYVNKQEGKSLYVKGEPIINFYDP
480         KCTASNKNRGIIKTFSNGCDYVSNKGVDTVSVGNTLYYVNKQEGKSLYVKGEPIINFYDP
Sbjct  421  KCTASNKNRGIIKTFSNGCDYVSNKGVDTVSVGNTLYYVNKQEGKSLYVKGEPIINFYDP
480

Query  481  LVFPSDEFDASISQVNEKINQSLAFIRKSDELLHNVNAGKSTTNIMITTIIIVIIVILLS
540         LVFPSDEFDASISQVNEKINQSLAFIRKSDELLHNVNAGKSTTNIMITTIIIVIIVILLS
Sbjct  481  LVFPSDEFDASISQVNEKINQSLAFIRKSDELLHNVNAGKSTTNIMITTIIIVIIVILLS
540

Query  541  LIAVGLLLYCKARSTPVTLSKDQLSGINNIAFSN  574
            LIAVGLLLYCKARSTPVTLSKDQLSGINNIAFSN
Sbjct  541  LIAVGLLLYCKARSTPVTLSKDQLSGINNIAFSN  574
```

FIG. 11

A
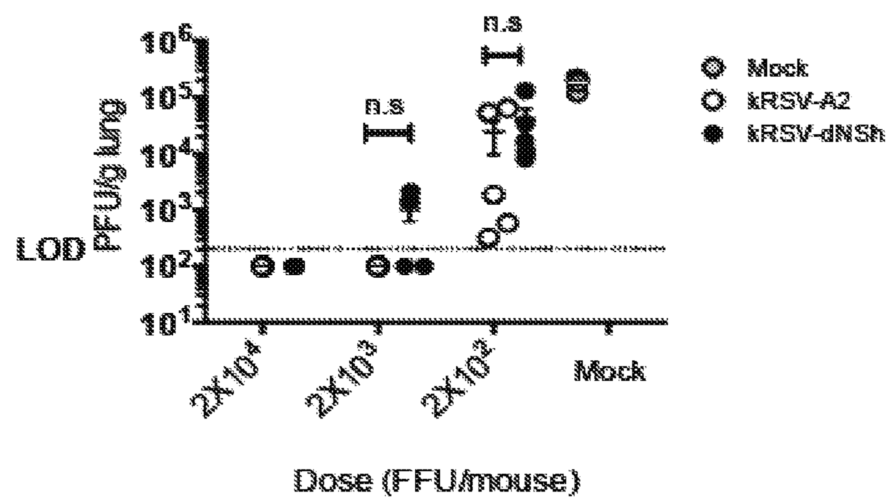
B
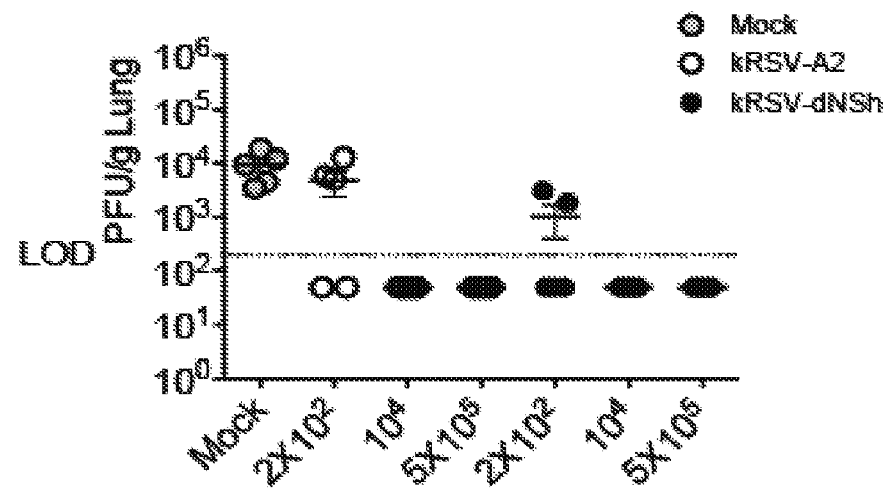
FIG. 13

SEQUENCE LISTING

<160> NUMBER OF SEQ ID NOS: 21

<210> SEQ ID NO 1
<211> LENGTH: 15573
<212> TYPE: DNA
<213> ORGANISM: respiratory syncytial virus

<400> SEQUENCE: 1
acgcgaaaaa atgcgtacaa caaacttgca taaaccaaaa aaatggggca aataagaatt 60
tgataagtac cacttaaatt taactccctt gcttagcgat ggtgagcgag ctgattaagg 120
agaacatgca catgaagctg tacatggagg gcaccgtgaa caaccaccac ttcaagtgca 180
catccgaggg cgaaggcaag ccctacgagg gcacccagac catgagaatc aaggcggtcg 240
agggcggccc tctccccttc gccttcgaca tcctggctac cagcttcatg tacggcagca 300
aaaccttcat caaccacacc cagggcatcc ccgacttctt taagcagtcc ttccccgagg 360
gcttcacatg ggagagagtc accacatacg aagacggggg cgtgctgacc gctacccagg 420
acaccagcct ccaggacggc tgcctcatct acaacgtcaa gatcagaggg gtgaacttcc 480
catccaacgg ccctgtgatg cagaagaaaa cactcggctg ggaggcctcc accgagaccc 540
tgtaccccgc tgacggcggc ctggaaggca gagccgacat ggccctgaag ctcgtgggcg 600
ggggccacct gatctgcaac ttgaagacca catacagatc caagaaaccc gctaagaacc 660
tcaagatgcc cggcgtctac tatgtggaca gaagactgga aagaatcaag gaggccgaca 720
aagagaccta cgtcgagcag cacgaggtgg ctgtggccag atactgcgac ctccctagca 780
aactggggca cagatgagta ttcaattata gttattaaaa acttaacaga agacaaaaat 840
ggggcaaata agaatttgat aagtaccact taaatttaac tcccttgctt agcgatgggt 900
tcgaattcgc tatcgatgat aaaagtacgt ctacaaaatc tatttgataa tgatgaagta 960
gcgctactaa aaataacgtg ttatacggat aaactaatac atctaacgaa tgcgctagcg 1020
aaagcggtaa tacatacgat aaaactaaat ggtatagtat ttgtacatgt aataacgtcg 1080
tcggatatat gtccgaataa taatatagta gtaaaatcga attttacgac gatgccggta 1140
ctacaaaatg gtggttatat atgggaaatg atggaactaa cgcattgttc gcaaccgaat 1200
ggtctactag atgataattg tgaaataaaa ttttcgaaaa aactatcgga ttcgacgatg 1260
acgaattata tgaatcaact atcggaacta ctaggttttg atctaaatcc gtaaattata 1320
attaatatca actagcaaat caatgtcact aacaccatta gttaatataa aacttaacag 1380
aagacaaaaa tggggcaaat aaatcaattc agccaaccca accatggata cgacgcataa 1440
tgataatacg ccgcaacgtc taatgataac ggatatgcgt ccgctatcgc tagaaacgat 1500
aataacgtcg ctaacgcgtg atataataac gcataaattt atatatctaa taaatcatga 1560
atgtatagta cgtaaactag atgaacgtca agcgacgttt acgtttctag taaattatga 1620
aatgaaacta ctacataaag taggttcgac gaaatataaa aaatatacgg aatataatac 1680
gaaatatggt acgtttccga tgccgatatt tataaatcat gatggttttc tagaatgtat 1740
aggtataaaa ccgacgaaac atacgccgat aatatataaa tatgatctaa atccgtaaat 1800
ttcaacacaa tattcacaca atctaaaaca acaactctat gcataactat actccatagt 1860

-continued ccagatggag cctgaaaatt atagtaattt aaaattaagg agagatataa gatagaagat 1920
ggggcaaata caaagatggc tcttagcaaa gtcaagttga atgatacact caacaaagat 1980
caacttctgt catccagcaa atacaccatc caacggagca caggagatag tattgatact 2040
cctaattatg atgtgcagaa acacatcaat aagttatgtg gcatgttatt aatcacagaa 2100
gatgctaatc ataaattcac tgggttaata ggtatgttat atgcgatgtc taggttagga 2160
agagaagaca ccataaaaat actcagagat gcgggatatc atgtaaaagc aaatggagta 2220
gatgtaacaa cacatcgtca agacattaat ggaaaagaaa tgaaatttga agtgttaaca 2280
ttggcaagct taacaactga aattcaaatc aacattgaga tagaatctag aaaatcctac 2340
aaaaaaatgc taaaagaaat gggagaggta gctccagaat acaggcatga ctctcctgat 2400
tgtgggatga taatattatg tatagcagca ttagtaataa ctaaattagc agcaggggac 2460
agatctggtc ttacagccgt gattaggaga gctaataatg tcctaaaaaa tgaaatgaaa 2520
cgttacaaag gcttactacc caaggacata gccaacagct tctatgaagt gtttgaaaaa 2580
catccccact ttatagatgt ttttgttcat tttggtatag cacaatcttc taccagaggt 2640
ggcagtagag ttgaagggat ttttgcagga ttgtttatga atgcctatgg tgcagggcaa 2700
gtgatgttac ggtggggagt cttagcaaaa tcagttaaaa atattatgtt aggacatgct 2760
agtgtgcaag cagaaatgga acaagttgtt gaggtttatg aatatgccca aaaattgggt 2820
ggtgaagcag gattctacca tatattgaac aacccaaaag catcattatt atctttgact 2880
caatttcctc acttctccag tgtagtatta ggcaatgctg ctggcctagg cataatggga 2940
gagtacagag gtacaccgag gaatcaagat ctatatgatg cagcaaaggc atatgctgaa 3000
caactcaaag aaaatggtgt gattaactac agtgtactag acttgacagc agaagaacta 3060
gaggctatca aacatcagct taatccaaaa gataatgatg tagagctttg agttaataaa 3120
aaatggggca aataaatcat catggaaaag tttgctcctg aattccatgg agaagatgca 3180
aacaacaggg ctactaaatt cctagaatca ataaagggca aattcacatc acccaaagat 3240
cccaagaaaa aagatagtat catatctgtc aactcaatag atatagaagt aaccaaagaa 3300
agccctataa catcaaattc aactattatc aacccaacaa atgagacaga tgatactgca 3360
gggaacaagc ccaattatca aagaaaacct ctagtaagtt tcaaagaaga ccctacacca 3420
agtgataatc ccttttctaa actatacaaa gaaaccatag aaacatttga taacaatgaa 3480
gaagaatcca gctattcata cgaagaaata aatgatcaga caaacgataa tataacagca 3540
agattagata ggattgatga aaaattaagt gaaatactag gaatgcttca cacattagta 3600
gtggcaagtg caggacctac atctgctcgg gatggtataa gagatgccat gattggttta 3660
agagaagaaa tgatagaaaa aatcagaact gaagcattaa tgaccaatga cagattagaa 3720
gctatggcaa gactcaggaa tgaggaaagt gaaaagatgg caaaagacac atcagatgaa 3780
gtgtctctca atccaacatc agagaaattg aacaacctat tggaagggaa tgatagtgac 3840
aatgatctat cacttgaaga tttctgatta gttaccactc ttcacatcaa cacacaatac 3900
caacagaaga ccaacaaact aaccaaccca atcatccaac caaacatcca tccgccaatc 3960
agccaaacag ccaacaaaac aaccagccaa tccaaaacta accacccgga aaaaatctat 4020
aatatagtta caaaaaaagg aaagggtggg gcaaatatgg aaacatacgt gaacaagctt 4080
cacgaaggct ccacatacac agctgctgtt caatacaatg tcttagaaaa agacgatgac 4140
cctgcatcac ttacaatatg ggtgcccatg ttccaatcat ctatgccagc agatttactt 4200

```
ataaaagaac tagctaatgt caacatacta gtgaaacaaa tatccacacc caagggacct   4260
tcactaagag tcatgataaa ctcaagaagt gcagtgctag cacaaatgcc cagcaaattt   4320
accatatgcg ctaatgtgtc cttggatgaa agaagcaaac tagcatatga tgtaaccaca   4380
ccctgtgaaa tcaaggcatg tagtctaaca tgcctaaaat caaaaaatat gttgactaca   4440
gttaaagatc tcactatgaa gacactcaac cctacacatg atattattgc tttatgtgaa   4500
tttgaaaaca tagtaacatc aaaaaaagtc ataataccaa catacctaag atccatcagt   4560
gtcagaaata aagatctgaa cacacttgaa aatataacaa ccactgaatt caaaaatgct   4620
atcacaaatg caaaaatcat cccttactca ggattactat tagtcatcac agtgactgac   4680
aacaaaggag cattcaaata cataaagcca caaagtcaat tcatagtaga tcttggagct   4740
tacctagaaa aagaaagtat atattatgtt accacaaatt ggaagcacac agctacacga   4800
tttgcaatca aacccatgga agattaacct ttttcctcta catcagtgtg ttaattcata   4860
caaactttct acctacattc ttcacttcac catcacaatc acaaacactc tgtggttcaa   4920
ccaatcaaac aaaacttatc tgaagtccca gatcatccca agtcattgtt tatcagatct   4980
agtactcaaa taagttaata aaaaatatac acatggacgt ccatggggca aatgcaaaca   5040
tgtccaaaaa caaggaccaa cgcaccgcta agacattaga aaggacctgg gacactctca   5100
atcatttatt attcatatca tcgtgcttat ataagttaaa tcttaaatct gtagcacaaa   5160
tcacattatc cattctggca atgataatct caacttcact tataattgca gccatcatat   5220
tcatagcctc ggcaaaccac aaagtcacac caacaactgc aatcatacaa gatgcaacaa   5280
gccagatcaa gaacacaacc ccaacatacc tcacccagaa tcctcagctt ggaatcagtc   5340
cctctaatcc gtctgaaatt acatcacaaa tcaccaccat actagcttca acaacaccag   5400
gagtcaagtc aaccctgcaa tccacaacag tcaagaccaa aaacacaaca acaactcaaa   5460
cacaacccag caagcccacc acaaaacaac gccaaaacaa accaccaagc aaacccaata   5520
atgattttca ctttgaagtg ttcaactttg taccctgcag catatgcagc aacaatccaa   5580
cctgctgggc tatctgcaaa agaataccaa acaaaaaacc aggaaagaaa accactacca   5640
agcccacaaa aaaaccaacc ctcaagacaa ccaaaaaaga tcccaaacct caaaccacta   5700
aatcaaagga agtacccacc accaagccca cagaagagcc aaccatcaac accaccaaaa   5760
caaacatcat aactacacta ctcacctcca acaccacagg aaatccagaa ctcacaagtc   5820
aaatggaaac cttccactca acttcctccg aaggcaatcc aagcccttct caagtctcta   5880
caacatccga gtacccatca caaccttcat ctccacccaa cacaccacgc cagtagttac   5940
ttaaaaacat attatcacaa aaggccttga ccaaccgcgg agaatcaaaa taaactctgg   6000
ggcaaataac aatggagttg ccaatcctca aagcaaatgc aattaccaca atcctcgctg   6060
cagtcacatt ttgctttgct tctagtcaaa acatcactga agaattttat caatcaacat   6120
gcagtgcagt tagcaaaggc tatcttagtg ctctaagaac tggttggtat actagtgtta   6180
taactataga attaagtaat atcaagaaaa ataagtgtaa tggaacagat gctaaggtaa   6240
aattgatgaa acaagaatta gataaatata aaaatgctgt aacagaattg cagttgctca   6300
tgcaaagcac accagcagca aacaatcgag ccagaagaga actaccaagg tttatgaatt   6360
atacactcaa caataccaaa aaaaccaatg taacattaag caagaaaagg aaaagaagat   6420
ttcttggttt tttgttaggt gttggatctg caatcgccag tggcattgct gtatctaagg   6480
tcctgcactt agaaggagaa gtgaacaaga tcaaaagtgc tctactatcc acaaacaagg   6540
ccgtagtcag cttatcaaat ggagttagtg tcttaaccag cagagtgtta gacctcaaaa   6600
```

-continued

```
actatataga taaacaattg ttacctattg tgaataagca aagctgcaga atatcaaata   6660
tagaaactgt gatagagttc caacaaaaga acaacagact actagagatt accagggaat   6720
ttagtgttaa tgcaggtgta actacacctg taagcactta catgttaact aatagtgaat   6780
tattgtcatt aatcaatgat atgcctataa caaatgatca gaaaaagtta atgtccaaca   6840
atgttcaaat agttagacag caaagttact ctatcatgtc cataataaaa gaggaagtct   6900
tagcatatgt agtacaatta ccactatatg gtgtgataga tacaccttgt tggaaattac   6960
acacatcccc tctatgtaca accaacacaa aagaagggtc aaacatctgt ttaacaagaa   7020
ctgacagagg atggtactgt gacaatgcag gatcagtatc tttcttccca caagctgaaa   7080
aatgtaaagt tcaatcgaat cgagtatttt gtgacacaat gtacagttta acattaccaa   7140
gtgaagtaaa tctctgcaat gttgacatat tcaatcccaa atatgattgt aaaattatga   7200
cttcaaaaac agatgtaagc agctccgtta tcacatctct aggagccatt gtgtcatgct   7260
atggcaaaac taaatgtaca gcatccaata aaaatcgtgg aatcataaag acattttcta   7320
acgggtgtga ttatgtatca aataaagggg tggacactgt gtctgtaggt aacacattat   7380
attatgtaaa taagcaagaa ggcaaaagtc tctatgtaaa aggtgaacca ataataaatt   7440
tctatgaccc attagtattc cctctgatg aatttgatgc atcaatatct caagtcaatg    7500
agaagattaa ccagagttta gcatttattc gtaaatccga tgaattatta cataatgtaa   7560
atgctggtaa atcaaccaca aatatcatga taactactat aattatagtg attatagtaa   7620
tattgttatc attaattgct gttggactgc tcctatactg taaggccaga agcacaccag   7680
tcacactaag caaggatcaa ctgagtggta taaataatat tgcatttagt aactgaataa   7740
aaatagcacc taatcatgtt cttacaatgg tttactatct gctcatagac aacccatcta   7800
tcattggatt ttcttaaaat ctgaacttca tcgaaactct tatctataaa ccatctcact   7860
tacactattt aagtagattc ctagtttata gttatataaa acacaattga atgccagtcg   7920
accttaccat ctgtaaaaat gaaaactggg gcaaatatgt cacgaaggaa tccttgcaaa   7980
tttgaaattc gaggtcattg cttaaatggt aagaggtgtc attttagtca taattatttt   8040
gaatggccac cccatgcact gcttgtaaga caaaacttta tgttaaacag aatacttaag   8100
tctatggata aaagtataga taccttatca gaaataagtg gagctgcaga gttggacaga   8160
acagaagagt atgctcttgg tgtagttgga gtgctagaga gttatatagg atcaataaac   8220
aatataacta aacaatcagc atgtgttgcc atgagcaaac tcctcactga actcaatagt   8280
gatgatatca aaaagctgag ggacaatgaa gagctaaatt cacccaagat aagagtgtac   8340
aatactgtca tatcatatat tgaaagcaac aggaaaaaca ataaacaaac tatccatctg   8400
ttaaaaagat tgccagcaga cgtattgaag aaaaccatca aaaacacatt ggatatccat   8460
aagagcataa ccatcaacaa cccaaaagaa tcaactgtta gtgatacaaa tgaccatgcc   8520
aaaaataatg atactacctg acaaatatcc ttgtagtata acttccatac taataacaag   8580
tagatgtaga gttactatgt ataatcaaaa gaacacacta tatttcaatc aaaacaaccc   8640
aaataaccat atgtactcac cgaatcaaac attcaatgaa atccattgga cctctcaaga   8700
attgattgac acaattcaaa attttctaca acatctaggt attattgagg atatatatac   8760
aatatatata ttagtgtcat aacactcaat tctaacactc accacatcgt tacattatta   8820
attcaaacaa ttcaagttgt gggacaaaat ggatcccatt attaatggaa attctgctaa   8880
tgtttatcta accgatagtt atttaaaagg tgttatctct ttctcagagt gtaatgcttt   8940
```

```
aggaagttac atattcaatg gtccttatct caaaaatgat tataccaact taattagtag    9000
acaaaatcca ttaatagaac acatgaatct aaagaaacta aatataacac agtccttaat    9060
atctaagtat cataaaggtg aaataaaatt agaagaacct acttattttc agtcattact    9120
tatgacatac aagagtatga cctcgtcaga acagattgct accactaatt tacttaaaaa    9180
gataataaga agagctatag aaataagtga tgtcaaagtc tatgctatat tgaataaact    9240
agggcttaaa gaaaaggaca agattaaatc caacaatgga caagatgaag acaactcagt    9300
tattacgacc ataatcaaag atgatatact ttcagctgtt aaagataatc aatctcatct    9360
taaagcagac aaaaatcact ctacaaaaca aaaagacaca atcaaaacaa cactcttgaa    9420
gaaattgatg tgttcaatgc aacatcctcc atcatggtta atacattggt ttaacttata    9480
cacaaaatta aacaacatat taacacagta tcgatcaaat gaggtaaaaa accatgggtt    9540
tacattgata gataatcaaa ctcttagtgg atttcaattt attttgaacc aatatggttg    9600
tatagtttat cataaggaac tcaaaagaat tactgtgaca acctataatc aattcttgac    9660
atggaaagat attagcctta gtagattaaa tgtttgttta attacatgga ttagtaactg    9720
cttgaacaca ttaaataaaa gcttaggctt aagatgcgga ttcaataatg ttatcttgac    9780
acaactattc ctttatggag attgtatact aaagctattt cacaatgagg ggttctacat    9840
aataaaagag gtagagggat ttattatgtc tctaatttta aatataacag aagaagatca    9900
attcagaaaa cgattttata atagtatgct caacaacatc acagatgctg ctaataaagc    9960
tcagaaaaat ctgctatcaa gagtatgtca tacattatta gataagacag tgtccgataa   10020
tataataaat ggcagatgga taattctatt aagtaagttc cttaaattaa ttaagcttgc   10080
aggtgacaat aaccttaaca atctgagtga actatatttt ttgttcagaa tatttggaca   10140
cccaatggta gatgaaagac aagccatgga tgctgttaaa attaattgca atgagaccaa   10200
attttacttg ttaagcagtc tgagtatgtt aagaggtgcc tttatatata gaattataaa   10260
agggtttgta aataattaca acagatggcc tactttaaga aatgctattg ttttaccctt   10320
aagatggtta acttactata aactaaacac ttatccttct ttgttggaac ttacagaaag   10380
agatttgatt gtgttatcag gactacgttt ctatcgtgag tttcggttgc ctaaaaaagt   10440
ggatcttgaa atgattataa atgataaagc tatatcacct cctaaaaatt tgatatggac   10500
tagtttccct agaaattaca tgccatcaca catacaaaac tatatagaac atgaaaaatt   10560
aaaattttcc gagagtgata aatcaagaag agtattagag tattatttaa gagataacaa   10620
attcaatgaa tgtgatttat acaactgtgt agttaatcaa agttatctca acaaccctaa   10680
tcatgtggta tcattgacag gcaaagaaag agaactcagt gtaggtagaa tgtttgcaat   10740
gcaaccggga atgttcagac aggttcaaat attggcagag aaaatgatag ctgaaaacat   10800
tttacaattc tttcctgaaa gtcttacaag atatggtgat ctagaactac aaaaaatatt   10860
agaattgaaa gcaggaataa gtaacaaatc aaatcgctac aatgataatt acaacaatta   10920
cattagtaag tgctctatca tcacagatct cagcaaattc aatcaagcat ttcgatatga   10980
aacgtcatgt atttgtagtg atgtgctgga tgaactgcat ggtgtacaat ctctattttc   11040
ctggttacat ttaactattc ctcatgtcac aataaatatgc acatataggc atgcaccccc   11100
ctatatagga gatcatattg tagatcttaa caatgtagat gaacaaagtg gattatatag   11160
atatcacatg ggtggcatcg aagggtggtg tcaaaaactg tggaccatag aagctatatc   11220
actattggat ctaatatctc tcaaagggaa attctcaatt actgctttaa ttaatggtga   11280
caatcaatca atagatataa gcaaaccaat cagactcatg gaaggtcaaa ctcatgctca   11340
```

```
agcagattat ttgctagcat taaatagcct taaattactg tataaagagt atgcaggcat  11400
aggccacaaa ttaaaaggaa ctgagactta tatatcacga gatatgcaat ttatgagtaa  11460
aacaattcaa cataacggtg tatattaccc agctagtata aagaaagtcc taagagtggg  11520
accgtggata aacactatac ttgatgattt caaagtgagt ctagaatcta taggtagttt  11580
gacacaagaa ttagaatata gaggtgaaag tctattatgc agtttaatat ttagaaatgt  11640
atggttatat aatcagattg ctctacaatt aaaaaatcat gcattatgta acaataaact  11700
atatttggac atattaaagg ttctgaaaca cttaaaaacc ttttttaatc ttgataatat  11760
tgatacagca ttaacattgt atatgaattt acccatgtta tttggtggtg gtgatcccaa  11820
cttgttatat cgaagtttct atagaagaac tcctgacttc ctcacagagg ctatagttca  11880
ctctgtgttc atacttagtt attatacaaa ccatgactta aaagataaac ttcaagatct  11940
gtcagatgat agattgaata agttcttaac atgcataatc acgtttgaca aaaaccctaa  12000
tgctgaattc gtaacattga tgagagatcc tcaagcttta gggtctgaga gacaagctaa  12060
aattactagc gaaatcaata gactggcagt tacagaggtt ttgagtacag ctccaaacaa  12120
aatattctcc aaaagtgcac aacattatac tactacagag atagatctaa atgatattat  12180
gcaaaatata gaacctacat atcctcatgg gctaagagtt gtttatgaaa gtttaccctt  12240
ttataaagca gagaaaatag taaatcttat atcaggtaca aaatctataa ctaacatact  12300
ggaaaaaact tctgccatag acttaacaga tattgataga gccactgaga tgatgaggaa  12360
aaacataact ttgcttataa ggatacttcc attggattgt aacagagata aaagagagat  12420
attgagtatg gaaaacctaa gtattactga attaagcaaa tatgttaggg aaagatcttg  12480
gtctttatcc aatatagttg gtgttacatc acccagtatc atgtatacaa tggacatcaa  12540
atatactaca agcactatat ctagtggcat aattatagag aaatataatg ttaacagttt  12600
aacacgtggt gagagaggac ccactaaacc atgggttggt tcatctacac aagagaaaaa  12660
aacaatgcca gtttataata gacaagtctt aaccaaaaaa cagagagatc aaatagatct  12720
attagcaaaa ttggattggg tgtatgcatc tatagataac aaggatgaat tcatggaaga  12780
actcagcata ggaacccttg ggttaacata tgaaaaggcc aagaaattat ttccacaata  12840
tttaagtgtc aattatttgc atcgccttac agtcagtagt agaccatgtg aattccctgc  12900
atcaatacca gcttatagaa caacaaatta tcactttgac actagcccta ttaatcgcat  12960
attaacagaa aagtatggtg atgaagatat tgacatagta ttccaaaact gtataagctt  13020
tggccttagt ttaatgtcag tagtagaaca atttactaat gtatgtccta acagaattat  13080
tctcatacct aagcttaatg agatacattt gatgaaacct cccatattca caggtgatgt  13140
tgatattcac aagttaaaac aagtgataca aaaacagcat atgtttttac cagacaaaat  13200
aagtttgact caatatgtgg aattattctt aagtaataaa acactcaaat ctggatctca  13260
tgttaattct aatttaatat tggcacataa aatatctgac tattttcata atacttacat  13320
tttaagtact aatttagctg gacattggat tctgattata caacttatga aagattctaa  13380
aggtattttt gaaaaagatt ggggagaggg atatataact gatcatatgt ttattaattt  13440
gaaagttttc ttcaatgctt ataagaccta tctcttgtgt tttcataaag gttatggcaa  13500
agcaaagctg gagtgtgata tgaacacttc agatcttcta tgtgtattgg aattaataga  13560
cagtagttat tggaagtcta tgtctaaggt atttttagaa caaaaagtta tcaaatacat  13620
tcttagccaa gatgcaagtt tacatagagt aaaaggatgt catagcttca aattatggtt  13680
```

```
tcttaaacgt cttaatgtag cagaattcac agtttgccct tgggttgtta acatagatta  13740
tcatccaaca catatgaaag caatattaac ttatatagat cttgttagaa tgggattgat  13800
aaatatagat agaatacaca ttaaaaataa acacaaattc aatgatgaat tttatacttc  13860
taatctcttc tacattaatt ataacttctc agataatact catctattaa ctaaacatat  13920
aaggattgct aattctgaat tagaaaataa ttacaacaaa ttatatcatc ctacaccaga  13980
aaccctagag aatatactag ccaatccgat taaaagtaat gacaaaaaga cactgaatga  14040
ctattgtata ggtaaaaatg ttgactcaat aatgttacca ttgttatcta ataagaagct  14100
tattaaatcg tctgcaatga ttagaaccaa ttacagcaaa caagatttgt ataatttatt  14160
ccctatggtt gtgattgata gaattataga tcattcaggc aatacagcca aatccaacca  14220
actttacact actacttccc accaaatatc tttagtgcac aatagcacat cactttactg  14280
catgcttcct tggcatcata ttaatagatt caattttgta tttagttcta caggttgtaa  14340
aattagtata gagtatattt taaaagatct taaaattaaa gatcccaatt gtatagcatt  14400
cataggtgaa ggagcaggga atttattatt gcgtacagta gtggaacttc atcctgacat  14460
aagatatatt tacagaagtc tgaaagattg caatgatcat agtttaccta ttgagttttt  14520
aaggctgtac aatggacata tcaacattga ttatggtgaa aatttgacca ttcctgctac  14580
agatgcaacc aacaacattc attggtctta tttacatata aagtttgctg aacctatcag  14640
tctttttgtc tgtgatgccg aattgtctgt aacagtcaac tggagtaaaa ttataataga  14700
atggagcaag catgtaagaa agtgcaagta ctgttcctca gttaataaat gtatgttaat  14760
agtaaaatat catgctcaag atgatattga tttcaaatta gacaatataa ctatattaaa  14820
aacttatgta tgcttaggca gtaagttaaa gggatcggag gtttacttag tccttacaat  14880
aggtcctgcg aatatattcc cagtatttaa tgtagtacaa aatgctaaat tgatactatc  14940
aagaaccaaa aatttcatca tgcctaagaa agctgataaa gagtctattg atgcaaatat  15000
taaaagtttg ataccctttc tttgttaccc tataacaaaa aaaggaatta atactgcatt  15060
gtcaaaacta aagagtgttg ttagtggaga tatactatca tattctatag ctggacgtaa  15120
tgaagttttc agcaataaac ttataaatca taagcatatg aacatcttaa aatggttcaa  15180
tcatgtttta aatttcagat caacagaact aaactataac catttatata tggtagaatc  15240
tacatatcct tacctaagtg aattgttaaa cagcttgaca accaatgaac ttaaaaaact  15300
gattaaaatc acaggtagtc tgttatacaa ctttcataat gaataatgaa taaagatctt  15360
ataataaaaa ttcccatagc tatacactaa cactgtattc aattatagtt attaaaaatt  15420
aaaaatcgta cgatttttta aataactttt agtgaactaa tcctaaagtt atcattttaa  15480
tcttggagga ataaatttaa accctaatct aattggttta tatgtgtatt aactaaatta  15540
cgagatatta gtttttgaca cttttttttct cgt                              15573
```

```
<210> SEQ ID NO 2
<211> LENGTH: 15573
<212> TYPE: DNA
<213> ORGANISM: respiratory syncytial virus

<400> SEQUENCE: 2

acgcgaaaaa atgcgtacaa caaacttgca taaaccaaaa aaatggggca aataagaatt     60
tgataagtac cacttaaatt taactccctt gcttagcgat ggtgagcgag ctgattaagg    120
agaacatgca catgaagctg tacatggagg gcaccgtgaa caaccaccac ttcaagtgca    180
catccgaggg cgaaggcaag ccctacgagg gcacccagac catgagaatc aaggcggtcg    240
```

```
agggcggccc tctccccttc gccttcgaca tcctggctac cagcttcatg tacggcagca    300
aaaccttcat caaccacacc cagggcatcc ccgacttctt taagcagtcc ttccccgagg    360
gcttcacatg ggagagagtc accacatacg aagacggggg cgtgctgacc gctacccagg    420
acaccagcct ccaggacggc tgcctcatct acaacgtcaa gatcagaggg gtgaacttcc    480
catccaacgg ccctgtgatg cagaagaaaa cactcggctg ggaggcctcc accgagaccc    540
tgtaccccgc tgacggcggc ctggaaggca gagccgacat ggccctgaag ctcgtgggcg    600
ggggccacct gatctgcaac ttgaagacca catacagatc caagaaaccc gctaagaacc    660
tcaagatgcc cggcgtctac tatgtggaca gaagactgga aagaatcaag gaggccgaca    720
aagagaccta cgtcgagcag cacgaggtgg ctgtggccag atactgcgac ctccctagca    780
aactggggca cagatgagta ttcaattata gttattaaaa acttaacaga agacaaaaat    840
ggggcaaata agaatttgat aagtaccact taaatttaac tcccttgctt agcgatgggt    900
tcgaattcgc tatcgatgat aaaagtacgt ctacaaaatc tatttgataa tgatgaagta    960
gcgctactaa aaataacgtg ttatacggat aaactaatac atctaacgaa tgcgctagcg   1020
aaagcggtaa tacatacgat aaaactaaat ggtatagtat ttgtacatgt aataacgtcg   1080
tcggatatat gtccgaataa taatatagta gtaaaatcga attttacgac gatgccggta   1140
ctacaaaatg gtggttatat atgggaaatg atggaactaa cgcattgttc gcaaccgaat   1200
ggtctactag atgataattg tgaaataaaa ttttcgaaaa aactatcgga ttcgacgatg   1260
acgaattata tgaatcaact atcggaacta ctaggttttg atctaaatcc gtaaattata   1320
attaatatca actagcaaat caatgtcact aacaccatta gttaatataa aacttaacag   1380
aagacaaaaa tggggcaaat aaatcaattc agccaaccca accatggata cgacgcataa   1440
tgataatacg ccgcaacgtc taatgataac ggatatgcgt ccgctatcgc tagaaacgat   1500
aataacgtcg ctaacgcgtg atataataac gcataaattt atatatctaa taaatcatga   1560
atgtatagta cgtaaactag atgaacgtca agcgacgttt acgtttctag taaattatga   1620
aatgaaacta ctacataaag taggttcgac gaaatataaa aaatatacgg aatataatac   1680
gaaatatggt acgtttccga tgccgatatt tataaatcat gatggttttc tagaatgtat   1740
aggtataaaa ccgacgaaac atacgccgat aatatataaa tatgatctaa atccgtaaat   1800
ttcaacacaa tattcacaca atctaaaaca acaactctat gcataactat actccatagt   1860
ccagatggag cctgaaaatt atagtaattt aaaattaagg agagatataa gatagaagat   1920
ggggcaaata caaagatggc tcttagcaaa gtcaagttga atgatacact caacaaagat   1980
caacttctgt catccagcaa atacaccatc caacggagca caggagatag tattgatact   2040
cctaattatg atgtgcagaa acacatcaat aagttatgtg gcatgttatt aatcacagaa   2100
gatgctaatc ataaattcac tgggttaata ggtatgttat atgcgatgtc taggttagga   2160
agagaagaca ccataaaaat actcagagat gcgggatatc atgtaaaagc aaatggagta   2220
gatgtaacaa cacatcgtca agacattaat ggaaaagaaa tgaaatttga agtgttaaca   2280
ttggcaagct taacaactga aattcaaatc aacattgaga tagaatctag aaaatcctac   2340
aaaaaaatgc taaaagaaat gggagaggta gctccagaat acaggcatga ctctcctgat   2400
tgtgggatga taatattatg tatagcagca ttagtaataa ctaaattagc agcaggggac   2460
agatctggtc ttacagccgt gattaggaga gctaataatg tcctaaaaaa tgaaatgaaa   2520
cgttacaaag gcttactacc caaggacata gccaacagct tctatgaagt gtttgaaaaa   2580
```

-continued

```
catccccact ttatagatgt ttttgttcat tttggtatag cacaatcttc taccagaggt   2640

ggcagtagag ttgaagggat ttttgcagga ttgtttatga atgcctatgg tgcagggcaa   2700

gtgatgttac ggtggggagt cttagcaaaa tcagttaaaa atattatgtt aggacatgct   2760

agtgtgcaag cagaaatgga acaagttgtt gaggtttatg aatatgccca aaaattgggt   2820

ggtgaagcag gattctacca tatattgaac aacccaaaag catcattatt atctttgact   2880

caatttcctc acttctccag tgtagtatta ggcaatgctg ctggcctagg cataatggga   2940

gagtacagag gtacaccgag gaatcaagat ctatatgatg cagcaaaggc atatgctgaa   3000

caactcaaag aaaatggtgt gattaactac agtgtactag acttgacagc agaagaacta   3060

gaggctatca aacatcagct taatccaaaa gataatgatg tagagctttg agttaataaa   3120

aaatggggca aataaatcat catggaaaag tttgctcctg aattccatgg agaagatgca   3180

aacaacaggg ctactaaatt cctagaatca ataaagggca aattcacatc acccaaagat   3240

cccaagaaaa aagatagtat catatctgtc aactcaatag atatagaagt aaccaaagaa   3300

agccctataa catcaaattc aactattatc aacccaacaa atgagacaga tgatactgca   3360

gggaacaagc ccaattatca aagaaaacct ctagtaagtt tcaaagaaga ccctacacca   3420

agtgataatc ccttttctaa actatacaaa gaaaccatag aaacatttga taacaatgaa   3480

gaagaatcca gctattcata cgaagaaata aatgatcaga caaacgataa tataacagca   3540

agattagata ggattgatga aaaattaagt gaaatactag gaatgcttca cacattagta   3600

gtggcaagtg caggacctac atctgctcgg gatggtataa gagatgccat gattggttta   3660

agagaagaaa tgatagaaaa aatcagaact gaagcattaa tgaccaatga cagattagaa   3720

gctatggcaa gactcaggaa tgaggaaagt gaaaagatgg caaaagacac atcagatgaa   3780

gtgtctctca atccaacatc agagaaattg aacaacctat tggaagggaa tgatagtgac   3840

aatgatctat cacttgaaga tttctgatta gttaccactc ttcacatcaa cacacaatac   3900

caacagaaga ccaacaaact aaccaaccca atcatccaac caaacatcca tccgccaatc   3960

agccaaacag ccaacaaaac aaccagccaa tccaaaacta accacccgga aaaaatctat   4020

aatatagtta caaaaaaagg aaagggtggg gcaaatatgg aaacatacgt gaacaagctt   4080

cacgaaggct ccacatacac agctgctgtt caatacaatg tcttagaaaa agacgatgac   4140

cctgcatcac ttacaatatg ggtgcccatg ttccaatcat ctatgccagc agatttactt   4200

ataaaagaac tagctaatgt caacatacta gtgaaacaaa tatccacacc caagggacct   4260

tcactaagag tcatgataaa ctcaagaagt gcagtgctag cacaaatgcc cagcaaattt   4320

accatatgcg ctaatgtgtc cttggatgaa agaagcaaac tagcatatga tgtaaccaca   4380

ccctgtgaaa tcaaggcatg tagtctaaca tgcctaaaat caaaaaatat gttgactaca   4440

gttaaagatc tcactatgaa gacactcaac cctacacatg atattattgc tttatgtgaa   4500

tttgaaaaca tagtaacatc aaaaaaagtc ataataccaa catacctaag atccatcagt   4560

gtcagaaata aagatctgaa cacacttgaa aatataacaa ccactgaatt caaaaatgct   4620

atcacaaatg caaaaatcat cccttactca ggattactat tagtcatcac agtgactgac   4680

aacaaaggag cattcaaata cataaagcca caaagtcaat tcatagtaga tcttggagct   4740

tacctagaaa aagaaagtat atattatgtt accacaaatt ggaagcacac agctacacga   4800

tttgcaatca aacccatgga agattaacct ttttcctcta catcagtgtg ttaattcata   4860

caaactttct acctacattc ttcacttcac catcacaatc acaaacactc tgtggttcaa   4920

ccaatcaaac aaaacttatc tgaagtccca gatcatccca agtcattgtt tatcagatct   4980
```

```
agtactcaaa taagttaata aaaaatatac acatggacgt ccatggggca aatgcaaaca   5040
tgtcgaaaaa caaagaccaa cgtaccgcga agacgttaga acgtacctgg gatactctaa   5100
atcatttact attcatatcg tcgtgcctat ataagctaaa tcttaaatcg gtagcacaaa   5160
taacactatc catactggcg ataataatct cgacttcgct tataatagca gcgatcatat   5220
ttatagcctc ggcgaaccat aaagtcacgc caacgactgc gatcatacaa gatgcgacat   5280
cgcagataaa gaatacaacg ccaacgtacc taacccaaaa tcctcaactt ggtatctcgc   5340
cctcgaatcc gtctgaaata acatcgcaaa tcacgaccat actagcgtca acgacaccgg   5400
gagtaaagtc gaccctacaa tccacgacag taaagacgaa aaacacgaca acgactcaaa   5460
cgcaaccctc gaagccgacc acgaaacaac gccaaaataa accaccgagc aaaccgaata   5520
atgattttca ctttgaagta ttcaattttg taccctgtag catatgtagc aataatccaa   5580
cgtgctgggc gatctgtaaa agaataccga acaaaaaacc gggaaaaaaa accacgacca   5640
aacccacgaa aaaaccaacg ctcaaaacaa cgaaaaaaga tcccaaaccg caaaccacga   5700
aatcaaaaga agtacccacg accaaaccca cggaagagcc gaccataaac acgaccaaaa   5760
cgaacataat aactacgcta ctcacgtcca ataccacggg aaatccggaa ctcacgagtc   5820
aaatggaaac gtttcactcg acttcgtccg aaggtaatcc atcgccttcg caagtctcga   5880
caacgtccga atacccgtca caaccgtcat cgccaccgaa cacgccacgt cagtagttac   5940
ttaaaaacat attatcacaa aaggccttga ccaaccgcgg agaatcaaaa taaactctgg   6000
ggcaaataac aatggagttg ccaatcctca aagcaaatgc aattaccaca atcctcgctg   6060
cagtcacatt ttgctttgct tctagtcaaa acatcactga agaattttat caatcaacat   6120
gcagtgcagt tagcaaaggc tatcttagtg ctctaagaac tggttggtat actagtgtta   6180
taactataga attaagtaat atcaagaaaa ataagtgtaa tggaacagat gctaaggtaa   6240
aattgatgaa acaagaatta gataaatata aaaatgctgt aacagaattg cagttgctca   6300
tgcaaagcac accagcagca aacaatcgag ccagaagaga actaccaagg tttatgaatt   6360
atacactcaa caataccaaa aaaaccaatg taacattaag caagaaaagg aaaagaagat   6420
ttcttggttt tttgttaggt gttggatctg caatcgccag tggcattgct gtatctaagg   6480
tcctgcactt agaaggagaa gtgaacaaga tcaaaagtgc tctactatcc acaaacaagg   6540
ccgtagtcag cttatcaaat ggagttagtg tcttaaccag cagagtgtta gacctcaaaa   6600
actatataga taaacaattg ttacctattg tgaataagca aagctgcaga atatcaaata   6660
tagaaactgt gatagagttc caacaaaaga acaacagact actagagatt accagggaat   6720
ttagtgttaa tgcaggtgta actacacctg taagcactta catgttaact aatagtgaat   6780
tattgtcatt aatcaatgat atgcctataa caaatgatca gaaaaagtta atgtccaaca   6840
atgttcaaat agttagacag caaagttact ctatcatgtc cataataaaa gaggaagtct   6900
tagcatatgt agtacaatta ccactatatg gtgtgataga tacaccttgt tggaaattac   6960
acacatcccc tctatgtaca accaacacaa aagaagggtc aaacatctgt ttaacaagaa   7020
ctgacagagg atggtactgt gacaatgcag gatcagtatc tttcttccca caagctgaaa   7080
aatgtaaagt tcaatcgaat cgagtatttt gtgacacaat gtacagttta acattaccaa   7140
gtgaagtaaa tctctgcaat gttgacatat tcaatcccaa atatgattgt aaaattatga   7200
cttcaaaaac agatgtaagc agctccgtta tcacatctct aggagccatt gtgtcatgct   7260
atggcaaaac taaatgtaca gcatccaata aaaatcgtgg aatcataaag acattttcta   7320
```

```
acgggtgtga ttatgtatca aataaagggg tggacactgt gtctgtaggt aacacattat   7380
attatgtaaa taagcaagaa ggcaaaagtc tctatgtaaa aggtgaacca ataataaatt   7440
tctatgaccc attagtattc ccctctgatg aatttgatgc atcaatatct caagtcaatg   7500
agaagattaa ccagagttta gcatttattc gtaaatccga tgaattatta cataatgtaa   7560
atgctggtaa atcaaccaca aatatcatga taactactat aattatagtg attatagtaa   7620
tattgttatc attaattgct gttggactgc tcctatactg taaggccaga agcacaccag   7680
tcacactaag caaggatcaa ctgagtggta taaataatat tgcatttagt aactgaataa   7740
aaatagcacc taatcatgtt cttacaatgg tttactatct gctcatagac aacccatcta   7800
tcattggatt ttcttaaaat ctgaacttca tcgaaactct tatctataaa ccatctcact   7860
tacactattt aagtagattc ctagtttata gttatataaa acacaattga atgccagtcg   7920
accttaccat ctgtaaaaat gaaaactggg gcaaatatgt cacgaaggaa tccttgcaaa   7980
tttgaaattc gaggtcattg cttaaatggt aagaggtgtc attttagtca taattatttt   8040
gaatggccac cccatgcact gcttgtaaga caaaacttta tgttaaacag aatacttaag   8100
tctatggata aaagtataga taccttatca gaaataagtg gagctgcaga gttggacaga   8160
acagaagagt atgctcttgg tgtagttgga gtgctagaga gttatatagg atcaataaac   8220
aatataacta aacaatcagc atgtgttgcc atgagcaaac tcctcactga actcaatagt   8280
gatgatatca aaaagctgag ggacaatgaa gagctaaatt cacccaagat aagagtgtac   8340
aatactgtca tatcatatat tgaaagcaac aggaaaaaca ataaacaaac tatccatctg   8400
ttaaaaagat tgccagcaga cgtattgaag aaaaccatca aaaacacatt ggatatccat   8460
aagagcataa ccatcaacaa cccaaaagaa tcaactgtta gtgatacaaa tgaccatgcc   8520
aaaaataatg atactacctg acaaatatcc ttgtagtata acttccatac taataacaag   8580
tagatgtaga gttactatgt ataatcaaaa gaacacacta tatttcaatc aaaacaaccc   8640
aaataaccat atgtactcac cgaatcaaac attcaatgaa atccattgga cctctcaaga   8700
attgattgac acaattcaaa attttctaca acatctaggt attattgagg atatatatac   8760
aatatatata ttagtgtcat aacactcaat tctaacactc accacatcgt tacattatta   8820
attcaaacaa ttcaagttgt gggacaaaat ggatcccatt attaatggaa attctgctaa   8880
tgtttatcta accgatagtt atttaaaagg tgttatctct ttctcagagt gtaatgcttt   8940
aggaagttac atattcaatg gtccttatct caaaaatgat tataccaact taattagtag   9000
acaaaatcca ttaatagaac acatgaatct aaagaaacta aatataacac agtccttaat   9060
atctaagtat cataaaggtg aaataaaatt agaagaacct acttattttc agtcattact   9120
tatgacatac aagagtatga cctcgtcaga acagattgct accactaatt tacttaaaaa   9180
gataataaga agagctatag aaataagtga tgtcaaagtc tatgctatat tgaataaact   9240
agggcttaaa gaaaaggaca agattaaatc caacaatgga caagatgaag acaactcagt   9300
tattacgacc ataatcaaag atgatatact ttcagctgtt aaagataatc aatctcatct   9360
taaagcagac aaaaatcact ctacaaaaca aaaagacaca atcaaaacaa cactcttgaa   9420
gaaattgatg tgttcaatgc aacatcctcc atcatggtta atacattggt ttaacttata   9480
cacaaaatta aacaacatat taacacagta tcgatcaaat gaggtaaaaa accatgggtt   9540
tacattgata gataatcaaa ctcttagtgg atttcaattt attttgaacc aatatggttg   9600
tatagtttat cataaggaac tcaaaagaat tactgtgaca acctataatc aattcttgac   9660
atggaaagat attagcctta gtagattaaa tgtttgttta attacatgga ttagtaactg   9720
```

```
cttgaacaca ttaaataaaa gcttaggctt aagatgcgga ttcaataatg ttatcttgac   9780
acaactattc ctttatggag attgtatact aaagctattt cacaatgagg ggttctacat   9840
aataaaagag gtagagggat ttattatgtc tctaatttta aatataacag aagaagatca   9900
attcagaaaa cgattttata atagtatgct caacaacatc acagatgctg ctaataaagc   9960
tcagaaaaat ctgctatcaa gagtatgtca tacattatta gataagacag tgtccgataa  10020
tataataaat ggcagatgga taattctatt aagtaagttc cttaaattaa ttaagcttgc  10080
aggtgacaat aaccttaaca atctgagtga actatatttt ttgttcagaa tatttggaca  10140
cccaatggta gatgaaagac aagccatgga tgctgttaaa attaattgca atgagaccaa  10200
attttacttg ttaagcagtc tgagtatgtt aagaggtgcc tttatatata gaattataaa  10260
agggtttgta aataattaca acagatggcc tactttaaga aatgctattg ttttaccctt  10320
aagatggtta acttactata aactaaacac ttatccttct ttgttggaac ttacagaaag  10380
agatttgatt gtgttatcag gactacgttt ctatcgtgag tttcggttgc ctaaaaaagt  10440
ggatcttgaa atgattataa atgataaagc tatatcacct cctaaaaatt tgatatggac  10500
tagtttccct agaaattaca tgccatcaca catacaaaac tatatagaac atgaaaaatt  10560
aaaattttcc gagagtgata aatcaagaag agtattagag tattatttaa gagataacaa  10620
attcaatgaa tgtgatttat acaactgtgt agttaatcaa agttatctca acaaccctaa  10680
tcatgtggta tcattgacag gcaaagaaag agaactcagt gtaggtagaa tgtttgcaat  10740
gcaaccggga atgttcagac aggttcaaat attggcagag aaaatgatag ctgaaaacat  10800
tttacaattc tttcctgaaa gtcttacaag atatggtgat ctagaactac aaaaaatatt  10860
agaattgaaa gcaggaataa gtaacaaatc aaatcgctac aatgataatt acaacaatta  10920
cattagtaag tgctctatca tcacagatct cagcaaattc aatcaagcat ttcgatatga  10980
aacgtcatgt atttgtagtg atgtgctgga tgaactgcat ggtgtacaat ctctattttc  11040
ctggttacat ttaactattc ctcatgtcac aataaatatgc acatataggc atgcaccccc  11100
ctatatagga gatcatattg tagatcttaa caatgtagat gaacaaagtg gattatatag  11160
atatcacatg ggtggcatcg aagggtggtg tcaaaaactg tggaccatag aagctatatc  11220
actattggat ctaatatctc tcaaagggaa attctcaatt actgctttaa ttaatggtga  11280
caatcaatca atagatataa gcaaaccaat cagactcatg gaaggtcaaa ctcatgctca  11340
agcagattat ttgctagcat taaatagcct taaattactg tataaagagt atgcaggcat  11400
aggccacaaa ttaaaaggaa ctgagactta tatatcacga gatatgcaat ttatgagtaa  11460
aacaattcaa cataacggtg tatattaccc agctagtata aagaaagtcc taagagtggg  11520
accgtggata aacactatac ttgatgattt caaagtgagt ctagaatcta taggtagttt  11580
gacacaagaa ttagaatata gaggtgaaag tctattatgc agtttaatat ttagaaatgt  11640
atggttatat aatcagattg ctctacaatt aaaaaatcat gcattatgta acaataaact  11700
atatttggac atattaaagg ttctgaaaca cttaaaaacc ttttttaatc ttgataatat  11760
tgatacagca ttaacattgt atatgaattt acccatgtta tttggtggtg gtgatcccaa  11820
cttgttatat cgaagtttct atagaagaac tcctgacttc ctcacagagg ctatagttca  11880
ctctgtgttc atacttagtt attatacaaa ccatgactta aaagataaac ttcaagatct  11940
gtcagatgat agattgaata agttcttaac atgcataatc acgtttgaca aaaaccctaa  12000
tgctgaattc gtaacattga tgagagatcc tcaagcttta gggtctgaga gacaagctaa  12060
```

```
aattactagc gaaatcaata gactggcagt tacagaggtt ttgagtacag ctccaaacaa  12120
aatattctcc aaaagtgcac aacattatac tactacagag atagatctaa atgatattat  12180
gcaaaatata gaacctacat atcctcatgg gctaagagtt gtttatgaaa gtttaccctt  12240
ttataaagca gagaaaatag taaatcttat atcaggtaca aaatctataa ctaacatact  12300
ggaaaaaact tctgccatag acttaacaga tattgataga gccactgaga tgatgaggaa  12360
aaacataact ttgcttataa ggatacttcc attggattgt aacagagata aaagagagat  12420
attgagtatg gaaaacctaa gtattactga attaagcaaa tatgttaggg aaagatcttg  12480
gtctttatcc aatatagttg gtgttacatc acccagtatc atgtatacaa tggacatcaa  12540
atatactaca agcactatat ctagtggcat aattatagag aaatataatg ttaacagttt  12600
aacacgtggt gagagaggac ccactaaacc atgggttggt tcatctacac aagagaaaaa  12660
aacaatgcca gtttataata gacaagtctt aaccaaaaaa cagagagatc aaatagatct  12720
attagcaaaa ttggattggg tgtatgcatc tatagataac aaggatgaat tcatggaaga  12780
actcagcata ggaacccttg ggttaacata tgaaaaggcc aagaaattat ttccacaata  12840
tttaagtgtc aattatttgc atcgccttac agtcagtagt agaccatgtg aattccctgc  12900
atcaatacca gcttatagaa caacaaatta tcactttgac actagcccta ttaatcgcat  12960
attaacagaa aagtatggtg atgaagatat tgacatagta ttccaaaact gtataagctt  13020
tggccttagt ttaatgtcag tagtagaaca atttactaat gtatgtccta acagaattat  13080
tctcatacct aagcttaatg agatacattt gatgaaacct cccatattca caggtgatgt  13140
tgatattcac aagttaaaac aagtgataca aaaacagcat atgtttttac cagacaaaat  13200
aagtttgact caatatgtgg aattattctt aagtaataaa acactcaaat ctggatctca  13260
tgttaattct aatttaatat tggcacataa aatatctgac tattttcata atacttacat  13320
tttaagtact aatttagctg gacattggat tctgattata caacttatga aagattctaa  13380
aggtattttt gaaaaagatt ggggagaggg atatataact gatcatatgt ttattaattt  13440
gaaagttttc ttcaatgctt ataagaccta tctcttgtgt tttcataaag gttatggcaa  13500
agcaaagctg gagtgtgata tgaacacttc agatcttcta tgtgtattgg aattaataga  13560
cagtagttat tggaagtcta tgtctaaggt atttttagaa caaaaagtta tcaaatacat  13620
tcttagccaa gatgcaagtt tacatagagt aaaaggatgt catagcttca aattatggtt  13680
tcttaaacgt cttaatgtag cagaattcac agtttgccct tgggttgtta acatagatta  13740
tcatccaaca catatgaaag caatattaac ttatatagat cttgttagaa tgggattgat  13800
aaatatagat agaatacaca ttaaaaataa acacaaattc aatgatgaat tttatacttc  13860
taatctcttc tacattaatt ataacttctc agataatact catctattaa ctaaacatat  13920
aaggattgct aattctgaat tagaaaataa ttacaacaaa ttatatcatc ctacaccaga  13980
aaccctagag aatatactag ccaatccgat taaaagtaat gacaaaaaga cactgaatga  14040
ctattgtata ggtaaaaatg ttgactcaat aatgttacca ttgttatcta ataagaagct  14100
tattaaatcg tctgcaatga ttagaaccaa ttacagcaaa caagatttgt ataatttatt  14160
ccctatggtt gtgattgata gaattataga tcattcaggc aatacagcca aatccaacca  14220
actttacact actacttccc accaaatatc tttagtgcac aatagcacat cactttactg  14280
catgcttcct tggcatcata ttaatagatt caattttgta tttagttcta caggttgtaa  14340
aattagtata gagtatattt taaaagatct taaaattaaa gatcccaatt gtatagcatt  14400
cataggtgaa ggagcaggga atttattatt gcgtacagta gtggaacttc atcctgacat  14460
```

```
aagatatatt tacagaagtc tgaaagattg caatgatcat agtttaccta ttgagttttt  14520
aaggctgtac aatggacata tcaacattga ttatggtgaa aatttgacca ttcctgctac  14580
agatgcaacc aacaacattc attggtctta tttacatata aagtttgctg aacctatcag  14640
tctttttgtc tgtgatgccg aattgtctgt aacagtcaac tggagtaaaa ttataataga  14700
atggagcaag catgtaagaa agtgcaagta ctgttcctca gttaataaat gtatgttaat  14760
agtaaaatat catgctcaag atgatattga tttcaaatta gacaatataa ctatattaaa  14820
aacttatgta tgcttaggca gtaagttaaa gggatcggag gtttacttag tccttacaat  14880
aggtcctgcg aatatattcc cagtatttaa tgtagtacaa aatgctaaat tgatactatc  14940
aagaaccaaa aatttcatca tgcctaagaa agctgataaa gagtctattg atgcaaatat  15000
taaaagtttg ataccctttc tttgttaccc tataacaaaa aaaggaatta atactgcatt  15060
gtcaaaacta aagagtgttg ttagtggaga tatactatca tattctatag ctggacgtaa  15120
tgaagttttc agcaataaac ttataaatca taagcatatg aacatcttaa aatggttcaa  15180
tcatgtttta aatttcagat caacagaact aaactataac catttatata tggtagaatc  15240
tacatatcct tacctaagtg aattgttaaa cagcttgaca accaatgaac ttaaaaaact  15300
gattaaaatc acaggtagtc tgttatacaa ctttcataat gaataatgaa taaagatctt  15360
ataataaaaa ttcccatagc tatacactaa cactgtattc aattatagtt attaaaaatt  15420
aaaaatcgta cgatttttta aataactttt agtgaactaa tcctaaagtt atcattttaa  15480
tcttggagga ataaatttaa accctaatct aattggttta tatgtgtatt aactaaatta  15540
cgagatatta gtttttgaca cttttttct cgt                                15573
```

<210> SEQ ID NO 3
<211> LENGTH: 15573
<212> TYPE: DNA
<213> ORGANISM: respiratory syncytial virus

<400> SEQUENCE: 3

```
acgcgaaaaa atgcgtacaa caaacttgca taaaccaaaa aaatggggca aataagaatt     60
tgataagtac cacttaaatt taactccctt gcttagcgat ggtgagcgag ctgattaagg    120
agaacatgca catgaagctg tacatggagg gcaccgtgaa caaccaccac ttcaagtgca    180
catccgaggg cgaaggcaag ccctacgagg gcacccagac catgagaatc aaggcggtcg    240
agggcggccc tctccccttc gccttcgaca tcctggctac cagcttcatg tacggcagca    300
aaaccttcat caaccacacc cagggcatcc ccgacttctt taagcagtcc ttccccgagg    360
gcttcacatg ggagagagtc accacatacg aagacggggg cgtgctgacc gctacccagg    420
acaccagcct ccaggacggc tgcctcatct acaacgtcaa gatcagaggg gtgaacttcc    480
catccaacgg ccctgtgatg cagaagaaaa cactcggctg ggaggcctcc accgagaccc    540
tgtaccccgc tgacggcggc ctggaaggca gagccgacat ggccctgaag ctcgtgggcg    600
gggggccacct gatctgcaac ttgaagacca catacagatc caagaaaccc gctaagaacc    660
tcaagatgcc cggcgtctac tatgtggaca gaagactgga aagaatcaag gaggccgaca    720
aagagaccta cgtcgagcag cacgaggtgg ctgtggccag atactgcgac ctccctagca    780
aactggggca cagatgagta ttcaattata gttattaaaa acttaacaga agacaaaaat    840
ggggcaaata agaatttgat aagtaccact taaatttaac tcccttgctt agcgatgggt    900
tcgaattcgc tatcgatgat aaaagtacgt ctacaaaatc tatttgataa tgatgaagta    960
```

```
gcgctactaa aaataacgtg ttatacggat aaactaatac atctaacgaa tgcgctagcg   1020
aaagcggtaa tacatacgat aaaactaaat ggtatagtat ttgtacatgt aataacgtcg   1080
tcggatatat gtccgaataa taatatagta gtaaaatcga attttacgac gatgccggta   1140
ctacaaaatg gtggttatat atgggaaatg atggaactaa cgcattgttc gcaaccgaat   1200
ggtctactag atgataattg tgaaataaaa ttttcgaaaa aactatcgga ttcgacgatg   1260
acgaattata tgaatcaact atcggaacta ctaggttttg atctaaatcc gtaaattata   1320
attaatatca actagcaaat caatgtcact aacaccatta gttaatataa aacttaacag   1380
aagacaaaaa tggggcaaat aaatcaattc agccaaccca accatggata cgacgcataa   1440
tgataatacg ccgcaacgtc taatgataac ggatatgcgt ccgctatcgc tagaaacgat   1500
aataacgtcg ctaacgcgtg atataataac gcataaattt atatatctaa taaatcatga   1560
atgtatagta cgtaaactag atgaacgtca agcgacgttt acgtttctag taaattatga   1620
aatgaaacta ctacataaag taggttcgac gaaatataaa aaatatacgg aatataatac   1680
gaaatatggt acgtttccga tgccgatatt tataaatcat gatggttttc tagaatgtat   1740
aggtataaaa ccgacgaaac atacgccgat aatatataaa tatgatctaa atccgtaaat   1800
ttcaacacaa tattcacaca atctaaaaca acaactctat gcataactat actccatagt   1860
ccagatggag cctgaaaatt atagtaattt aaaattaagg agagatataa gatagaagat   1920
ggggcaaata caaagatggc tcttagcaaa gtcaagttga atgatacact caacaaagat   1980
caacttctgt catccagcaa atacaccatc caacggagca caggagatag tattgatact   2040
cctaattatg atgtgcagaa acacatcaat aagttatgtg gcatgttatt aatcacagaa   2100
gatgctaatc ataaattcac tgggttaata ggtatgttat atgcgatgtc taggttagga   2160
agagaagaca ccataaaaat actcagagat gcgggatatc atgtaaaagc aaatggagta   2220
gatgtaacaa cacatcgtca agacattaat ggaaaagaaa tgaaatttga agtgttaaca   2280
ttggcaagct taacaactga aattcaaatc aacattgaga tagaatctag aaaatcctac   2340
aaaaaaatgc taaaagaaat gggagaggta gctccagaat acaggcatga ctctcctgat   2400
tgtgggatga taatattatg tatagcagca ttagtaataa ctaaattagc agcaggggac   2460
agatctggtc ttacagccgt gattaggaga gctaataatg tcctaaaaaa tgaaatgaaa   2520
cgttacaaag gcttactacc caaggacata gccaacagct tctatgaagt gtttgaaaaa   2580
catccccact ttatagatgt ttttgttcat tttggtatag cacaatcttc taccagaggt   2640
ggcagtagag ttgaagggat ttttgcagga ttgtttatga atgcctatgg tgcagggcaa   2700
gtgatgttac ggtggggagt cttagcaaaa tcagttaaaa atattatgtt aggacatgct   2760
agtgtgcaag cagaaatgga acaagttgtt gaggtttatg aatatgccca aaaattgggt   2820
ggtgaagcag gattctacca tatattgaac aacccaaaag catcattatt atctttgact   2880
caatttcctc acttctccag tgtagtatta ggcaatgctg ctggcctagg cataatggga   2940
gagtacagag gtacaccgag gaatcaagat ctatatgatg cagcaaaggc atatgctgaa   3000
caactcaaag aaaatggtgt gattaactac agtgtactag acttgacagc agaagaacta   3060
gaggctatca aacatcagct taatccaaaa gataatgatg tagagctttg agttaataaa   3120
aaatggggca aataaatcat catggaaaag tttgctcctg aattccatgg agaagatgca   3180
aacaacaggg ctactaaatt cctagaatca ataaagggca aattcacatc acccaaagat   3240
cccaagaaaa aagatagtat catatctgtc aactcaatag atatagaagt aaccaaagaa   3300
agccctataa catcaaattc aactattatc aacccaacaa atgagacaga tgatactgca   3360
```

```
gggaacaagc ccaattatca aagaaaacct ctagtaagtt tcaaagaaga ccctacacca   3420
agtgataatc ccttttctaa actatacaaa gaaaccatag aaacatttga taacaatgaa   3480
gaagaatcca gctattcata cgaagaaata aatgatcaga caaacgataa tataacagca   3540
agattagata ggattgatga aaaattaagt gaaatactag gaatgcttca cacattagta   3600
gtggcaagtg caggacctac atctgctcgg gatggtataa gagatgccat gattggttta   3660
agagaagaaa tgatagaaaa aatcagaact gaagcattaa tgaccaatga cagattagaa   3720
gctatggcaa gactcaggaa tgaggaaagt gaaaagatgg caaaagacac atcagatgaa   3780
gtgtctctca atccaacatc agagaaattg aacaacctat tggaagggaa tgatagtgac   3840
aatgatctat cacttgaaga tttctgatta gttaccactc ttcacatcaa cacacaatac   3900
caacagaaga ccaacaaact aaccaaccca atcatccaac caaacatcca tccgccaatc   3960
agccaaacag ccaacaaaac aaccagccaa tccaaaacta accacccgga aaaaatctat   4020
aatatagtta caaaaaaagg aaagggtggg gcaaatatgg aaacatacgt gaacaagctt   4080
cacgaaggct ccacatacac agctgctgtt caatacaatg tcttagaaaa agacgatgac   4140
cctgcatcac ttacaatatg ggtgcccatg ttccaatcat ctatgccagc agatttactt   4200
ataaaagaac tagctaatgt caacatacta gtgaaacaaa tatccacacc caagggacct   4260
tcactaagag tcatgataaa ctcaagaagt gcagtgctag cacaaatgcc cagcaaattt   4320
accatatgcg ctaatgtgtc cttggatgaa agaagcaaac tagcatatga tgtaaccaca   4380
ccctgtgaaa tcaaggcatg tagtctaaca tgcctaaaat caaaaaatat gttgactaca   4440
gttaaagatc tcactatgaa gacactcaac cctacacatg atattattgc tttatgtgaa   4500
tttgaaaaca tagtaacatc aaaaaaagtc ataataccaa catacctaag atccatcagt   4560
gtcagaaata aagatctgaa cacacttgaa aatataacaa ccactgaatt caaaaatgct   4620
atcacaaatg caaaaatcat cccttactca ggattactat tagtcatcac agtgactgac   4680
aacaaaggag cattcaaata cataaagcca caaagtcaat tcatagtaga tcttggagct   4740
tacctagaaa aagaaagtat atattatgtt accacaaatt ggaagcacac agctacacga   4800
tttgcaatca aacccatgga agattaacct ttttcctcta catcagtgtg ttaattcata   4860
caaactttct acctacattc ttcacttcac catcacaatc acaaacactc tgtggttcaa   4920
ccaatcaaac aaaacttatc tgaagtccca gatcatccca agtcattgtt tatcagatct   4980
agtactcaaa taagttaata aaaaatatac acatggacgt ccatggggca aatgcaaaca   5040
tgtcgaaaaa taaagaccaa cgtacggcga agacgctaga acgtacctgg gatacgctaa   5100
atcatttact atttatatcg tcgtgcctat ataaactaaa tcttaaatcg gtagcgcaaa   5160
taacactatc gatactggcg ataataatat cgacttcgct aataatagca gcgataatat   5220
ttatagcctc ggcgaatcat aaagtcacgc cgacgactgc gataatacaa gatgcgacat   5280
cgcaaataaa gaatacgacg ccaacgtatc taacccaaaa tccgcaactt ggtatatcgc   5340
cctcgaatcc gtcggaaata acatcgcaaa taacgaccat actagcgtcg acgacaccgg   5400
gtgtaaagtc gacgctacaa tccacgacgg taaagacgaa aaatacgaca acgacgcaaa   5460
cgcaaccgtc gaaaccgacc acgaaacaac gtcaaaataa accaccgtcg aaaccgaata   5520
atgattttca ctttgaagta tttaattttg taccctgttc gatatgtagc aataatccga   5580
cgtgctgggc gatatgtaaa agaataccga ataaaaaacc gggaaaaaaa acgacgacca   5640
aaccgacgaa aaaaccaacg ctaaaaacaa cgaaaaaaga tccgaaaccg caaaccacga   5700
```

-continued

```
aatcgaaaga agtacccacg acgaaaccca cggaagaacc gaccataaat acgaccaaaa   5760
cgaatataat aactacgcta ctaacgtcca atacgacggg aaatccggaa ctaacgagtc   5820
aaatggaaac gtttcattcg acttcgtcgg aaggtaatcc atcgccgtcg caagtctcga   5880
cgacttccga atatccgtca caaccgtcgt cgccaccgaa tacgccacgt caatagttac   5940
ttaaaaacat attatcacaa aaggccttga ccaaccgcgg agaatcaaaa taaactctgg   6000
ggcaaataac aatggagttg ccaatcctca aagcaaatgc aattaccaca atcctcgctg   6060
cagtcacatt ttgctttgct tctagtcaaa acatcactga agaattttat caatcaacat   6120
gcagtgcagt tagcaaaggc tatcttagtg ctctaagaac tggttggtat actagtgtta   6180
taactataga attaagtaat atcaagaaaa ataagtgtaa tggaacagat gctaaggtaa   6240
aattgatgaa acaagaatta gataaatata aaaatgctgt aacagaattg cagttgctca   6300
tgcaaagcac accagcagca aacaatcgag ccagaagaga actaccaagg tttatgaatt   6360
atacactcaa caataccaaa aaaaccaatg taacattaag caagaaaagg aaaagaagat   6420
ttcttggttt tttgttaggt gttggatctg caatcgccag tggcattgct gtatctaagg   6480
tcctgcactt agaaggagaa gtgaacaaga tcaaaagtgc tctactatcc acaaacaagg   6540
ccgtagtcag cttatcaaat ggagttagtg tcttaaccag cagagtgtta gacctcaaaa   6600
actatataga taaacaattg ttacctattg tgaataagca aagctgcaga atatcaaata   6660
tagaaactgt gatagagttc caacaaaaga acaacagact actagagatt accagggaat   6720
ttagtgttaa tgcaggtgta actacacctg taagcactta catgttaact aatagtgaat   6780
tattgtcatt aatcaatgat atgcctataa caaatgatca gaaaaagtta atgtccaaca   6840
atgttcaaat agttagacag caaagttact ctatcatgtc cataataaaa gaggaagtct   6900
tagcatatgt agtacaatta ccactatatg gtgtgataga tacaccttgt tggaaattac   6960
acacatcccc tctatgtaca accaacacaa aagaagggtc aaacatctgt ttaacaagaa   7020
ctgacagagg atggtactgt gacaatgcag gatcagtatc tttcttccca caagctgaaa   7080
aatgtaaagt tcaatcgaat cgagtatttt gtgacacaat gtacagttta acattaccaa   7140
gtgaagtaaa tctctgcaat gttgacatat tcaatcccaa atatgattgt aaaattatga   7200
cttcaaaaac agatgtaagc agctccgtta tcacatctct aggagccatt gtgtcatgct   7260
atggcaaaac taaatgtaca gcatccaata aaaatcgtgg aatcataaag acattttcta   7320
acgggtgtga ttatgtatca aataaagggg tggacactgt gtctgtaggt aacacattat   7380
attatgtaaa taagcaagaa ggcaaaagtc tctatgtaaa aggtgaacca ataataaatt   7440
tctatgaccc attagtattc cctctgatg aatttgatgc atcaatatct caagtcaatg   7500
agaagattaa ccagagttta gcatttattc gtaaatccga tgaattatta cataatgtaa   7560
atgctggtaa atcaaccaca aatatcatga taactactat aattatagtg attatagtaa   7620
tattgttatc attaattgct gttggactgc tcctatactg taaggccaga agcacaccag   7680
tcacactaag caaggatcaa ctgagtggta taaataatat tgcatttagt aactgaataa   7740
aaatagcacc taatcatgtt cttacaatgg tttactatct gctcatagac aacccatcta   7800
tcattggatt ttcttaaaat ctgaacttca tcgaaactct tatctataaa ccatctcact   7860
tacactattt aagtagattc ctagtttata gttatataaa acacaattga atgccagtcg   7920
accttaccat ctgtaaaaat gaaaactggg gcaaatatgt cacgaaggaa tccttgcaaa   7980
tttgaaattc gaggtcattg cttaaatggt aagaggtgtc attttagtca taattatttt   8040
gaatggccac cccatgcact gcttgtaaga caaaacttta tgttaaacag aatacttaag   8100
```

```
tctatggata aaagtataga taccttatca gaaataagtg gagctgcaga gttggacaga   8160
acagaagagt atgctcttgg tgtagttgga gtgctagaga gttatatagg atcaataaac   8220
aatataacta aacaatcagc atgtgttgcc atgagcaaac tcctcactga actcaatagt   8280
gatgatatca aaaagctgag ggacaatgaa gagctaaatt cacccaagat aagagtgtac   8340
aatactgtca tatcatatat tgaaagcaac aggaaaaaca ataaacaaac tatccatctg   8400
ttaaaaagat tgccagcaga cgtattgaag aaaaccatca aaaacacatt ggatatccat   8460
aagagcataa ccatcaacaa cccaaaagaa tcaactgtta gtgatacaaa tgaccatgcc   8520
aaaaataatg atactacctg acaaatatcc ttgtagtata acttccatac taataacaag   8580
tagatgtaga gttactatgt ataatcaaaa gaacacacta tatttcaatc aaaacaaccc   8640
aaataaccat atgtactcac cgaatcaaac attcaatgaa atccattgga cctctcaaga   8700
attgattgac acaattcaaa attttctaca acatctaggt attattgagg atatatatac   8760
aatatatata ttagtgtcat aacactcaat tctaacactc accacatcgt tacattatta   8820
attcaaacaa ttcaagttgt gggacaaaat ggatcccatt attaatggaa attctgctaa   8880
tgtttatcta accgatagtt atttaaaagg tgttatctct ttctcagagt gtaatgcttt   8940
aggaagttac atattcaatg gtccttatct caaaaatgat tataccaact taattagtag   9000
acaaaatcca ttaatagaac acatgaatct aaagaaacta aatataacac agtccttaat   9060
atctaagtat cataaaggtg aaataaaatt agaagaacct acttattttc agtcattact   9120
tatgacatac aagagtatga cctcgtcaga acagattgct accactaatt tacttaaaaa   9180
gataataaga agagctatag aaataagtga tgtcaaagtc tatgctatat tgaataaact   9240
agggcttaaa gaaaaggaca agattaaatc caacaatgga caagatgaag acaactcagt   9300
tattacgacc ataatcaaag atgatatact ttcagctgtt aaagataatc aatctcatct   9360
taaagcagac aaaaatcact ctacaaaaca aaaagacaca atcaaaacaa cactcttgaa   9420
gaaattgatg tgttcaatgc aacatcctcc atcatggtta atacattggt ttaacttata   9480
cacaaaatta aacaacatat taacacagta tcgatcaaat gaggtaaaaa accatgggtt   9540
tacattgata gataatcaaa ctcttagtgg atttcaattt attttgaacc aatatggttg   9600
tatagtttat cataaggaac tcaaaagaat tactgtgaca acctataatc aattcttgac   9660
atggaaagat attagcctta gtagattaaa tgtttgttta attacatgga ttagtaactg   9720
cttgaacaca ttaaataaaa gcttaggctt aagatgcgga ttcaataatg ttatcttgac   9780
acaactattc ctttatggag attgtatact aaagctattt cacaatgagg ggttctacat   9840
aataaaagag gtagagggat ttattatgtc tctaatttta aatataacag aagaagatca   9900
attcagaaaa cgattttata atagtatgct caacaacatc acagatgctg ctaataaagc   9960
tcagaaaaat ctgctatcaa gagtatgtca tacattatta gataagacag tgtccgataa  10020
tataataaat ggcagatgga taattctatt aagtaagttc cttaaattaa ttaagcttgc  10080
aggtgacaat aaccttaaca atctgagtga actatatttt ttgttcagaa tatttggaca  10140
cccaatggta gatgaaagac aagccatgga tgctgttaaa attaattgca atgagaccaa  10200
attttacttg ttaagcagtc tgagtatgtt aagaggtgcc tttatatata gaattataaa  10260
agggtttgta aataattaca acagatggcc tactttaaga aatgctattg ttttaccctt  10320
aagatggtta acttactata aactaaacac ttatccttct ttgttggaac ttacagaaag  10380
agatttgatt gtgttatcag gactacgttt ctatcgtgag tttcggttgc ctaaaaaagt  10440
```

```
ggatcttgaa atgattataa atgataaagc tatatcacct cctaaaaatt tgatatggac  10500
tagtttccct agaaattaca tgccatcaca catacaaaac tatatagaac atgaaaaatt  10560
aaaattttcc gagagtgata aatcaagaag agtattagag tattatttaa gagataacaa  10620
attcaatgaa tgtgatttat acaactgtgt agttaatcaa agttatctca acaaccctaa  10680
tcatgtggta tcattgacag gcaaagaaag agaactcagt gtaggtagaa tgtttgcaat  10740
gcaaccggga atgttcagac aggttcaaat attggcagag aaaatgatag ctgaaaacat  10800
tttacaattc tttcctgaaa gtcttacaag atatggtgat ctagaactac aaaaaatatt  10860
agaattgaaa gcaggaataa gtaacaaatc aaatcgctac aatgataatt acaacaatta  10920
cattagtaag tgctctatca tcacagatct cagcaaattc aatcaagcat ttcgatatga  10980
aacgtcatgt atttgtagtg atgtgctgga tgaactgcat ggtgtacaat ctctattttc  11040
ctggttacat ttaactattc ctcatgtcac aataatatgc acatataggc atgcaccccc  11100
ctatatagga gatcatattg tagatcttaa caatgtagat gaacaaagtg gattatatag  11160
atatcacatg ggtggcatcg aagggtggtg tcaaaaactg tggaccatag aagctatatc  11220
actattggat ctaatatctc tcaaagggaa attctcaatt actgctttaa ttaatggtga  11280
caatcaatca atagatataa gcaaaccaat cagactcatg gaaggtcaaa ctcatgctca  11340
agcagattat ttgctagcat taaatagcct taaattactg tataaagagt atgcaggcat  11400
aggccacaaa ttaaaaggaa ctgagactta tatatcacga gatatgcaat ttatgagtaa  11460
aacaattcaa cataacggtg tatattaccc agctagtata aagaaagtcc taagagtggg  11520
accgtggata aacactatac ttgatgattt caaagtgagt ctagaatcta taggtagttt  11580
gacacaagaa ttagaatata gaggtgaaag tctattatgc agtttaatat ttagaaatgt  11640
atggttatat aatcagattg ctctacaatt aaaaaatcat gcattatgta acaataaact  11700
atatttggac atattaaagg ttctgaaaca cttaaaaacc ttttttaatc ttgataatat  11760
tgatacagca ttaacattgt atatgaattt acccatgtta tttggtggtg gtgatcccaa  11820
cttgttatat cgaagtttct atagaagaac tcctgacttc ctcacagagg ctatagttca  11880
ctctgtgttc atacttagtt attatacaaa ccatgactta aaagataaac ttcaagatct  11940
gtcagatgat agattgaata agttcttaac atgcataatc acgtttgaca aaaaccctaa  12000
tgctgaattc gtaacattga tgagagatcc tcaagcttta gggtctgaga gacaagctaa  12060
aattactagc gaaatcaata gactggcagt tacagaggtt ttgagtacag ctccaaacaa  12120
aatattctcc aaaagtgcac aacattatac tactacagag atagatctaa atgatattat  12180
gcaaaatata gaacctacat atcctcatgg gctaagagtt gtttatgaaa gtttaccctt  12240
ttataaagca gagaaaatag taaatcttat atcaggtaca aaatctataa ctaacatact  12300
ggaaaaaact tctgccatag acttaacaga tattgataga gccactgaga tgatgaggaa  12360
aaacataact ttgcttataa ggatacttcc attggattgt aacagagata aaagagagat  12420
attgagtatg gaaaacctaa gtattactga attaagcaaa tatgttaggg aaagatcttg  12480
gtctttatcc aatatagttg gtgttacatc acccagtatc atgtatacaa tggacatcaa  12540
atatactaca agcactatat ctagtggcat aattatagag aaatataatg ttaacagttt  12600
aacacgtggt gagagaggac ccactaaacc atgggttggt tcatctacac aagagaaaaa  12660
aacaatgcca gtttataata gacaagtctt aaccaaaaaa cagagagatc aaatagatct  12720
attagcaaaa ttggattggg tgtatgcatc tatagataac aaggatgaat tcatggaaga  12780
actcagcata ggaacccttg ggttaacata tgaaaaggcc aagaaattat ttccacaata  12840
```

```
tttaagtgtc aattatttgc atcgccttac agtcagtagt agaccatgtg aattccctgc  12900
atcaatacca gcttatagaa caacaaatta tcactttgac actagcccta ttaatcgcat  12960
attaacagaa aagtatggtg atgaagatat tgacatagta ttccaaaact gtataagctt  13020
tggccttagt ttaatgtcag tagtagaaca atttactaat gtatgtccta acagaattat  13080
tctcatacct aagcttaatg agatacattt gatgaaacct cccatattca caggtgatgt  13140
tgatattcac aagttaaaac aagtgataca aaaacagcat atgtttttac cagacaaaat  13200
aagtttgact caatatgtgg aattattctt aagtaataaa acactcaaat ctggatctca  13260
tgttaattct aatttaatat tggcacataa aatatctgac tattttcata atacttacat  13320
tttaagtact aatttagctg gacattggat tctgattata caacttatga aagattctaa  13380
aggtattttt gaaaaagatt ggggagaggg atatataact gatcatatgt ttattaattt  13440
gaaagttttc ttcaatgctt ataagaccta tctcttgtgt tttcataaag gttatggcaa  13500
agcaaagctg gagtgtgata tgaacacttc agatcttcta tgtgtattgg aattaataga  13560
cagtagttat tggaagtcta tgtctaaggt atttttagaa caaaaagtta tcaaatacat  13620
tcttagccaa gatgcaagtt tacatagagt aaaaggatgt catagcttca aattatggtt  13680
tcttaaacgt cttaatgtag cagaattcac agtttgccct tgggttgtta acatagatta  13740
tcatccaaca catatgaaag caatattaac ttatatagat cttgttagaa tgggattgat  13800
aaatatagat agaatacaca ttaaaaataa acacaaattc aatgatgaat tttatacttc  13860
taatctcttc tacattaatt ataacttctc agataatact catctattaa ctaaacatat  13920
aaggattgct aattctgaat tagaaaataa ttacaacaaa ttatatcatc ctacaccaga  13980
aaccctagag aatatactag ccaatccgat taaaagtaat gacaaaaaga cactgaatga  14040
ctattgtata ggtaaaaatg ttgactcaat aatgttacca ttgttatcta ataagaagct  14100
tattaaatcg tctgcaatga ttagaaccaa ttacagcaaa caagatttgt ataatttatt  14160
ccctatggtt gtgattgata gaattataga tcattcaggc aatacagcca aatccaacca  14220
actttacact actacttccc accaaatatc tttagtgcac aatagcacat cactttactg  14280
catgcttcct tggcatcata ttaatagatt caattttgta tttagttcta caggttgtaa  14340
aattagtata gagtatattt taaaagatct taaaattaaa gatcccaatt gtatagcatt  14400
cataggtgaa ggagcaggga atttattatt gcgtacagta gtggaacttc atcctgacat  14460
aagatatatt tacagaagtc tgaaagattg caatgatcat agtttaccta ttgagttttt  14520
aaggctgtac aatggacata tcaacattga ttatggtgaa aatttgacca ttcctgctac  14580
agatgcaacc aacaacattc attggtctta tttacatata aagtttgctg aacctatcag  14640
tctttttgtc tgtgatgccg aattgtctgt aacagtcaac tggagtaaaa ttataataga  14700
atggagcaag catgtaagaa agtgcaagta ctgttcctca gttaataaat gtatgttaat  14760
agtaaaatat catgctcaag atgatattga tttcaaatta gacaatataa ctatattaaa  14820
aacttatgta tgcttaggca gtaagttaaa gggatcggag gtttacttag tccttacaat  14880
aggtcctgcg aatatattcc cagtatttaa tgtagtacaa aatgctaaat tgatactatc  14940
aagaaccaaa aatttcatca tgcctaagaa agctgataaa gagtctattg atgcaaatat  15000
taaaagtttg ataccctttc tttgttaccc tataacaaaa aaaggaatta atactgcatt  15060
gtcaaaacta aagagtgttg ttagtggaga tatactatca tattctatag ctggacgtaa  15120
tgaagttttc agcaataaac ttataaatca taagcatatg aacatcttaa aatggttcaa  15180
```

tcatgtttta aatttcagat caacagaact aaactataac catttatata tggtagaatc 15240
tacatatcct tacctaagtg aattgttaaa cagcttgaca accaatgaac ttaaaaaact 15300
gattaaaatc acaggtagtc tgttatacaa ctttcataat gaataatgaa taaagatctt 15360
ataataaaaa ttcccatagc tatacactaa cactgtattc aattatagtt attaaaaatt 15420
aaaaatcgta cgatttttta aataactttt agtgaactaa tcctaaagtt atcattttaa 15480
tcttggagga ataaatttaa accctaatct aattggttta tatgtgtatt aactaaatta 15540
cgagatatta gtttttgaca cttttttct cgt 15573

<210> SEQ ID NO 4
<211> LENGTH: 15573
<212> TYPE: DNA
<213> ORGANISM: respiratory syncytial virus

<400> SEQUENCE: 4
acgcgaaaaa atgcgtacaa caaacttgca taaaccaaaa aaatggggca aataagaatt 60
tgataagtac cacttaaatt taactccctt gcttagcgat ggtgagcgag ctgattaagg 120
agaacatgca catgaagctg tacatggagg gcaccgtgaa caaccaccac ttcaagtgca 180
catccgaggg cgaaggcaag ccctacgagg gcacccagac catgagaatc aaggcggtcg 240
agggcggccc tctccccttc gccttcgaca tcctggctac cagcttcatg tacggcagca 300
aaaccttcat caaccacacc cagggcatcc ccgacttctt taagcagtcc ttccccgagg 360
gcttcacatg ggagagagtc accacatacg aagacggggg cgtgctgacc gctacccagg 420
acaccagcct ccaggacggc tgcctcatct acaacgtcaa gatcagaggg gtgaacttcc 480
catccaacgg ccctgtgatg cagaagaaaa cactcggctg ggaggcctcc accgagaccc 540
tgtaccccgc tgacggcggc ctggaaggca gagccgacat ggccctgaag ctcgtgggcg 600
ggggccacct gatctgcaac ttgaagacca catacagatc caagaaaccc gctaagaacc 660
tcaagatgcc cggcgtctac tatgtggaca gaagactgga aagaatcaag gaggccgaca 720
aagagaccta cgtcgagcag cacgaggtgg ctgtggccag atactgcgac ctccctagca 780
aactggggca cagatgagta ttcaattata gttattaaaa acttaacaga agacaaaaat 840
ggggcaaata agaatttgat aagtaccact taaatttaac tcccttgctt agcgatgggt 900
tcgaattcgc tatcgatgat aaaagtacgt ctacaaaatc tatttgataa tgatgaagta 960
gcgctactaa aaataacgtg ttatacggat aaactaatac atctaacgaa tgcgctagcg 1020
aaagcggtaa tacatacgat aaaactaaat ggtatagtat ttgtacatgt aataacgtcg 1080
tcggatatat gtccgaataa taatatagta gtaaaatcga attttacgac gatgccggta 1140
ctacaaaatg gtggttatat atgggaaatg atggaactaa cgcattgttc gcaaccgaat 1200
ggtctactag atgataattg tgaaataaaa ttttcgaaaa aactatcgga ttcgacgatg 1260
acgaattata tgaatcaact atcggaacta ctaggttttg atctaaatcc gtaaattata 1320
attaatatca actagcaaat caatgtcact aacaccatta gttaatataa aacttaacag 1380
aagacaaaaa tggggcaaat aaatcaattc agccaaccca accatggata cgacgcataa 1440
tgataatacg ccgcaacgtc taatgataac ggatatgcgt ccgctatcgc tagaaacgat 1500
aataacgtcg ctaacgcgtg atataataac gcataaattt atatatctaa taaatcatga 1560
atgtatagta cgtaaactag atgaacgtca agcgacgttt acgtttctag taaattatga 1620
aatgaaacta ctacataaag taggttcgac gaaatataaa aaatatacgg aatataatac 1680
gaaatatggt acgtttccga tgccgatatt tataaatcat gatggttttc tagaatgtat 1740

```
aggtataaaa ccgacgaaac atacgccgat aatatataaa tatgatctaa atccgtaaat   1800
ttcaacacaa tattcacaca atctaaaaca acaactctat gcataactat actccatagt   1860
ccagatggag cctgaaaatt atagtaattt aaaattaagg agagatataa gatagaagat   1920
ggggcaaata caaagatggc tcttagcaaa gtcaagttga atgatacact caacaaagat   1980
caacttctgt catccagcaa atacaccatc caacggagca caggagatag tattgatact   2040
cctaattatg atgtgcagaa acacatcaat aagttatgtg gcatgttatt aatcacagaa   2100
gatgctaatc ataaattcac tgggttaata ggtatgttat atgcgatgtc taggttagga   2160
agagaagaca ccataaaaat actcagagat gcgggatatc atgtaaaagc aaatggagta   2220
gatgtaacaa cacatcgtca agacattaat ggaaaagaaa tgaaatttga agtgttaaca   2280
ttggcaagct taacaactga aattcaaatc aacattgaga tagaatctag aaaatcctac   2340
aaaaaaatgc taaaagaaat gggagaggta gctccagaat acaggcatga ctctcctgat   2400
tgtgggatga taatattatg tatagcagca ttagtaataa ctaaattagc agcaggggac   2460
agatctggtc ttacagccgt gattaggaga gctaataatg tcctaaaaaa tgaaatgaaa   2520
cgttacaaag gcttactacc caaggacata gccaacagct tctatgaagt gtttgaaaaa   2580
catccccact ttatagatgt ttttgttcat tttggtatag cacaatcttc taccagaggt   2640
ggcagtagag ttgaagggat ttttgcagga ttgtttatga atgcctatgg tgcagggcaa   2700
gtgatgttac ggtggggagt cttagcaaaa tcagttaaaa atattatgtt aggacatgct   2760
agtgtgcaag cagaaatgga acaagttgtt gaggtttatg aatatgccca aaaattgggt   2820
ggtgaagcag gattctacca tatattgaac aacccaaaag catcattatt atctttgact   2880
caatttcctc acttctccag tgtagtatta ggcaatgctg ctggcctagg cataatggga   2940
gagtacagag gtacaccgag gaatcaagat ctatatgatg cagcaaaggc atatgctgaa   3000
caactcaaag aaaatggtgt gattaactac agtgtactag acttgacagc agaagaacta   3060
gaggctatca aacatcagct taatccaaaa gataatgatg tagagctttg agttaataaa   3120
aaatggggca aataaatcat catggaaaag tttgctcctg aattccatgg agaagatgca   3180
aacaacaggg ctactaaatt cctagaatca ataaagggca aattcacatc acccaaagat   3240
cccaagaaaa aagatagtat catatctgtc aactcaatag atatagaagt aaccaaagaa   3300
agccctataa catcaaattc aactattatc aacccaacaa atgagacaga tgatactgca   3360
gggaacaagc ccaattatca aagaaaacct ctagtaagtt tcaaagaaga ccctacacca   3420
agtgataatc ccttttctaa actatacaaa gaaaccatag aaacatttga taacaatgaa   3480
gaagaatcca gctattcata cgaagaaata aatgatcaga caaacgataa tataacagca   3540
agattagata ggattgatga aaaattaagt gaaatactag gaatgcttca cacattagta   3600
gtggcaagtg caggacctac atctgctcgg gatggtataa gagatgccat gattggttta   3660
agagaagaaa tgatagaaaa aatcagaact gaagcattaa tgaccaatga cagattagaa   3720
gctatggcaa gactcaggaa tgaggaaagt gaaaagatgg caaaagacac atcagatgaa   3780
gtgtctctca atccaacatc agagaaattg aacaacctat tggaagggaa tgatagtgac   3840
aatgatctat cacttgaaga tttctgatta gttaccactc ttcacatcaa cacacaatac   3900
caacagaaga ccaacaaact aaccaaccca atcatccaac caaacatcca tccgccaatc   3960
agccaaacag ccaacaaaac aaccagccaa tccaaaacta accacccgga aaaaatctat   4020
aatatagtta caaaaaaagg aaagggtggg gcaaatatgg aaacatacgt gaacaagctt   4080
```

```
cacgaaggct ccacatacac agctgctgtt caatacaatg tcttagaaaa agacgatgac   4140
cctgcatcac ttacaatatg ggtgcccatg ttccaatcat ctatgccagc agatttactt   4200
ataaaagaac tagctaatgt caacatacta gtgaaacaaa tatccacacc caagggacct   4260
tcactaagag tcatgataaa ctcaagaagt gcagtgctag cacaaatgcc cagcaaattt   4320
accatatgcg ctaatgtgtc cttggatgaa agaagcaaac tagcatatga tgtaaccaca   4380
ccctgtgaaa tcaaggcatg tagtctaaca tgcctaaaat caaaaaatat gttgactaca   4440
gttaaagatc tcactatgaa gacactcaac cctacacatg atattattgc tttatgtgaa   4500
tttgaaaaca tagtaacatc aaaaaaagtc ataataccaa catacctaag atccatcagt   4560
gtcagaaata aagatctgaa cacacttgaa aatataacaa ccactgaatt caaaaatgct   4620
atcacaaatg caaaaatcat cccttactca ggattactat tagtcatcac agtgactgac   4680
aacaaaggag cattcaaata cataaagcca caaagtcaat tcatagtaga tcttggagct   4740
tacctagaaa aagaaagtat atattatgtt accacaaatt ggaagcacac agctacacga   4800
tttgcaatca aacccatgga agattaacct ttttcctcta catcagtgtg ttaattcata   4860
caaactttct acctacattc ttcacttcac catcacaatc acaaacactc tgtggttcaa   4920
ccaatcaaac aaaacttatc tgaagtccca gatcatccca agtcattgtt tatcagatct   4980
agtactcaaa taagttaata aaaaatatac acatggacgt ccatggggca aatgcaaaca   5040
tgtcgaaaaa taaagatcaa cgtacggcga aaacgctaga acgtacgtgg gatacgctaa   5100
atcatctact atttatatcg tcgtgtctat ataaactaaa tctaaaatcg gtagcgcaaa   5160
taacgctatc gatactagcg ataataatat cgacttcgct aataatagcg gcgataatat   5220
ttatagcgtc ggcgaatcat aaagtaacgc cgacgacggc gataatacaa gatgcgactt   5280
cgcaaataaa aaatacgacg ccgacgtatc taacgcaaaa tccgcaacta ggtatatcgc   5340
cgtcgaatcc gtcggaaata acgtcgcaaa taacgacgat actagcgtcg acgacgccgg   5400
gtgtaaaatc gacgctacaa tcgacgacgg taaaaacgaa aaatacgacg acgacgcaaa   5460
cgcaaccgtc gaaaccgacg acgaaacaac gtcaaaataa accgccgtcg aaaccgaata   5520
atgattttca ttttgaagta tttaattttg taccgtgttc gatatgttcg aataatccga   5580
cgtgttgggc gatatgtaaa cgtataccga ataaaaaacc gggtaaaaaa acgacgacga   5640
aaccgacgaa aaaaccgacg ctaaaaacga cgaaaaaaga tccgaaaccg caaacgacga   5700
aatcgaaaga agtaccgacg acgaaaccga cggaagaacc gacgataaat acgacgaaaa   5760
cgaatataat aacgacgcta ctaacgtcga atacgacggg taatccggaa ctaacgtcgc   5820
aaatggaaac gtttcattcg acttcgtcgg aaggtaatcc gtcgccgtcg caagtatcga   5880
cgacttcgga atatccgtcg caaccgtcgt cgccgccgaa tacgccgcgt caatagttac   5940
ttaaaaacat attatcacaa aaggccttga ccaaccgcgg agaatcaaaa taaactctgg   6000
ggcaaataac aatggagttg ccaatcctca aagcaaatgc aattaccaca atcctcgctg   6060
cagtcacatt ttgctttgct tctagtcaaa acatcactga agaattttat caatcaacat   6120
gcagtgcagt tagcaaaggc tatcttagtg ctctaagaac tggttggtat actagtgtta   6180
taactataga attaagtaat atcaagaaaa ataagtgtaa tggaacagat gctaaggtaa   6240
aattgatgaa acaagaatta gataaatata aaaatgctgt aacagaattg cagttgctca   6300
tgcaaagcac accagcagca aacaatcgag ccagaagaga actaccaagg tttatgaatt   6360
atacactcaa caataccaaa aaaaccaatg taacattaag caagaaaagg aaaagaagat   6420
ttcttggttt tttgttaggt gttggatctg caatcgccag tggcattgct gtatctaagg   6480
```

```
tcctgcactt agaaggagaa gtgaacaaga tcaaaagtgc tctactatcc acaaacaagg   6540
ccgtagtcag cttatcaaat ggagttagtg tcttaaccag cagagtgtta gacctcaaaa   6600
actatataga taaacaattg ttacctattg tgaataagca aagctgcaga atatcaaata   6660
tagaaactgt gatagagttc caacaaaaga acaacagact actagagatt accagggaat   6720
ttagtgttaa tgcaggtgta actacacctg taagcactta catgttaact aatagtgaat   6780
tattgtcatt aatcaatgat atgcctataa caaatgatca gaaaaagtta atgtccaaca   6840
atgttcaaat agttagacag caaagttact ctatcatgtc cataataaaa gaggaagtct   6900
tagcatatgt agtacaatta ccactatatg gtgtgataga tacaccttgt tggaaattac   6960
acacatcccc tctatgtaca accaacacaa aagaagggtc aaacatctgt ttaacaagaa   7020
ctgacagagg atggtactgt gacaatgcag gatcagtatc tttcttccca caagctgaaa   7080
aatgtaaagt tcaatcgaat cgagtatttt gtgacacaat gtacagttta acattaccaa   7140
gtgaagtaaa tctctgcaat gttgacatat tcaatcccaa atatgattgt aaaattatga   7200
cttcaaaaac agatgtaagc agctccgtta tcacatctct aggagccatt gtgtcatgct   7260
atggcaaaac taaatgtaca gcatccaata aaaatcgtgg aatcataaag acattttcta   7320
acgggtgtga ttatgtatca aataaagggg tggacactgt gtctgtaggt aacacattat   7380
attatgtaaa taagcaagaa ggcaaaagtc tctatgtaaa aggtgaacca ataataaatt   7440
tctatgaccc attagtattc ccctctgatg aatttgatgc atcaatatct caagtcaatg   7500
agaagattaa ccagagttta gcatttattc gtaaatccga tgaattatta cataatgtaa   7560
atgctggtaa atcaaccaca aatatcatga taactactat aattatagtg attatagtaa   7620
tattgttatc attaattgct gttggactgc tcctatactg taaggccaga agcacaccag   7680
tcacactaag caaggatcaa ctgagtggta taaataatat tgcatttagt aactgaataa   7740
aaatagcacc taatcatgtt cttacaatgg tttactatct gctcatagac aacccatcta   7800
tcattggatt ttcttaaaat ctgaacttca tcgaaactct tatctataaa ccatctcact   7860
tacactattt aagtagattc ctagtttata gttatataaa acacaattga atgccagtcg   7920
accttaccat ctgtaaaaat gaaaactggg gcaaatatgt cacgaaggaa tccttgcaaa   7980
tttgaaattc gaggtcattg cttaaatggt aagaggtgtc attttagtca taattatttt   8040
gaatggccac cccatgcact gcttgtaaga caaaacttta tgttaaacag aatacttaag   8100
tctatggata aaagtataga taccttatca gaaataagtg gagctgcaga gttggacaga   8160
acagaagagt atgctcttgg tgtagttgga gtgctagaga gttatatagg atcaataaac   8220
aatataacta aacaatcagc atgtgttgcc atgagcaaac tcctcactga actcaatagt   8280
gatgatatca aaaagctgag ggacaatgaa gagctaaatt cacccaagat aagagtgtac   8340
aatactgtca tatcatatat tgaaagcaac aggaaaaaca ataaacaaac tatccatctg   8400
ttaaaaagat tgccagcaga cgtattgaag aaaaccatca aaaacacatt ggatatccat   8460
aagagcataa ccatcaacaa cccaaaagaa tcaactgtta gtgatacaaa tgaccatgcc   8520
aaaaataatg atactacctg acaaatatcc ttgtagtata acttccatac taataacaag   8580
tagatgtaga gttactatgt ataatcaaaa gaacacacta tatttcaatc aaaacaaccc   8640
aaataaccat atgtactcac cgaatcaaac attcaatgaa atccattgga cctctcaaga   8700
attgattgac acaattcaaa attttctaca acatctaggt attattgagg atatatatac   8760
aatatatata ttagtgtcat aacactcaat tctaacactc accacatcgt tacattatta   8820
```

```
attcaaacaa ttcaagttgt gggacaaaat ggatcccatt attaatggaa attctgctaa   8880
tgtttatcta accgatagtt atttaaaagg tgttatctct ttctcagagt gtaatgcttt   8940
aggaagttac atattcaatg gtccttatct caaaaatgat tataccaact taattagtag   9000
acaaaatcca ttaatagaac acatgaatct aaagaaacta aatataacac agtccttaat   9060
atctaagtat cataaaggtg aaataaaatt agaagaacct acttattttc agtcattact   9120
tatgacatac aagagtatga cctcgtcaga acagattgct accactaatt tacttaaaaa   9180
gataataaga agagctatag aaataagtga tgtcaaagtc tatgctatat tgaataaact   9240
agggcttaaa gaaaaggaca agattaaatc caacaatgga caagatgaag acaactcagt   9300
tattacgacc ataatcaaag atgatatact ttcagctgtt aaagataatc aatctcatct   9360
taaagcagac aaaaatcact ctacaaaaca aaaagacaca atcaaaacaa cactcttgaa   9420
gaaattgatg tgttcaatgc aacatcctcc atcatggtta atacattggt ttaacttata   9480
cacaaaatta aacaacatat taacacagta tcgatcaaat gaggtaaaaa accatgggtt   9540
tacattgata gataatcaaa ctcttagtgg atttcaattt attttgaacc aatatggttg   9600
tatagtttat cataaggaac tcaaaagaat tactgtgaca acctataatc aattcttgac   9660
atggaaagat attagcctta gtagattaaa tgtttgttta attacatgga ttagtaactg   9720
cttgaacaca ttaaataaaa gcttaggctt aagatgcgga ttcaataatg ttatcttgac   9780
acaactattc ctttatggag attgtatact aaagctattt cacaatgagg ggttctacat   9840
aataaaagag gtagagggat ttattatgtc tctaatttta aatataacag aagaagatca   9900
attcagaaaa cgattttata atagtatgct caacaacatc acagatgctg ctaataaagc   9960
tcagaaaaat ctgctatcaa gagtatgtca tacattatta gataagacag tgtccgataa  10020
tataataaat ggcagatgga taattctatt aagtaagttc cttaaattaa ttaagcttgc  10080
aggtgacaat aaccttaaca atctgagtga actatatttt ttgttcagaa tatttggaca  10140
cccaatggta gatgaaagac aagccatgga tgctgttaaa attaattgca atgagaccaa  10200
attttacttg ttaagcagtc tgagtatgtt aagaggtgcc tttatatata gaattataaa  10260
agggtttgta aataattaca acagatggcc tactttaaga aatgctattg ttttaccctt  10320
aagatggtta acttactata aactaaacac ttatccttct ttgttggaac ttacagaaag  10380
agatttgatt gtgttatcag gactacgttt ctatcgtgag tttcggttgc ctaaaaaagt  10440
ggatcttgaa atgattataa atgataaagc tatatcacct cctaaaaatt tgatatggac  10500
tagtttccct agaaattaca tgccatcaca catacaaaac tatatagaac atgaaaaatt  10560
aaaattttcc gagagtgata aatcaagaag agtattagag tattatttaa gagataacaa  10620
attcaatgaa tgtgatttat acaactgtgt agttaatcaa agttatctca acaaccctaa  10680
tcatgtggta tcattgacag gcaaagaaag agaactcagt gtaggtagaa tgtttgcaat  10740
gcaaccggga atgttcagac aggttcaaat attggcagag aaaatgatag ctgaaaacat  10800
tttacaattc tttcctgaaa gtcttacaag atatggtgat ctagaactac aaaaaatatt  10860
agaattgaaa gcaggaataa gtaacaaatc aaatcgctac aatgataatt acaacaatta  10920
cattagtaag tgctctatca tcacagatct cagcaaattc aatcaagcat ttcgatatga  10980
aacgtcatgt atttgtagtg atgtgctgga tgaactgcat ggtgtacaat ctctattttc  11040
ctggttacat ttaactattc ctcatgtcac aataatatgc acatataggc atgcaccccc  11100
ctatatagga gatcatattg tagatcttaa caatgtagat gaacaaagtg gattatatag  11160
atatcacatg ggtggcatcg aagggtggtg tcaaaaactg tggaccatag aagctatatc  11220
```

```
actattggat ctaatatctc tcaaagggaa attctcaatt actgctttaa ttaatggtga  11280
caatcaatca atagatataa gcaaaccaat cagactcatg gaaggtcaaa ctcatgctca  11340
agcagattat ttgctagcat taaatagcct taaattactg tataaagagt atgcaggcat  11400
aggccacaaa ttaaaaggaa ctgagactta tatatcacga gatatgcaat ttatgagtaa  11460
aacaattcaa cataacggtg tatattaccc agctagtata aagaaagtcc taagagtggg  11520
accgtggata aacactatac ttgatgattt caaagtgagt ctagaatcta taggtagttt  11580
gacacaagaa ttagaatata gaggtgaaag tctattatgc agtttaatat ttagaaatgt  11640
atggttatat aatcagattg ctctacaatt aaaaaatcat gcattatgta acaataaact  11700
atatttggac atattaaagg ttctgaaaca cttaaaaacc ttttttaatc ttgataatat  11760
tgatacagca ttaacattgt atatgaattt acccatgtta tttggtggtg gtgatcccaa  11820
cttgttatat cgaagtttct atagaagaac tcctgacttc ctcacagagg ctatagttca  11880
ctctgtgttc atacttagtt attatacaaa ccatgactta aaagataaac ttcaagatct  11940
gtcagatgat agattgaata agttcttaac atgcataatc acgtttgaca aaaaccctaa  12000
tgctgaattc gtaacattga tgagagatcc tcaagcttta gggtctgaga gacaagctaa  12060
aattactagc gaaatcaata gactggcagt tacagaggtt ttgagtacag ctccaaacaa  12120
aatattctcc aaaagtgcac aacattatac tactacagag atagatctaa atgatattat  12180
gcaaaatata gaacctacat atcctcatgg gctaagagtt gtttatgaaa gtttaccctt  12240
ttataaagca gagaaaatag taaatcttat atcaggtaca aaatctataa ctaacatact  12300
ggaaaaaact tctgccatag acttaacaga tattgataga gccactgaga tgatgaggaa  12360
aaacataact ttgcttataa ggatacttcc attggattgt aacagagata aaagagagat  12420
attgagtatg gaaaacctaa gtattactga attaagcaaa tatgttaggg aaagatcttg  12480
gtctttatcc aatatagttg gtgttacatc acccagtatc atgtatacaa tggacatcaa  12540
atatactaca agcactatat ctagtggcat aattatagag aaatataatg ttaacagttt  12600
aacacgtggt gagagaggac ccactaaacc atgggttggt tcatctacac aagagaaaaa  12660
aacaatgcca gtttataata gacaagtctt aaccaaaaaa cagagagatc aaatagatct  12720
attagcaaaa ttggattggg tgtatgcatc tatagataac aaggatgaat tcatggaaga  12780
actcagcata ggaacccttg ggttaacata tgaaaaggcc aagaaattat ttccacaata  12840
tttaagtgtc aattatttgc atcgccttac agtcagtagt agaccatgtg aattccctgc  12900
atcaatacca gcttatagaa caacaaatta tcactttgac actagcccta ttaatcgcat  12960
attaacagaa aagtatggtg atgaagatat tgacatagta ttccaaaact gtataagctt  13020
tggccttagt ttaatgtcag tagtagaaca atttactaat gtatgtccta acagaattat  13080
tctcatacct aagcttaatg agatacattt gatgaaacct cccatattca caggtgatgt  13140
tgatattcac aagttaaaac aagtgataca aaaacagcat atgtttttac cagacaaaat  13200
aagtttgact caatatgtgg aattattctt aagtaataaa acactcaaat ctggatctca  13260
tgttaattct aatttaatat tggcacataa aatatctgac tattttcata atacttacat  13320
tttaagtact aatttagctg gacattggat tctgattata caacttatga aagattctaa  13380
aggtattttt gaaaaagatt ggggagaggg atatataact gatcatatgt ttattaattt  13440
gaaagttttc ttcaatgctt ataagaccta tctcttgtgt tttcataaag gttatggcaa  13500
agcaaagctg gagtgtgata tgaacacttc agatcttcta tgtgtattgg aattaataga  13560
```

```
cagtagttat tggaagtcta tgtctaaggt atttttagaa caaaaagtta tcaaatacat  13620

tcttagccaa gatgcaagtt tacatagagt aaaaggatgt catagcttca aattatggtt  13680

tcttaaacgt cttaatgtag cagaattcac agtttgccct tgggttgtta acatagatta  13740

tcatccaaca catatgaaag caatattaac ttatatagat cttgttagaa tgggattgat  13800

aaatatagat agaatacaca ttaaaaataa acacaaattc aatgatgaat tttatacttc  13860

taatctcttc tacattaatt ataacttctc agataatact catctattaa ctaaacatat  13920

aaggattgct aattctgaat tagaaaataa ttacaacaaa ttatatcatc ctacaccaga  13980

aaccctagag aatatactag ccaatccgat taaaagtaat gacaaaaaga cactgaatga  14040

ctattgtata ggtaaaaatg ttgactcaat aatgttacca ttgttatcta ataagaagct  14100

tattaaatcg tctgcaatga ttagaaccaa ttacagcaaa caagatttgt ataatttatt  14160

ccctatggtt gtgattgata gaattataga tcattcaggc aatacagcca aatccaacca  14220

actttacact actacttccc accaaatatc tttagtgcac aatagcacat cactttactg  14280

catgcttcct tggcatcata ttaatagatt caattttgta tttagttcta caggttgtaa  14340

aattagtata gagtatattt taaaagatct taaaattaaa gatcccaatt gtatagcatt  14400

cataggtgaa ggagcaggga atttattatt gcgtacagta gtggaacttc atcctgacat  14460

aagatatatt tacagaagtc tgaaagattg caatgatcat agtttaccta ttgagttttt  14520

aaggctgtac aatggacata tcaacattga ttatggtgaa aatttgacca ttcctgctac  14580

agatgcaacc aacaacattc attggtctta tttacatata aagtttgctg aacctatcag  14640

tctttttgtc tgtgatgccg aattgtctgt aacagtcaac tggagtaaaa ttataataga  14700

atggagcaag catgtaagaa agtgcaagta ctgttcctca gttaataaat gtatgttaat  14760

agtaaaatat catgctcaag atgatattga tttcaaatta gacaatataa ctatattaaa  14820

aacttatgta tgcttaggca gtaagttaaa gggatcggag gtttacttag tccttacaat  14880

aggtcctgcg aatatattcc cagtatttaa tgtagtacaa aatgctaaat tgatactatc  14940

aagaaccaaa aatttcatca tgcctaagaa agctgataaa gagtctattg atgcaaatat  15000

taaaagtttg ataccctttc tttgttaccc tataacaaaa aaaggaatta atactgcatt  15060

gtcaaaacta aagagtgttg ttagtggaga tatactatca tattctatag ctggacgtaa  15120

tgaagttttc agcaataaac ttataaatca taagcatatg aacatcttaa aatggttcaa  15180

tcatgtttta aatttcagat caacagaact aaactataac catttatata tggtagaatc  15240

tacatatcct tacctaagtg aattgttaaa cagcttgaca accaatgaac ttaaaaaact  15300

gattaaaatc acaggtagtc tgttatacaa ctttcataat gaataatgaa taaagatctt  15360

ataataaaaa ttcccatagc tatacactaa cactgtattc aattatagtt attaaaaatt  15420

aaaaatcgta cgatttttta aataactttt agtgaactaa tcctaaagtt atcattttaa  15480

tcttggagga ataaatttaa accctaatct aattggttta tatgtgtatt aactaaatta  15540

cgagatatta gtttttgaca cttttttct cgt                                15573
```

<210> SEQ ID NO 5
<211> LENGTH: 139
<212> TYPE: PRT
<213> ORGANISM: respiratory syncytial virus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature

```
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (64)..(65)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (92)..(93)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (104)..(106)
<223> OTHER INFORMATION: Xaa can be any naturally occurring amino acid
<220> FEATURE:
<221> NAME/KEY: misc_feature
<222> LOCATION: (115)..(116)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
```

```
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (126)..(127)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (138)..(139)
<223> OTHER INFORMATION: Xaa can be any naturally occurring amino acid

<400> SEQUENCE: 5

Met Gly Xaa Asn Xaa Leu Ser Xaa Ile Lys Xaa Arg Leu Gln Asn Leu
1               5                   10                  15

Xaa Xaa Asn Asp Glu Val Ala Leu Leu Lys Ile Thr Cys Tyr Xaa Asp
            20                  25                  30

Lys Leu Ile Xaa Leu Thr Asn Ala Leu Ala Lys Ala Xaa Ile His Thr
        35                  40                  45

Ile Lys Leu Asn Gly Ile Val Phe Xaa His Val Ile Thr Ser Ser Xaa
    50                  55                  60

Xaa Cys Pro Xaa Asn Xaa Ile Val Val Lys Ser Asn Phe Thr Thr Met
65                  70                  75                  80

Pro Xaa Leu Xaa Asn Gly Gly Tyr Ile Xaa Glu Xaa Xaa Glu Leu Thr
                85                  90                  95

His Cys Ser Gln Xaa Asn Gly Xaa Xaa Xaa Asp Asn Cys Glu Ile Lys
            100                 105                 110

Phe Ser Xaa Xaa Leu Xaa Asp Ser Xaa Met Thr Xaa Tyr Xaa Xaa Gln
        115                 120                 125

Xaa Ser Xaa Leu Leu Gly Xaa Asp Leu Xaa Xaa
    130                 135


<210> SEQ ID NO 6
<211> LENGTH: 420
<212> TYPE: DNA
<213> ORGANISM: respiratory syncytial virus

<400> SEQUENCE: 6

atgggttcga attcgctatc gatgataaaa gtacgtctac aaaatctatt tgataatgat      60

gaagtagcgc tactaaaaat aacgtgttat acggataaac taatacatct aacgaatgcg     120

ctagcgaaag cggtaataca tacgataaaa ctaaatggta tagtatttgt acatgtaata     180

acgtcgtcgg atatatgtcc gaataataat atagtagtaa aatcgaattt tacgacgatg     240

ccggtactac aaaatggtgg ttatatatgg gaaatgatgg aactaacgca ttgttcgcaa     300

ccgaatggtc tactagatga taattgtgaa ataaaatttt cgaaaaaact atcggattcg     360

acgatgacga attatatgaa tcaactatcg gaactactag gttttgatct aaatccgtaa     420


<210> SEQ ID NO 7
<211> LENGTH: 420
<212> TYPE: DNA
```

<213> ORGANISM: respiratory syncytial virus

<400> SEQUENCE: 7

```
atggggtcga actcgctctc gatgatcaag gtccgcctcc agaatctctt cgacaacgac     60
gaggtcgcgc tcctcaagat cacgtgttac acggacaagc tcatccacct cacgaacgcg    120
ctcgcgaagg cggtcatcca cacgatcaag ctcaacggga tcgtcttcgt ccacgtcatc    180
acgtcgtcgg acatctgtcc gaacaacaac atcgtcgtca agtcgaactt cacgacgatg    240
ccggtcctcc agaacggggg gtacatctgg gagatgatgg agctcacgca ctgttcgcag    300
ccgaacgggc tcctcgacga caactgtgag atcaagttct cgaagaagct ctcggactcg    360
acgatgacga actacatgaa ccagctctcg gagctcctcg ggttcgacct caacccgtaa    420
```

<210> SEQ ID NO 8
<211> LENGTH: 124
<212> TYPE: PRT
<213> ORGANISM: respiratory syncytial virus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (59)..(60)
<223> OTHER INFORMATION: Xaa can be any naturally occurring amino acid

```
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (76)..(77)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid

<400> SEQUENCE: 8

Met Xaa Thr Xaa Xaa Xaa Xaa Xaa Thr Xaa Gln Xaa Leu Xaa Ile Thr
1               5                   10                  15

Asp Met Arg Pro Xaa Ser Xaa Xaa Xaa Xaa Ile Xaa Ser Leu Thr Xaa
            20                  25                  30

Xaa Ile Ile Thr His Xaa Phe Ile Tyr Leu Ile Asn Xaa Glu Cys Ile
        35                  40                  45

Val Xaa Lys Leu Asp Glu Xaa Gln Ala Thr Xaa Xaa Phe Leu Val Asn
    50                  55                  60

Tyr Glu Met Xaa Leu Leu His Xaa Val Gly Ser Xaa Xaa Tyr Lys Lys
65                  70                  75                  80

Xaa Thr Glu Tyr Asn Thr Lys Tyr Gly Thr Phe Pro Met Pro Ile Phe
                85                  90                  95

Ile Xaa His Xaa Gly Phe Xaa Glu Cys Ile Gly Xaa Lys Pro Thr Lys
            100                 105                 110

His Thr Pro Ile Ile Xaa Lys Tyr Asp Leu Asn Pro
        115                 120


<210> SEQ ID NO 9
<211> LENGTH: 375
<212> TYPE: DNA
<213> ORGANISM: respiratory syncytial virus

<400> SEQUENCE: 9

atggatacga cgcataatga taatacgccg caacgtctaa tgataacgga tatgcgtccg      60

ctatcgctag aaacgataat aacgtcgcta acgcgtgata taataacgca taaatttata     120

tatctaataa atcatgaatg tatagtacgt aaactagatg aacgtcaagc gacgtttacg     180

tttctagtaa attatgaaat gaaactacta cataaagtag gttcgacgaa atataaaaaa     240
```

```
tatacggaat ataatacgaa atatggtacg tttccgatgc cgatatttat aaatcatgat    300

ggttttctag aatgtatagg tataaaaccg acgaaacata cgccgataat atataaatat    360

gatctaaatc cgtaa                                                     375


<210> SEQ ID NO 10
<211> LENGTH: 375
<212> TYPE: DNA
<213> ORGANISM: respiratory syncytial virus

<400> SEQUENCE: 10

atggacacga cgcacaacga caacacgccg cagcgcctca tgatcacgga catgcgcccg     60

ctctcgctcg agacgatcat cacgtcgctc acgcgcgaca tcatcacgca caagttcatc    120

tacctcatca accacgagtg tatcgtccgc aagctcgacg agcgccaggc gacgttcacg    180

ttcctcgtca actacgagat gaagctcctc cacaaggtcg ggtcgacgaa gtacaagaag    240

tacacggagt acaacacgaa gtacgggacg ttcccgatgc cgatcttcat caaccacgac    300

gggttcctcg agtgtatcgg gatcaagccg acgaagcaca cgccgatcat ctacaagtac    360

gacctcaacc cgtaa                                                     375


<210> SEQ ID NO 11
<211> LENGTH: 30
<212> TYPE: PRT
<213> ORGANISM: Homo sapiens

<400> SEQUENCE: 11

Thr Thr Asn Ile Met Ile Thr Thr Ile Ile Ile Val Ile Ile Val Ile
1               5                   10                  15

Leu Leu Ser Leu Ile Ala Val Gly Leu Leu Leu Tyr Cys Lys
            20                  25                  30


<210> SEQ ID NO 12
<211> LENGTH: 26
<212> TYPE: PRT
<213> ORGANISM: Homo sapiens

<400> SEQUENCE: 12

Ala Arg Ser Thr Pro Val Pro Ile Leu Lys Ala Asn Ala Ile Thr Thr
1               5                   10                  15

Ile Leu Ala Ala Val Thr Phe Cys Phe Ala
            20                  25


<210> SEQ ID NO 13
<211> LENGTH: 20
<212> TYPE: PRT
<213> ORGANISM: Homo sapiens

<400> SEQUENCE: 13

Ala Val Thr Phe Cys Phe Ala Ser Ser Gln Asn Ile Thr Glu Glu Phe
1               5                   10                  15

Tyr Gln Ser Thr
            20


<210> SEQ ID NO 14
<211> LENGTH: 33
<212> TYPE: PRT
<213> ORGANISM: Homo sapiens

<400> SEQUENCE: 14

Gln Ser Thr Cys Ser Ala Val Ser Lys Gly Tyr Leu Ser Ala Leu Arg
```

```
1               5                   10                  15

Thr Gly Trp Tyr Thr Ser Val Ile Thr Ile Glu Leu Ser Asn Ile Lys
            20                  25                  30

Lys


<210> SEQ ID NO 15
<211> LENGTH: 27
<212> TYPE: PRT
<213> ORGANISM: Homo sapiens

<400> SEQUENCE: 15

Ile Lys Lys Asn Lys Cys Asn Gly Thr Asp Ala Lys Val Lys Leu Met
1               5                   10                  15

Lys Gln Glu Leu Asp Lys Tyr Lys Asn Ala Val
            20                  25


<210> SEQ ID NO 16
<211> LENGTH: 33
<212> TYPE: PRT
<213> ORGANISM: Homo sapiens

<400> SEQUENCE: 16

Phe Pro Gln Ala Glu Lys Cys Lys Val Gln Ser Asn Arg Val Phe Cys
1               5                   10                  15

Asp Thr Met Tyr Ser Leu Thr Leu Pro Ser Glu Val Asn Leu Cys Asn
            20                  25                  30

Val


<210> SEQ ID NO 17
<211> LENGTH: 574
<212> TYPE: PRT
<213> ORGANISM: Homo sapiens

<400> SEQUENCE: 17

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Arg Val
```

```
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Lys Cys Lys Val Gln Ser Asn Arg Val Phe Cys Asp
        355                 360                 365

Thr Met Tyr Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 18
<211> LENGTH: 897
<212> TYPE: DNA
<213> ORGANISM: respiratory syncytial virus

<400> SEQUENCE: 18
atgtcgaaaa acaaagacca acgtaccgcg aagacgttag aacgtacctg ggatactcta 60
aatcatttac tattcatatc gtcgtgccta tataagctaa atcttaaatc ggtagcacaa 120
ataacactat ccatactggc gataataatc tcgacttcgc ttataatagc agcgatcata 180
tttatagcct cggcgaacca taaagtcacg ccaacgactg cgatcataca agatgcgaca 240
tcgcagataa agaatacaac gccaacgtac ctaacccaaa atcctcaact tggtatctcg 300
ccctcgaatc cgtctgaaat aacatcgcaa atcacgacca tactagcgtc aacgacaccg 360
ggagtaaagt cgaccctaca atccacgaca gtaaagacga aaaacacgac aacgactcaa 420
acgcaaccct cgaagccgac cacgaaacaa cgccaaaata aaccaccgag caaaccgaat 480
aatgattttc actttgaagt attcaatttt gtaccctgta gcatatgtag caataatcca 540
acgtgctggg cgatctgtaa aagaataccg aacaaaaaac cgggaaaaaa aaccacgacc 600
aaacccacga aaaaaccaac gctcaaaaca acgaaaaaag atcccaaacc gcaaaccacg 660
aaatcaaaag aagtacccac gaccaaaccc acggaagagc cgaccataaa cacgaccaaa 720
acgaacataa taactacgct actcacgtcc aataccacgg gaaatccgga actcacgagt 780
caaatggaaa cgtttcactc gacttcgtcc gaaggtaatc catcgccttc gcaagtctcg 840
acaacgtccg aatacccgtc acaaccgtca tcgccaccga acacgccacg tcagtag 897

<210> SEQ ID NO 19
<211> LENGTH: 897
<212> TYPE: DNA
<213> ORGANISM: respiratory syncytial virus

<400> SEQUENCE: 19
atgtcgaaaa ataaagacca acgtacggcg aagacgctag aacgtacctg ggatacgcta 60
aatcatttac tatttatatc gtcgtgccta tataaactaa atcttaaatc ggtagcgcaa 120
ataacactat cgatactggc gataataata tcgacttcgc taataatagc agcgataata 180
tttatagcct cggcgaatca taaagtcacg ccgacgactg cgataataca agatgcgaca 240
tcgcaaataa agaatacgac gccaacgtat ctaacccaaa atccgcaact tggtatatcg 300
ccctcgaatc cgtcggaaat aacatcgcaa ataacgacca tactagcgtc gacgacaccg 360
ggtgtaaagt cgacgctaca atccacgacg gtaaagacga aaaatacgac aacgacgcaa 420
acgcaaccgt cgaaaccgac cacgaaacaa cgtcaaaata aaccaccgtc gaaaccgaat 480
aatgattttc actttgaagt atttaatttt gtaccctgtt cgatatgtag caataatccg 540
acgtgctggg cgatatgtaa aagaataccg aataaaaaac cgggaaaaaa aacgacgacc 600
aaaccgacga aaaaaccaac gctaaaaaca acgaaaaaag atccgaaacc gcaaaccacg 660
aaatcgaaag aagtacccac gacgaaaccc acggaagaac cgaccataaa tacgaccaaa 720
acgaatataa taactacgct actaacgtcc aatacgacgg gaaatccgga actaacgagt 780
caaatggaaa cgtttcattc gacttcgtcg gaaggtaatc catcgccgtc gcaagtctcg 840
acgacttccg aatatccgtc acaaccgtcg tcgccaccga atacgccacg tcaatag 897

<210> SEQ ID NO 20
<211> LENGTH: 897
<212> TYPE: DNA
<213> ORGANISM: respiratory syncytial virus

<400> SEQUENCE: 20

-continued

```
atgtcgaaaa ataaagatca acgtacggcg aaaacgctag aacgtacgtg ggatacgcta      60

aatcatctac tatttatatc gtcgtgtcta tataaactaa atctaaaatc ggtagcgcaa     120

ataacgctat cgatactagc gataataata tcgacttcgc taataatagc ggcgataata     180

tttatagcgt cggcgaatca taaagtaacg ccgacgacgg cgataataca agatgcgact     240

tcgcaaataa aaaatacgac gccgacgtat ctaacgcaaa atccgcaact aggtatatcg     300

ccgtcgaatc cgtcggaaat aacgtcgcaa ataacgacga tactagcgtc gacgacgccg     360

ggtgtaaaat cgacgctaca atcgacgacg gtaaaaacga aaaatacgac gacgacgcaa     420

acgcaaccgt cgaaaccgac gacgaaacaa cgtcaaaata aaccgccgtc gaaaccgaat     480

aatgattttc attttgaagt atttaatttt gtaccgtgtt cgatatgttc gaataatccg     540

acgtgttggg cgatatgtaa acgtataccg aataaaaaac cgggtaaaaa aacgacgacg     600

aaaccgacga aaaaaccgac gctaaaaacg acgaaaaaag atccgaaacc gcaaacgacg     660

aaatcgaaag aagtaccgac gacgaaaccg acggaagaac cgacgataaa tacgacgaaa     720

acgaatataa taacgacgct actaacgtcg aatacgacgg gtaatccgga actaacgtcg     780

caaatggaaa cgtttcattc gacttcgtcg gaaggtaatc cgtcgccgtc gcaagtatcg     840

acgacttcgg aatatccgtc gcaaccgtcg tcgccgccga atacgccgcg tcaatag        897
```

```
<210> SEQ ID NO 21
<211> LENGTH: 574
<212> TYPE: PRT
<213> ORGANISM: respiratory syncytial virus

<400> SEQUENCE: 21

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Arg Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
    210                 215                 220
```

```
Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Lys Cys Lys Val Gln Ser Asn Arg Val Phe Cys Asp
        355                 360                 365

Thr Met Tyr Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

RECOMBINANT RSV WITH SILENT MUTATIONS, VACCINES, AND METHODS RELATED THERETO

CROSS REFERENCE TO RELATED APPLICATIONS

This Application claims priority to and is a divisional of U.S. application Ser. No. 14/775,671, filed on Sep. 12, 2015, which is a national stage application filed under 35 USC § 371 of PCT Application No. PCT/US2014/027447, filed on Mar. 14, 2014, which claims the benefit of U.S. Provisional Application No. 61/781,228 filed Mar. 14, 2013, and U.S. Provisional Application No. 61/890,500 filed Oct. 14, 2013, applications which are incorporated by reference in their entirety.

BACKGROUND

Respiratory syncytial virus (RSV) leads to lower respiratory tract infections. Immunocompromised patients, premature infants, and children are particularly at risk to severe disease. RSV is the leading cause of viral death in infants. RSV treatments are focused on prevention from infection and improving respiration. Palivizumab is a humanized monoclonal antibody that can be given prophylactically. Palivizumab is not effective after RSV infection, and protection ends shortly after treatment stops. Vaccines are not currently available for RSV. Attenuated RSV vaccines candidates have failed because of suboptimal immunogenicity in infants and suboptimal stability that leads to genetic reversion towards undesirable wild-type sequences. See Teng, Infectious Disorders—Drug Targets, 2012, 12(2):129-3. Thus, there is a need to find an attenuated RSV vaccine that is appropriately immunogenic, sufficiently stable, and safe for use in infants.

Due to the redundancy of the genetic code, individual amino acids are encoded by multiple sequences of codons, sometimes referred to as synonymous codons. In different species, synonymous codons are used more or less frequently, sometimes referred to as codon bias. Genetic engineering of under-represented synonymous codons into the coding sequence of a gene has been shown to result in decreased rates of protein translation without a change in the amino acid sequence of the protein. Mueller et al. report virus attenuation by changes in codon bias. See, Science, 2008, 320:1784. See also WO/2008121992, WO/2006042156, Burns et al., J Virology, 2006, 80(7):3259 and Mueller et al., J Virology, 2006, 80(19):9687.

Luongo et al. report increased genetic and phenotypic stability of a live-attenuated respiratory syncytial virus vaccine candidate by reverse genetics. See J. Virol. 2012, 86(19):10792.

Dochow et al. report independent structural domains in paramyxovirus polymerase protein. J Biol Chem, 2012, 287:6878-91.

U.S. Pat. No. 8,580,270 reports RSV F polypeptide sequences. U.S. Pat. No. 7,951,384 reports that it contemplates a VLP RSV vaccine.

References cited herein are not an admission of prior art.

SUMMARY

In certain embodiments, the disclosure relates to the polynucleotide sequences of respiratory syncytial virus (RSV). In certain embodiments, the disclosure relates to isolated or recombinant nucleic acids and polypeptides comprising desirable nucleic acid sequences and mutations disclosed herein. In certain embodiments, isolated or recombinant RSV comprising the nucleic acids and polypeptides disclosed herein (e.g., attenuated recombinant RSV) are also provided, as are immunogenic compositions including such nucleic acids, polypeptides, and RSV genomes that are suitable for use as vaccines. Attenuated or killed RSV containing these nucleic acids and mutation in the form of copied nucleic acids (e.g., cDNAs) are also contemplated.

In certain embodiments, this disclosure relates to isolated nucleic acids, recombinant respiratory syncytial virus (RSV) with codon deoptimization, vaccines produced therefrom, and vaccination methods related thereto. In certain embodiments, the recombinant RSV comprises the genes NS1, NS2, N, P, M, SH, G, F, M2, and L of strain A2, line 19, or Long strain or variants thereof. In certain embodiments, the codon deoptimization is in the nonstructural genes NS1 and NS2 and optionally in a gene G and optionally in a gene L. In further embodiments, the gene SH is deleted. In further embodiments, the gene F is mutated, e.g., an I to V mutation corresponding to residue 557 of RSV strain line 19 F protein.

In certain embodiments, the disclosure relates to isolated nucleic acids encoding deoptimized genes NS1 and/or NS2 and optionally the gene G and optionally the gene L of a wild-type human RSV or variant wherein the nucleotides are substituted such that a codon to produce Gly is GGT, a codon to produce Asp is GAT, a codon to produce Glu is GAA, a codon to produce His is CAT, a codon to produce Ile is ATA, a codon to produce Lys is AAA, a codon to produce Leu is CTA, a codon to produce Asn is AAT, a codon to produce Gln is CAA, a codon to produce Val is GTA, or a codon to produce Tyr is TAT, or combinations thereof. In certain embodiments, a gene in the isolated nucleic acid further comprises a combination of at least two, three, four, five, six, seven, eight nine, ten, or all of the individual codons. In certain embodiment, a gene in the isolated nucleic acid comprises at least 20, 30, 40, or 50 or more of the codons.

In certain embodiment, this disclosure relates to isolated nucleic acid as disclosed herein wherein the nucleotides are substituted such that a codon to produce Ala is GCG, a codon to produce Cys is TGT, a codon to produce Phe is TTT, a codon to produce Pro is CCG, a codon to produce Arg is CGT, a codon to produce Ser is TCG, or a codon to produce Thr is ACG, or combinations thereof. In certain embodiments, a gene containing the nucleic acid comprises a combination of at least two, three, four, five, six, seven, eight nine, ten, eleven, twelve, thirteen, fourteen, fifteen, sixteen, or all of the individual codons. In certain embodiments, a gene in the isolated nucleic acid further comprises at least 20, 30, 40, or 50 or more of the codons.

In certain embodiments, the disclosure relates to nucleic acids disclosed herein encoding an NS1 having SEQ ID NO: 5

MG$X^1$N$X^2$LS$X^3$IK$X^4$RLQNL$X^5X^6$NDEVALLKIT-CY$X^7$DKLI$X^8$LTNALAKA$X^9$IHTIKL NGIVF$X^{10}$HVITSS$X^{11}X^{12}$CP$X^{13}$N$X^{14}$IVVKSNFTT-MP$X^{15}$L$X^{16}$NGGYI$X^{17}$E$X^{18}X^{19}$ELTH CSQ$X^2$NG$X^{21}X^{22}X^{23}$DNCEIKFS$X^{24}X^{25}$L$X^{26}$DS$X^{27}$M-T$X^{28}$Y$X^{29}X^{30}$Q$X^{31}$S$X^{32}$LLG$X^{33}$DL $X^{34}X^{35}$, wherein $X^1$-$X^{35}$ are any amino acid or $X^1$ is S or C; $X^2$ is S or T; $X^3$ is M or V; $X^4$ is V or I; $X^5$ is F or L; $X^6$ is D or N; $X^7$ is T or A; $X^8$ is H, L, or Q; $X^9$ is V or T; $X^{10}$ is V or I; $X^{11}$ is D or E; $X^{12}$ is I, A, or V; $X^{13}$ is N or D; $X^{14}$ is N or S; $X^{15}$ is V, I, or A; $X^{16}$ is Q or R; $X^{17}$ is W or any amino acid; $X^{18}$ is M or L; $X^{19}$ is M or I; $X^{20}$ is P or L; $X^{21}$ is L or V; $X^{22}$ is L, M, or I; $X^{23}$ is D or V; $X^{24}$ is K or R; $X^{25}$ is K or R; $X^{26}$ is S or any amino acid; $X^{27}$ is T or V; $X^{28}$ is N or D; $X^{29}$ is M or I; $X^{30}$ is N or S; $X^{31}$ is L or I; $X^{32}$ is E or D; $X^{33}$ is F or L; $X^{34}$ is N or H; and $X^{35}$ is P or S or deleted.

In certain embodiments, the disclosure relates to nucleic acids disclosed herein encoding an NS1 of RSV as provided in NCBI Accession number NP 044589.1, NP_056856.1, P04544.1, AEQ63513.1, AFM55237.1, AFV32554.1, Q86306.1, AFV32528.1, AFM55248.1, AFM95358.1, AFV32568.1, ACY68428.1, CBW45413.1, AC083290.1, AFM55347.1, CBW45433.1, AEQ63459.1, AFM55204.1, AFV32572.1, AFV32558.1, CBW45429.1, CBW45445.1, AFV32596.1, CBW45481.1, CBW47561.1, P24568.1, AAR14259.1, CBW45451.1, CBW45447.1, CBW45471.1, BAE96914.1, CBW45463.1, CBW45473.1, or CBW45467.1 or variants comprising one, two, or three amino acid insertions, deletions, substitutions, or conserved substitutions.

In certain embodiments, the disclosure relates to an isolated nucleic acid comprising SEQ ID NO: 6 or SEQ ID NO: 7 or a sequence with 60%, 70%, 80%, 90%, 95% or greater sequence identity thereto.

In certain embodiments, the disclosure relates to nucleic acids disclosed herein encoding an NS2 having SEQ ID NO: 8, M$X^{1}$T$X^{2}X^{3}X^{4}X^{5}X^{6}$T$X^{7}$Q$X^{8}$L$X^{9}$ITDMRP$X^{10}$S$X^{11}X^{12}X^{13}X^{14}$I$X^{15}$SLT$X^{16}X^{17}$IITH$X^{18}$FIYLI N$X^{19}$ECIV$X^{20}$KLDE$X^{21}$QAT$X^{22}X^{23}$FLVNYEM$X^{24}$LLH$X^{25}$VGS$X^{26}X^{27}$YKK$X^{28}$TEYNTK YGTFPMPIFI$X^{29}$H$X^{30}$GF$X^{31}$ECIG$X^{32}$KPTKHTPII$X^{33}$KYDLNP, wherein $X^{1}$-$X^{33}$ are any amino acid or $X^{1}$ is D or S; $X^{2}$ is T, A, or K; $X^{3}$ is H, S, or N; $X^{4}$ is N or P; $X^{5}$ is D, G, or E; $X^{6}$ is T or N; $X^{7}$ is P, M, Q, S, or A; $X^{8}$ is R or G; $X^{9}$ is M or I; $X^{10}$ is L or M; $X^{11}$ is L, M, or I; $X^{12}$ is I, D, or E; $X^{13}$ is T or S; $X^{14}$ is I or V; $X^{15}$ is I or T; $X^{16}$ is R or K; $R^{17}$ is D or E; $R^{18}$ is R or K; $R^{19}$ is H or N; $X^{20}$ is R or K; $X^{21}$ is R or K; $X^{22}$ is F or L; $X^{23}$ is T or A; $X^{24}$ is K or N; $X^{25}$ is K or R; $X^{26}$ is T or A; $X^{27}$ is K or I; $X^{28}$ is T or S; $X^{29}$ is N or any amino acid; $X^{30}$ is D or G; $X^{31}$ is L or I; $X^{32}$ is I or V; and $X^{33}$ is Y or H.

In certain embodiments, the disclosure relates to nucleic acids disclosed herein encoding an NS1 having an NS2 of RSV as provided in NCBI Accession number NP_044590.1, NP_056857.1, CBW45420.1, AFM95337.1, CBW45416.1, CBW45430.1, AFV32529.1, Q86305.1, AEQ63383.1, CBW45424.1, AFM55546.1, CBW45444.1, P04543.2, AFM55326.1, AFM55425.1, AFM55381.1, AFM55458.1, AFM55216.1, AAB59851.1, AEQ63372.1, AFM55337.1, CBW45426.1, AFV32515.1, AFV32519.1, AAR14260.1, CBW47562.1, AFV32643.1, P24569.1, AFV32657.1 AFI25256.1, CBW45480.1, AFV32605.1, AEQ63580.1, AFV32627.1, AFV32665.1, CBW45482.1, CBW45478.1, CBW45462.1, AEQ63635.1, CBW45448.1, CBW45464.1, CBW45484.1, or CBW45474.1 or variants comprising one, two or three amino acid insertions, deletions, substitutions, or conserved substitutions.

In certain embodiments, the disclosure relates to an isolated nucleic acid comprising SEQ ID NO: 9 or SEQ ID NO: 10 or a sequence with 60%, 70%, 80%, 90%, 95% or greater sequence identity thereto.

In certain embodiments, the disclosure relates to recombinant vectors comprising a nucleic acid disclosed herein.

In certain embodiments, the disclosure relates to an attenuated recombinant RSV comprising a nucleic acid disclosed herein.

In certain embodiments, the disclosure relates to expression system comprising a vector disclosed herein or an attenuated recombinant RSV disclosed herein.

In certain embodiments, the disclosure relates to vaccines comprising an attenuated recombinant RSV disclosed herein.

In certain embodiments, the disclosure relates to methods of vaccination comprising administering an effective amount of a vaccine disclosed herein to a subject at risk of an RSV infection.

In certain embodiments, the subject is younger than 2 months or 6 months of age, under 1 year of age, born prematurely, have congenital heart or lung disease, having chemotherapy or a transplantation, or diagnosed with asthma, congestive heart failure or chronic obstructive pulmonary disease, leukemia, or HIV/AIDS.

In certain embodiments, vaccine is administered in combination with motavizumab, palivizumab, or another humanized monoclonal antibody directed against an epitope in the antigenic site II of the F protein of RSV.

In certain embodiments, the disclosure relates to vectors disclosed herein comprising a bacterial artificial chromosome (BAC), and a nucleic acid sequence comprising respiratory syncytial virus (RSV), and the BAC contains all genes that are essential for the generation of an infectious viral particle in a host cell. The nucleic acid sequence may be a viral genome or antigenome in operable combination with a regulatory element. Typically, the bacterial artificial chromosome comprises one or more genes selected from the group consisting of oriS, repE, parA, and parB genes of factor F in operable combination with a selectable marker, e.g., a gene that provides resistance to an antibiotic.

The nucleic acid sequence may be the genomic or antigenomic sequence of the virus which is optionally mutated as provided herein, e.g., RSV strain which is optionally mutated. In certain embodiments, the expression vector is a plasmid comprising MluI, ClaI, BstBl, SacI restriction endonuclease cleavage sites and optionally an AvrII restriction endonuclease cleavage site outside the region of the wild-type viral sequence or outside the sequences that encode viral genes or outside the viral genome or antigenome. In certain embodiments, the nucleic acid sequence further comprises a selectable marker or reporter gene in operable combination therewith, e.g., a gene that encodes a fluorescent protein.

In certain embodiments, the disclosure relates to isolated bacteria comprising one or more vectors disclosed herein, and other embodiments, the disclosure relates to an isolated cell comprising one or more vectors disclosed herein. In certain embodiments, the vector comprises an RSV antigenome and one or more vectors selected from the group consisting of: a vector encoding an N protein of RSV, a vector encoding a P protein of RSV, a vector encoding an L protein of RSV, and a vector encoding an M2-1 protein of RSV. Typically, the vector comprises a regulatory element, e.g., promoter, and the isolated eukaryotic cell expresses a nucleic acid or polypeptide that activates the regulatory element, e.g., encodes a polypeptide that activates transcription downstream of the promoter. In certain embodiments, the promoter is T7, and the polypeptide that activates transcription downstream of the promoter is T7 RNA polymerase.

In certain embodiments, the disclosure relates to methods of generating respiratory syncytial virus (RSV) particles comprising inserting a vector with a BAC gene and a RSV antigenome into an isolated eukaryotic cell and inserting one or more vectors selected from the group consisting of: a vector encoding an N protein of RSV, a vector encoding a P protein of RSV, a vector encoding an L protein of RSV, and a vector encoding an M2-1 protein of RSV into the cell under conditions such that RSV virion is formed. Inserting a vector into a cell may occur by physically injecting, electroporating, or mixing the cell and the vector under conditions such that the vector enters the cell.

In certain embodiments, the disclosure relates to the stability of the line 19 F557 mutant virus compared to other strains, and val at 557 making RSV expressing line 19 F even more thermostable. Val at position 557 in other strains is also likely stabilizing; thus the 557 position is important for thermal stability. In certain embodiments, the disclosure contemplates other mutations in line 19 F or other RSV strains at position 557 (any amino acid, e.g., alanine, valine, isoleucine, leucine) in any F strain context, that improves thermostability of the RSV virus.

In certain embodiments, the disclosure contemplates RSV F polypeptide comprising an alanine, valine, or leucine at position 557, e.g., alanine or leucine in position 557 of SEQ ID NO: 17.

In certain embodiments, the disclosure relates to certain desirable sequence of RSV F polypeptides e.g., line 19 sequences comprising a valine at position 557, e.g., SEQ ID NO: 17, and recombinant nucleic acids encoding the same. In certain embodiments, the disclosure contemplates recombinant vectors comprising nucleic acids encoding these polypeptides and cells comprising said vectors.

In certain embodiments, the disclosure relates to immunogenic compositions comprising an immunologically effective amount of a recombinant respiratory syncytial virus (RSV), RSV polypeptide, RSV particle, RSV virus-like particle, and/or nucleic acid disclosed herein. In certain embodiments, the disclosure relates to methods for stimulating the immune system of an individual to produce a protective immune response against RSV. In certain embodiments, an immunologically effective amount of a RSV, polypeptide, and/or nucleic acid disclosed herein is administered to the individual in a physiologically acceptable carrier.

In certain embodiments, the disclosure relates to medicaments and vaccine products comprising nucleic acids disclosed herein for uses disclosed herein.

In certain embodiments, the disclosure relates to uses of nucleic acids or vectors disclosed herein for the manufacture of a medicament for uses disclosed herein.

BRIEF DESCRIPTIONS OF THE FIGURES

FIG. 1 shows a table with the least used codons in human genes and in specific RSV strains.

Figure 3:
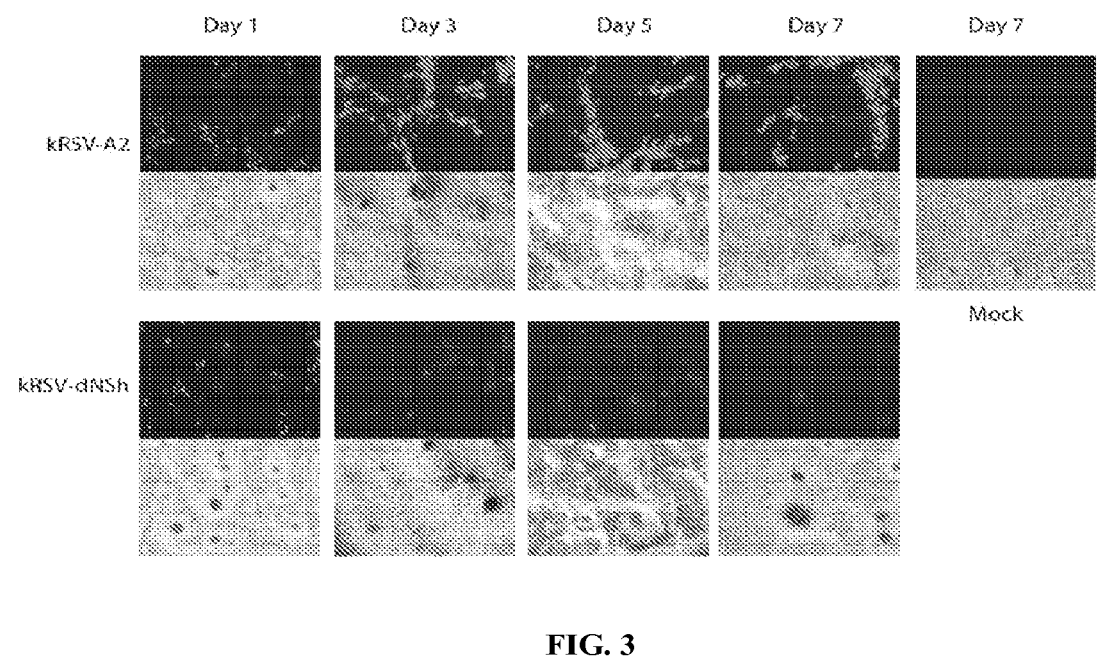

FIG. 3 shows data on viral load experiments using certain embodiments disclosed herein. Time course images for NHBE cells infection at MOI of 0.2, showing mKate2 fluorescence produced by the recombinant viruses. *P<0.05

Figure 4:
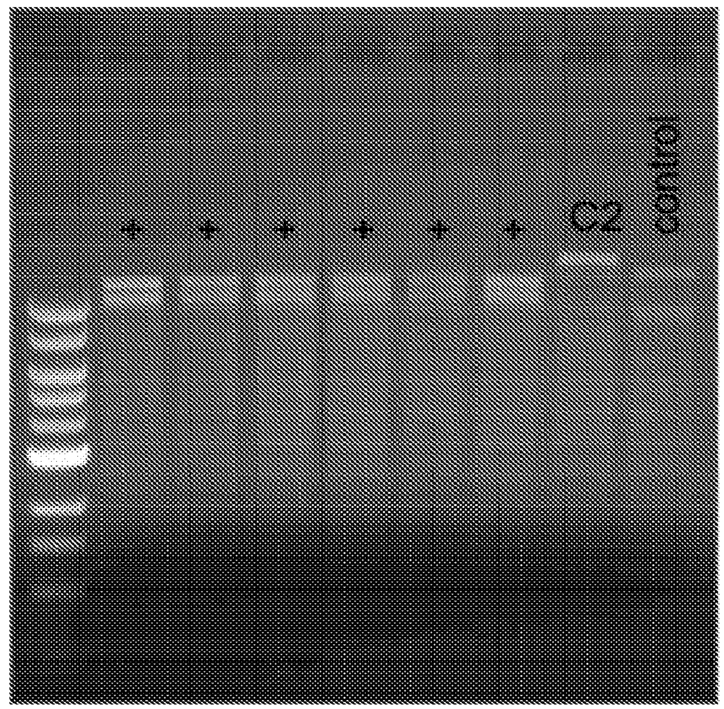

FIG. 4 shows a gel after insertion of galK operon into BAC-RSV by recombineering. MluI digest. Lane 1, ladder marker. Mini-prep BAC DNAs (lanes 2 to 7). Lane 8, parental BAC-RSV "C2" clone. Lane 9, galK-containing plasmid. galK operon has a Mlu I restriction site that serves as a marker for introduction of galK by homologous recombination.

Figure 5:
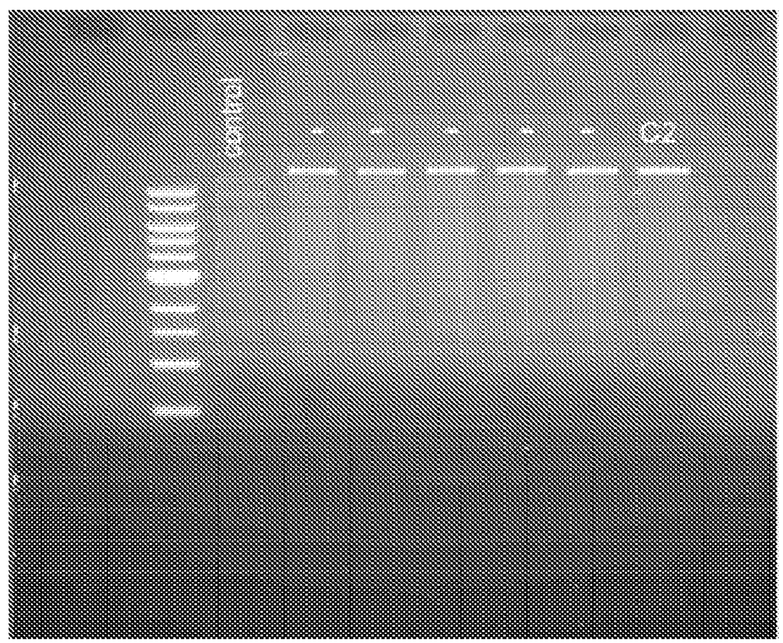

FIG. 5 shows a gel after deletion of galK operon from BAC-RSV by recombineering. MluI digest of galK-containing plasmid (lane 2), BAC mini-prep DNAs (lanes 3-7), and parental BAC-RSV clone C2 (lane 8).

Figure 6A:
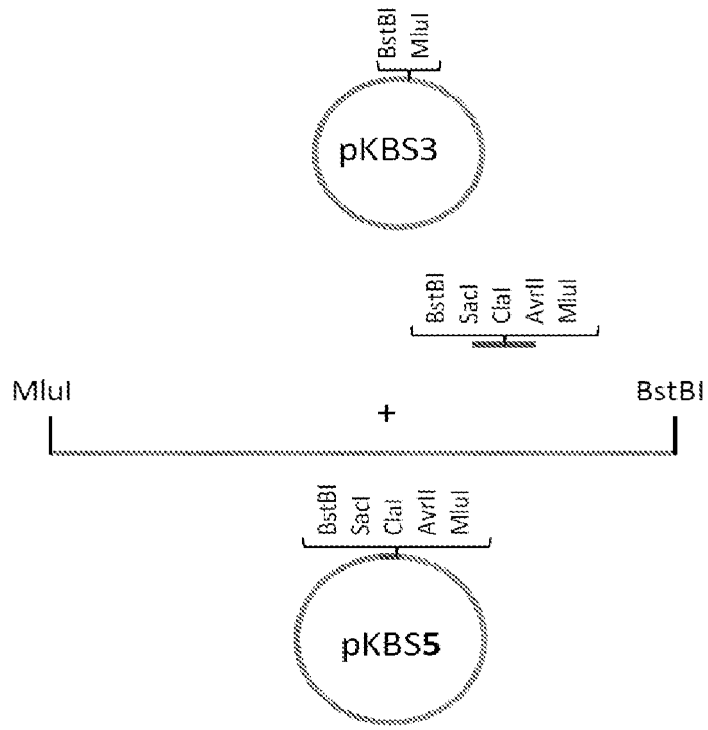
Figure 6B:
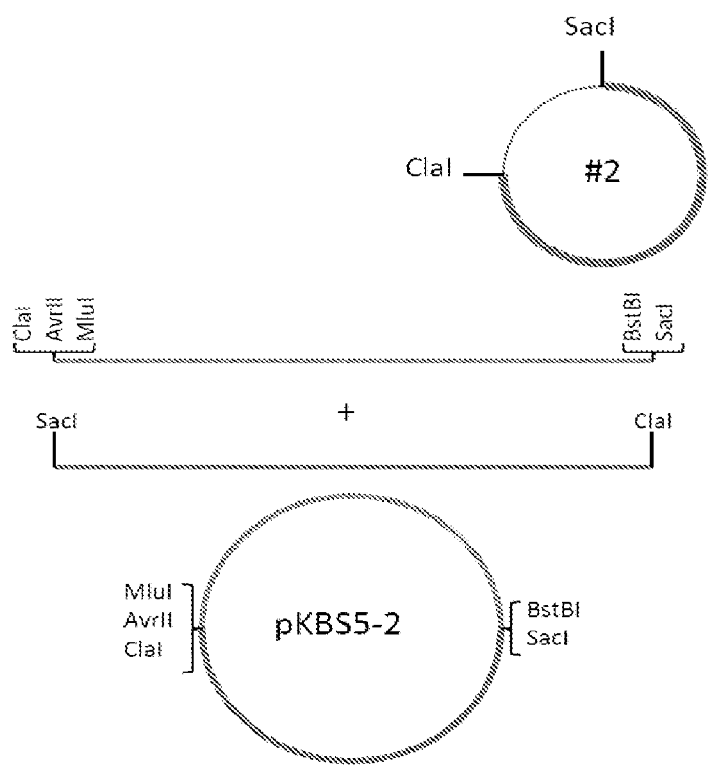
Figure 6C:
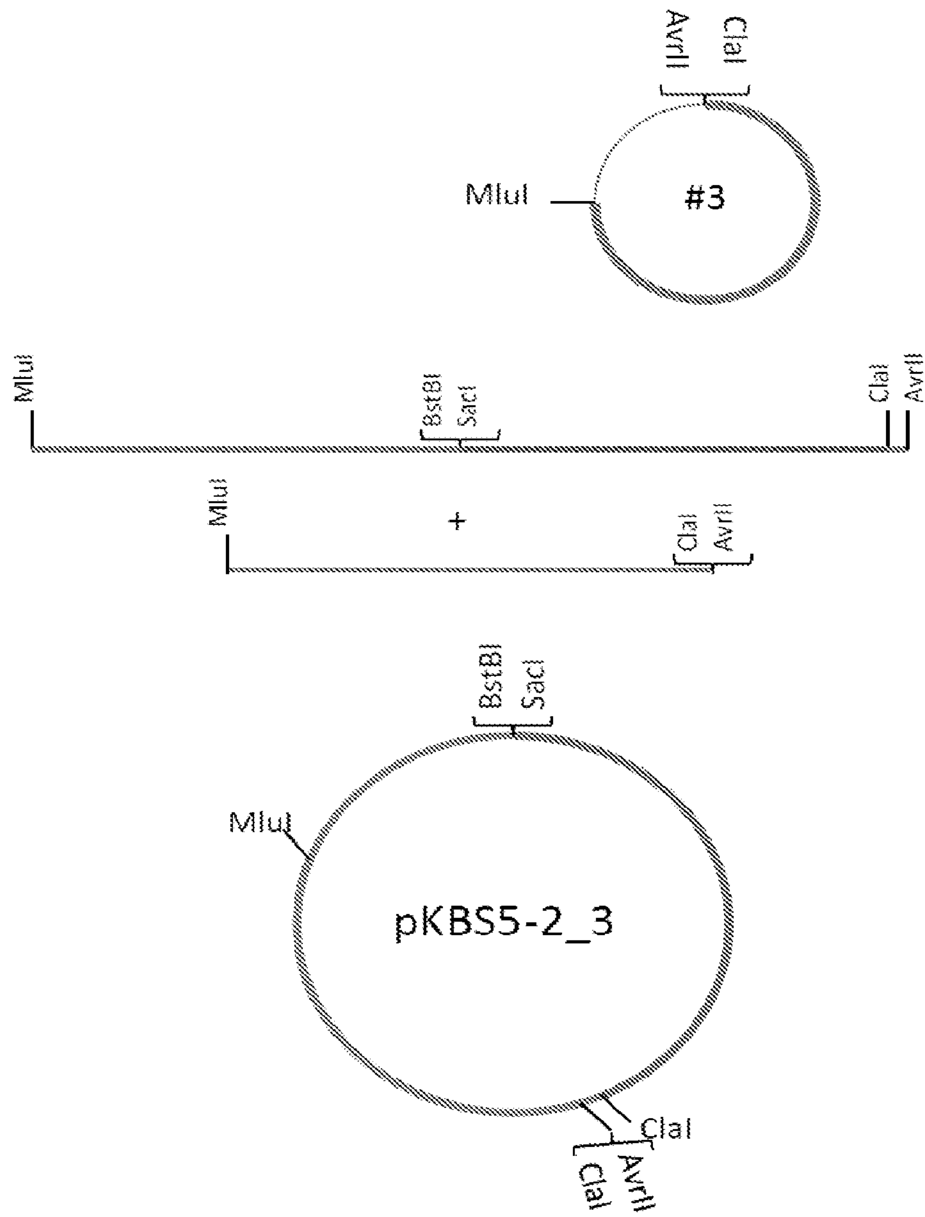
Figure 6D:
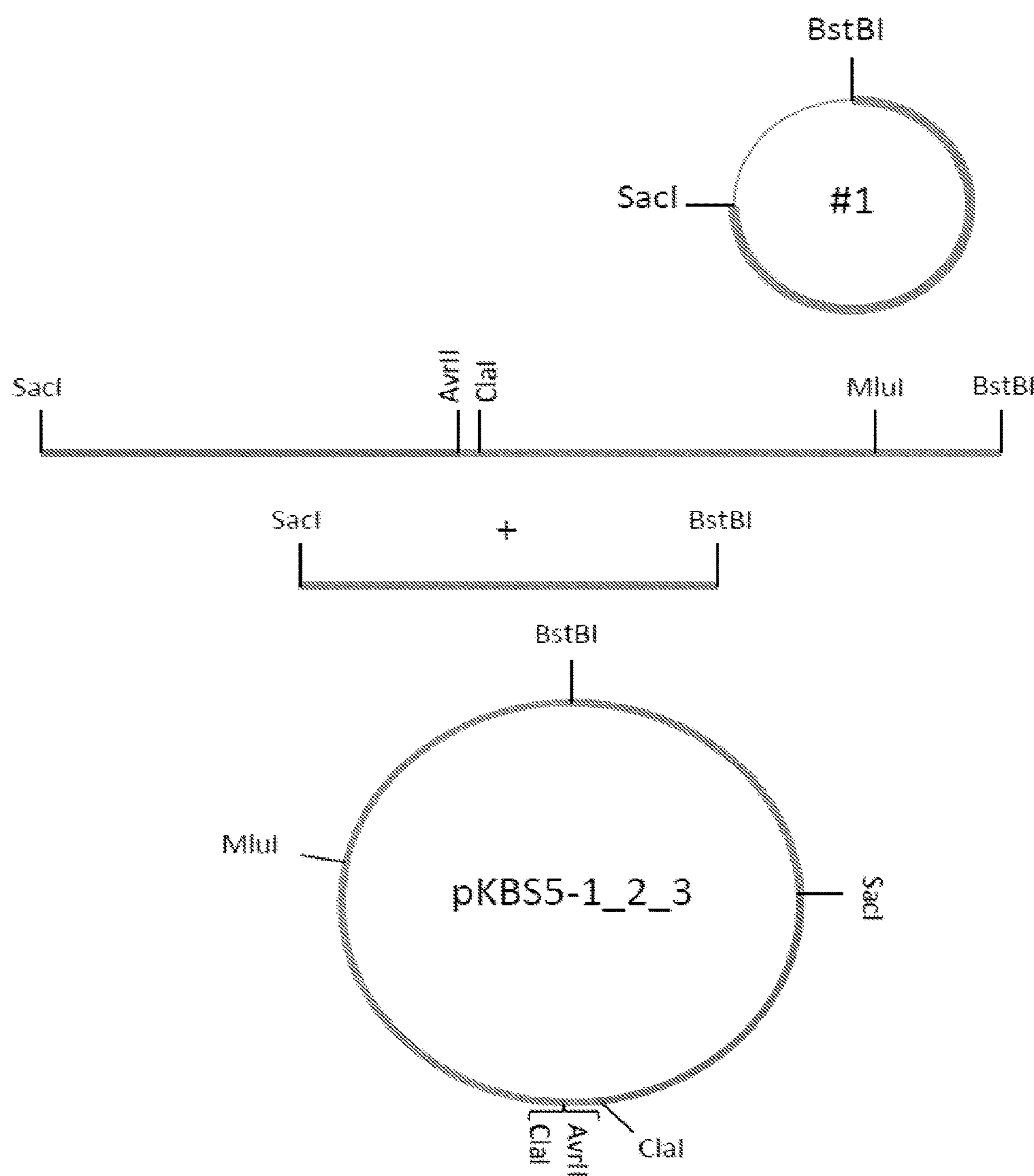
Figure 6E:
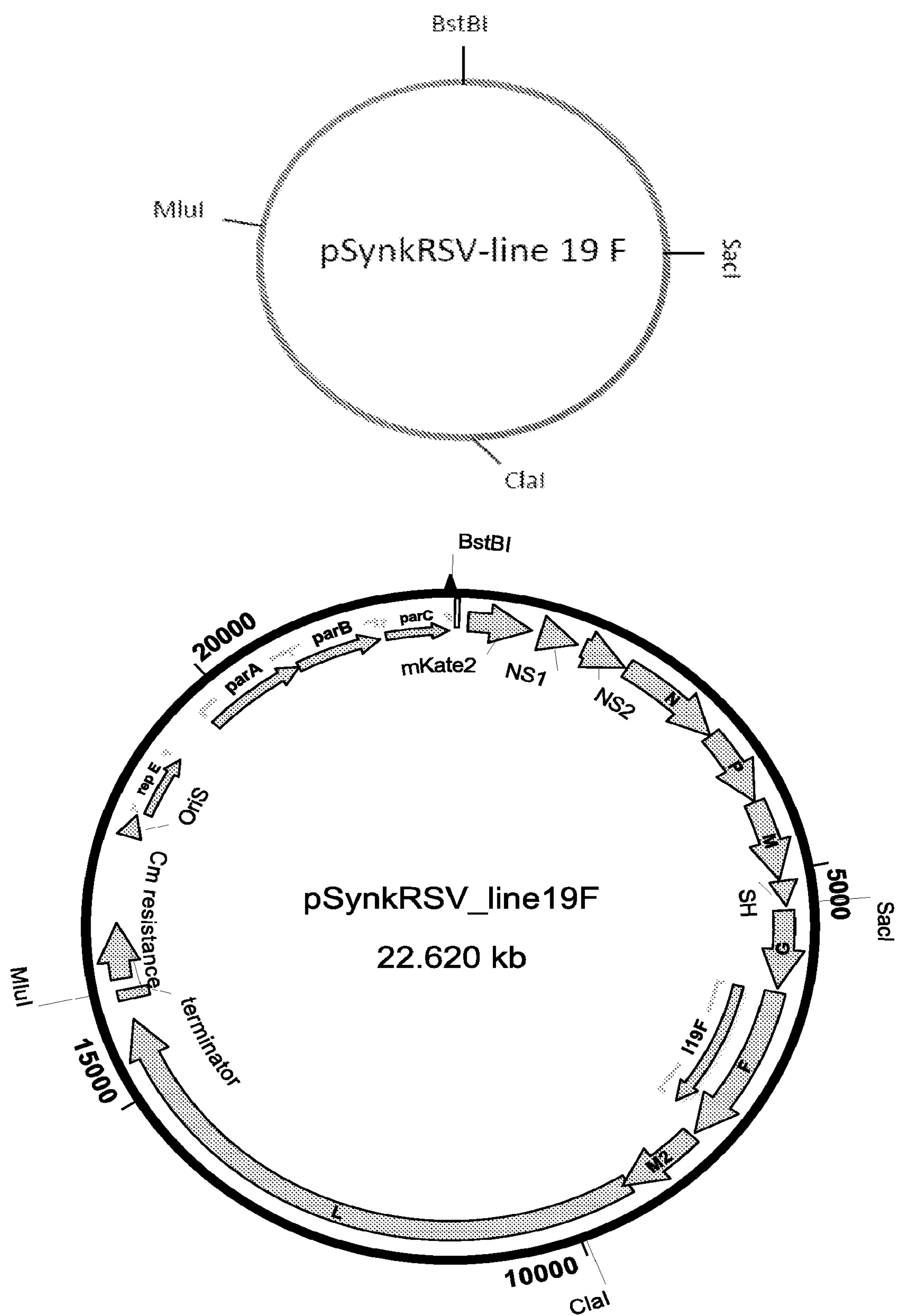

FIGS. 6A, 6B, 6C, 6D, and 6E schematically illustrate steps for creating a BAC-RSV. Three plasmids with RSV segments are generated (see experimental); FIG. 6A shows pKBS3 is cut at BstBl and MluI sites to linearize, and is ligated to an oligonucleotide adapter providing pKBS5; FIG. 6B shows pSynRSV #2 with SacI and ClaI is cut and ligated to pKBS5 providing pKBS5-2; FIG. 6C shows pSynRSV #3 with AvrII and MluI is cut and ligated to pKBS5_2 providing pKBS5_2_3; FIG. 6D shows pSynRSV #1 with BstBl and SacI is cut and ligated to pKBS5_2_3 providing pKBS5_1_2_3. FIG. 6E shows Recombineering is used to delete nucleotides between two ClaI sites generating pSynRSV-line 19F.

Figure 7A:
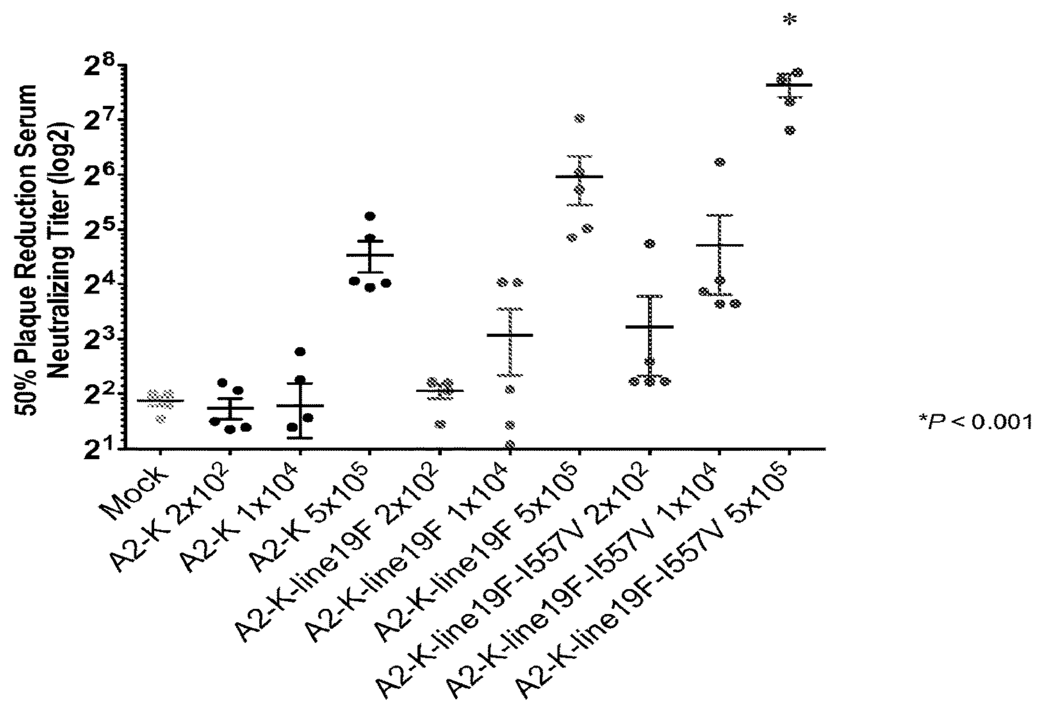
Figure 7B:
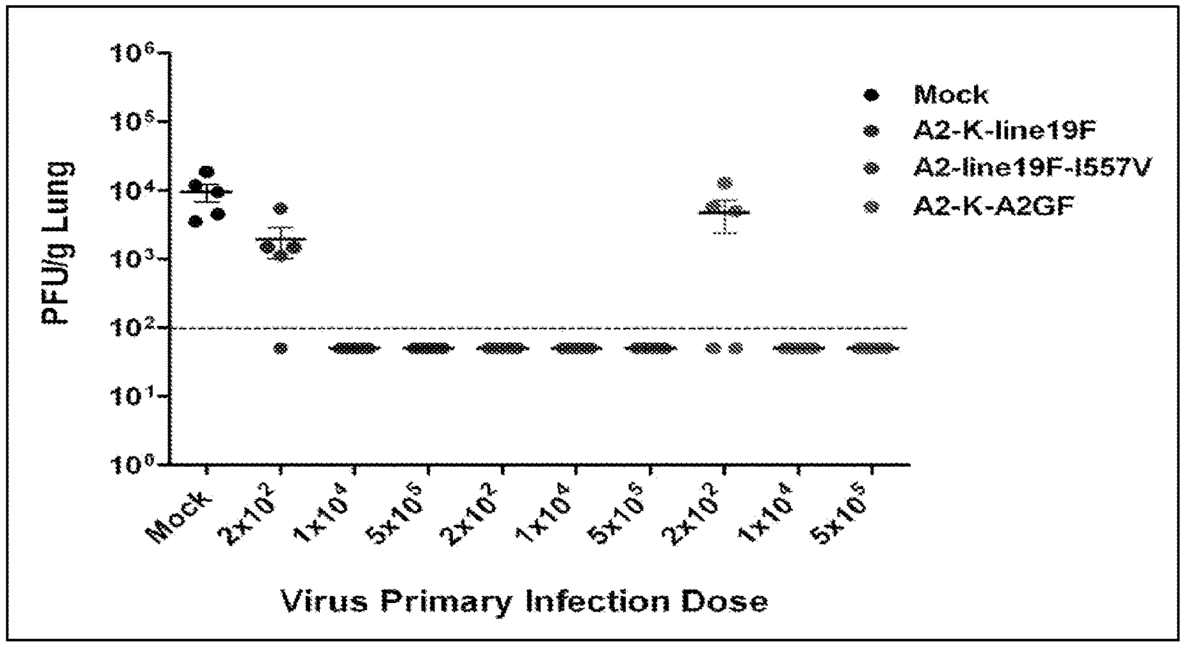

FIGS. 7A and 7B show data showing indicating the immunogenicity of an RSV strain with an F gene I557 to V mutation. FIG. 7A shows that mice were infected with indicated doses of A2-K-line19F, A2-line19F-I557 V, or A2-K-A2GF and 29 days later challenged with RSV strain 12-35. FIG. 7B shows that lung viral load was measured day 4 post-challenge. The dotted line indicates the limit of detection.

Figure 8:
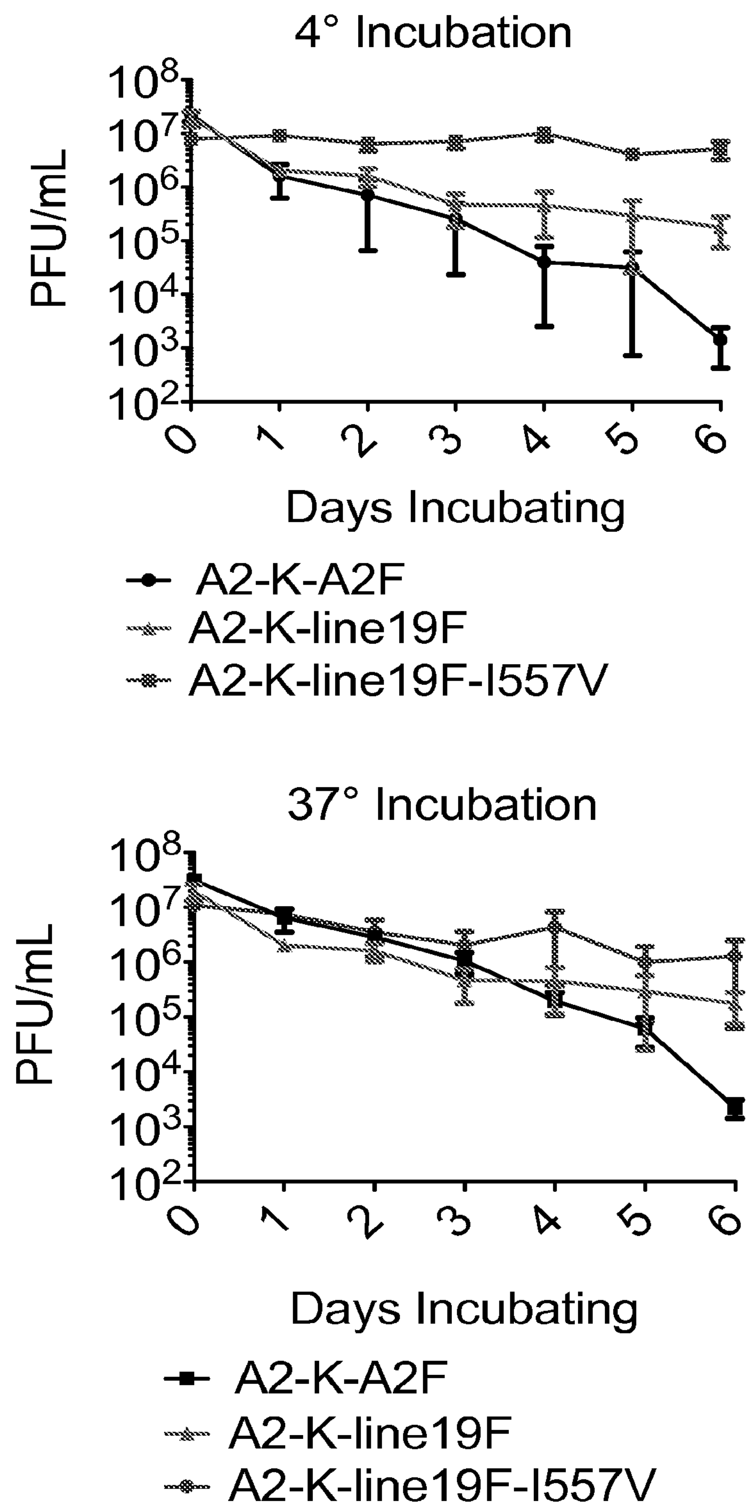

FIG. 8 shows data indicating the superior thermostability of RSV strains with an A2-line 19 F gene I557 to V mutation (SEQ ID NO:17). Viruses were incubated at indicated temperatures and viral titers were measured every day for 6 days. The results at 4° C. are statistically significant between viruses (P<0.01). The results at 37° C. demonstrate the same phenotype.

FIG. 9 illustrates an RSV sequence comparison of strain 19, I557 V mutation (SEQ ID NO:17) (Query) and the typical RSV strain 19 sequence (Sbjct).

FIG. 10 illustrates an RSV sequence comparison of strain 19, I557 V mutation (SEQ ID NO:17) (Query) and sequence 61 from U.S. Pat. No. 7,951,384 (Sbjct).

FIG. 11 illustrates an RSV sequence comparison of strain 19, I557 V mutation (SEQ ID NO:17) (Query) sequence 12 from U.S. Pat. No. 8,580,270 (Sbjct).

Figure 12:
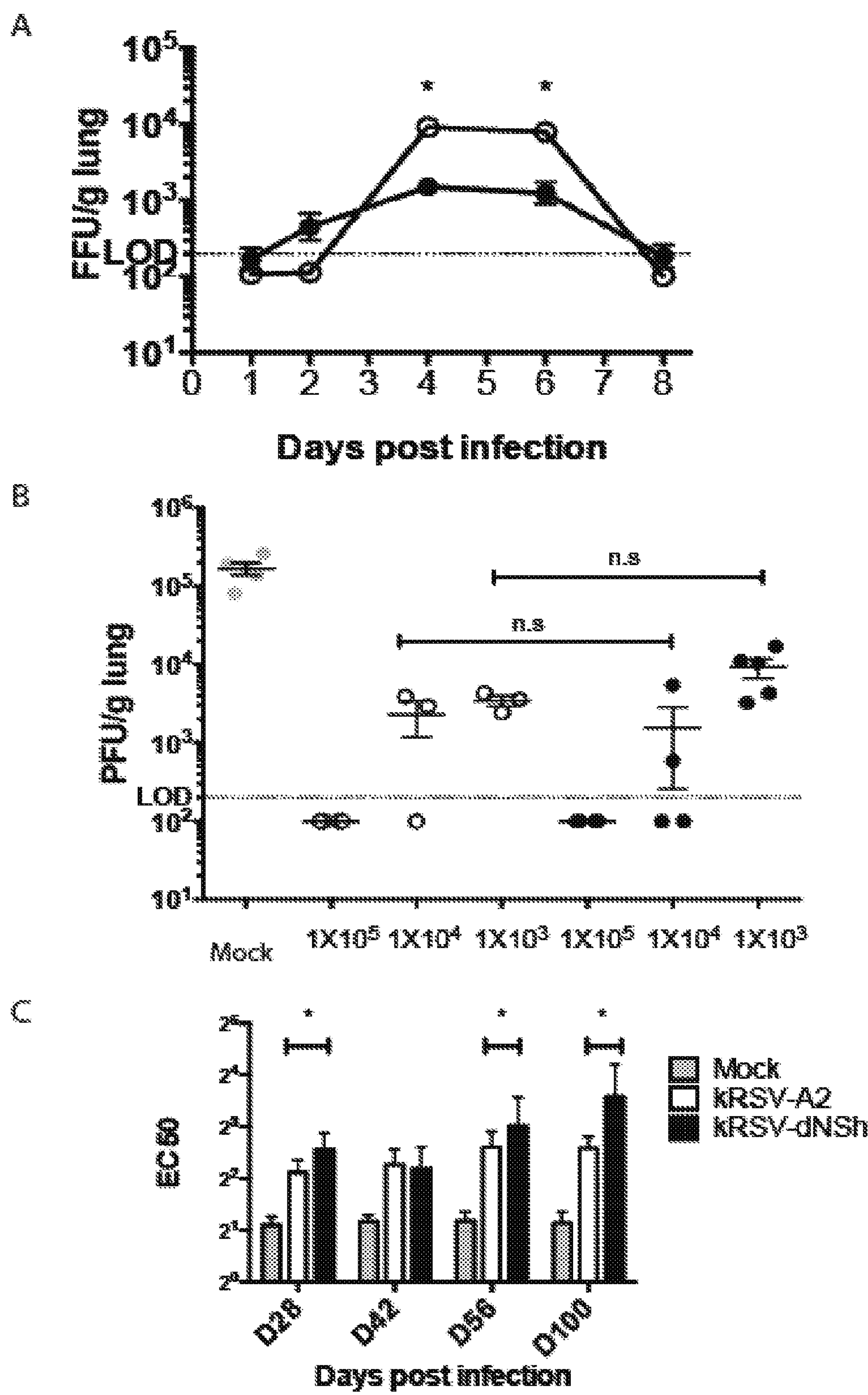

FIGS. 12A, 12B and 12C show data on attenuation, efficacy, and immunogenicity of embodiments disclosed herein. FIG. 12A shows 6-8 week old BALB/c mice (n=5 per group) were infected i.n. with 1.6×105 FFU of kRSV-A2 (open circle) or kRSV-dNSh (closed circle) and lung viral titer was assayed on days 1, 2, 4, 6, and 8 p.i. Data represent one of two replicate experiments with similar results. *P<0.05. FIG. 12B shows BALB/c mice were vaccinated i.n. with varying doses ($10^5$ FFU, $10^4$ FFU, and $10^3$ FFU) of kRSV-A2 (open circle) or kRSV-dNSh (closed circle), or mock-infected, and 100 days after vaccination, mice were challenged with $1.6\times10^6$ PFU RSV 12-35 strain. Lung peak viral loads were measured on day 4 after challenge. Each symbol represents one mouse. Dashed lines (12A and 12B) denote the limit of detection for plaque assay. Titers below the limit of detection were assigned half the value of the limit of detection. FIG. 12C shows BALB/c mice (n=5 per group) were mock-infected or infected with 105 FFU of either kRSV-A2 or kRSV-dNSh and serum nAb titers were measured at indicated days after infection. *P<0.05.

FIGS. 13A and 13B show data on vaccine efficacy for certain embodiments disclosed herein. 6-8 week old BALB/c mice (n=5 per group) were mock-infected or vaccinated with varying indicated doses of kRSV-A2 (open circle) or kRSV-dNSh (closed circle). Mice were challenged 28 days later with (13A) $2\times10^6$ PFU RSV A2-line19 strain or (13B) $5\times10^5$ PFU RSV 12-35. Lung viral loads were measured day 4 after challenge. Each symbol represents one mouse. Dashed lines denote the limit of detection for plaque assay. Titers below the limit of detection were assigned half the value of the limit of detection.

Figure 14:
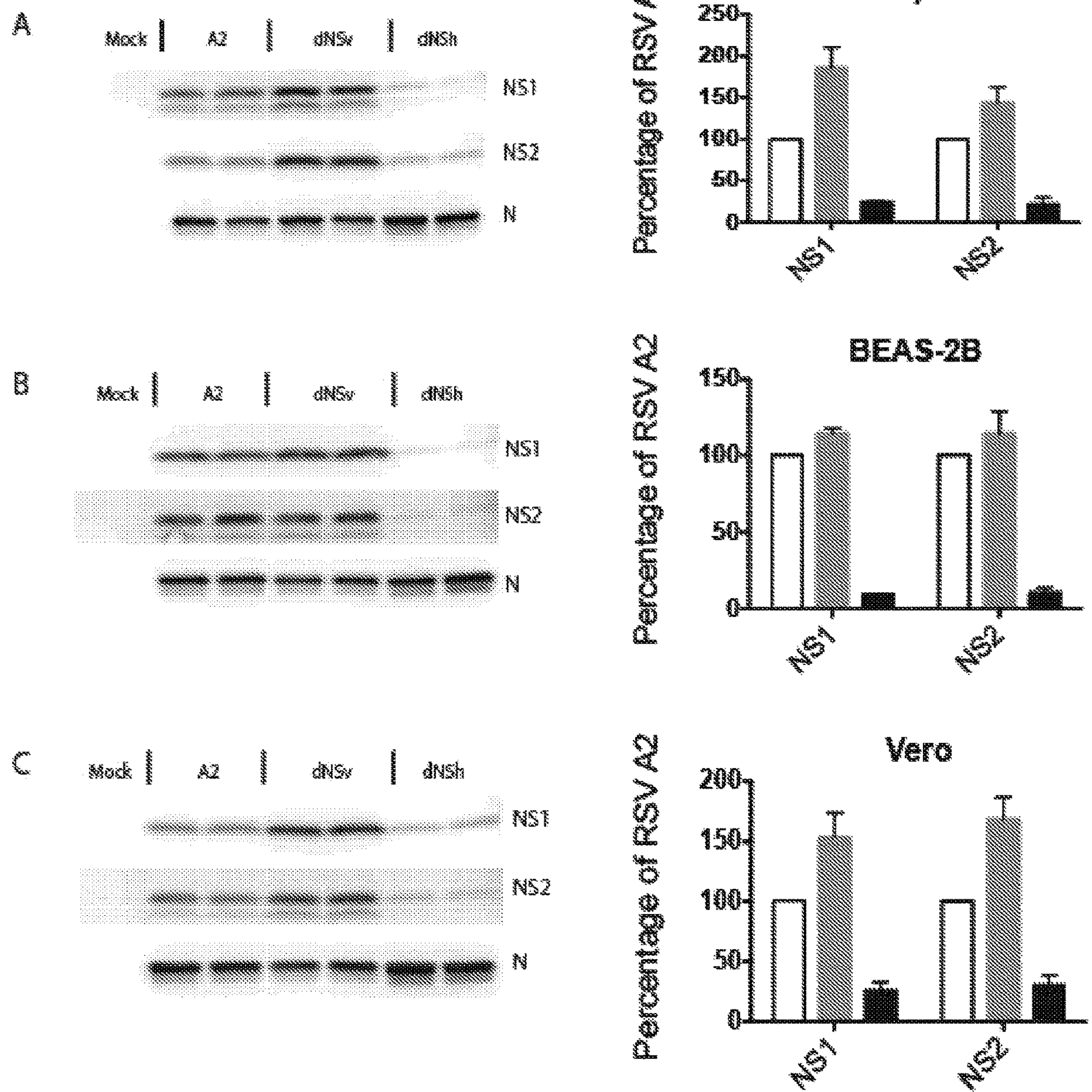

FIGS. 14A, 14B, and 14C show data on the expression of NS1 and NS2 proteins during RSV infection in cell lines. HEp-2 (14A), BEAS-2B (14B) and Vero (14C) cells were mock-infected or infected with either kRSV-A2, kRSV-dNSh, or kRSV-dNSv at MOI 5. Twenty hr p.i., NS1 and NS2 protein levels were analyzed by western blot and densitometry. Representative blots are shown on the left. Densitometry from 2-3 independent experiments is shown on the right. After normalizing to RSV N protein levels, NS1 and NS2 protein levels expressed by each virus were normalized to those during kRSV-A2 infection and expressed as percentage ±SEM. Unfilled bars represent kRSV-A2, gray bars represent kRSV-dNSv, and black bars represent kRSV-dNSh.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

The terms "protein" and "polypeptide" refer to compounds comprising amino acids joined via peptide bonds and are used interchangeably.

The term "portion" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The term "a polynucleotide having a nucleotide sequence encoding a gene" or "a polynucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison.

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present disclosure.

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term “regulatory element” refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise “promoter” and “enhancer” elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and are found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms “promoter element,” “promoter,” or “promoter sequence” as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term “tissue specific” as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term “cell type specific” as applied to a promoter refers to a promoter which is capable of directing selective expression of a nucleotide sequence of interest in a specific type of cell in the relative absence of expression of the same nucleotide sequence of interest in a different type of cell within the same tissue. The term “cell type specific” when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term “constitutive” when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, a “regulatable” or “inducible” promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The enhancer and/or promoter may be “endogenous” or “exogenous” or “heterologous.” An “endogenous” enhancer or promoter is one that is naturally linked with a given gene in the genome. An “exogenous” or “heterologous” enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a “heterologous promoter” in operable combination with the second gene. A variety of such combinations are contemplated (e.g., the first and second genes can be from the same species, or from different species).

Efficient expression of recombinant DNA sequences in eukaryotic cells typically requires expression of signals directing the efficient termination and polyadenylation of the resulting transcript. Transcription termination signals are generally found downstream of the polyadenylation signal and are a few hundred nucleotides in length. The term “poly(A) site” or “poly(A) sequence” as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be “heterologous” or “endogenous.” An endogenous poly(A) signal is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation.

The term “vector” refers to nucleic acid molecules that transfer DNA segment(s) from one cell to another. The term “vehicle” is sometimes used interchangeably with “vector.”

The terms “expression vector” or “expression cassette” refer to a recombinant nucleic acid containing a desired coding sequence and appropriate nucleic acid sequences used for the expression of the operably linked coding sequence in a particular host organism. Nucleic acid sequences used for expression in prokaryotes typically include a promoter, an operator (optional), and a ribosome binding site, often along with other sequences. Eukaryotic cells are known to utilize promoters, enhancers, and termination and polyadenylation signals.

The term "host cell" refers to any cell capable of replicating and/or transcribing and/or translating a heterologous gene. Thus, a "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The term "selectable marker" refers to a gene which encodes an enzyme having an activity that confers antibiotic or drug resistance upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, modified katushka, mkate and mkate2 (See, e.g., Merzlyak et al., Nat. Methods, 2007, 4, 555-557 and Shcherbo et al., Biochem. J., 2008, 418, 567-574), luciferase (See, e.g., deWet et al., Mol. Cell. Biol. 7:725 (1987) and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from ClonTech Laboratories, Palo Alto, Calif.), chloramphenicol acetyltransferase, beta-galactosidase, alkaline phosphatase, and horse radish peroxidase.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" or "antigenome" refers to a nucleotide sequence whose sequence of nucleotide residues is in reverse 5' to 3' orientation in relation to the sequence of nucleotide residues in a sense strand. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex.

The term "isolated" refers to a biological material, such as a virus, a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated virus, for example, is in an environment (e.g., a cell culture system, or purified from cell culture) other than the native environment of wild-type virus (e.g., the nasopharynx of an infected individual).

An "immunologically effective amount" of RSV is an amount sufficient to enhance an individual's (e.g., a human's) own immune response against a subsequent exposure to RSV. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against RSV refers to an immune response exhibited by an individual (e.g., a human) that is protective against serious lower respiratory tract disease (e.g., pneumonia and/or bronchiolitis) when the individual is subsequently exposed to and/or infected with wild-type RSV.

Recombinant Respiratory Syncytial Virus (RSV) with Codon Usage Silent Mutations in the Nonstructural Genes Live-attenuated RSV vaccine candidates have two major hurdles, suboptimal immunogenicity in infants and suboptimal stability that leads to genetic reversion towards wild-type and shedding of revertants by vaccines. The viral nonstructural (NS) proteins, NS1 and NS2, are unique and inhibit type I interferon and T cell responses. Mutating NS1/NS2 for vaccine enhances immunogenicity. However, previously developed NS1 and NS1/NS2 deletion/null mutant recombinant RSV strains are over-attenuated, and the NS2 null mutant is under-attenuated in vivo.

Figure 2:
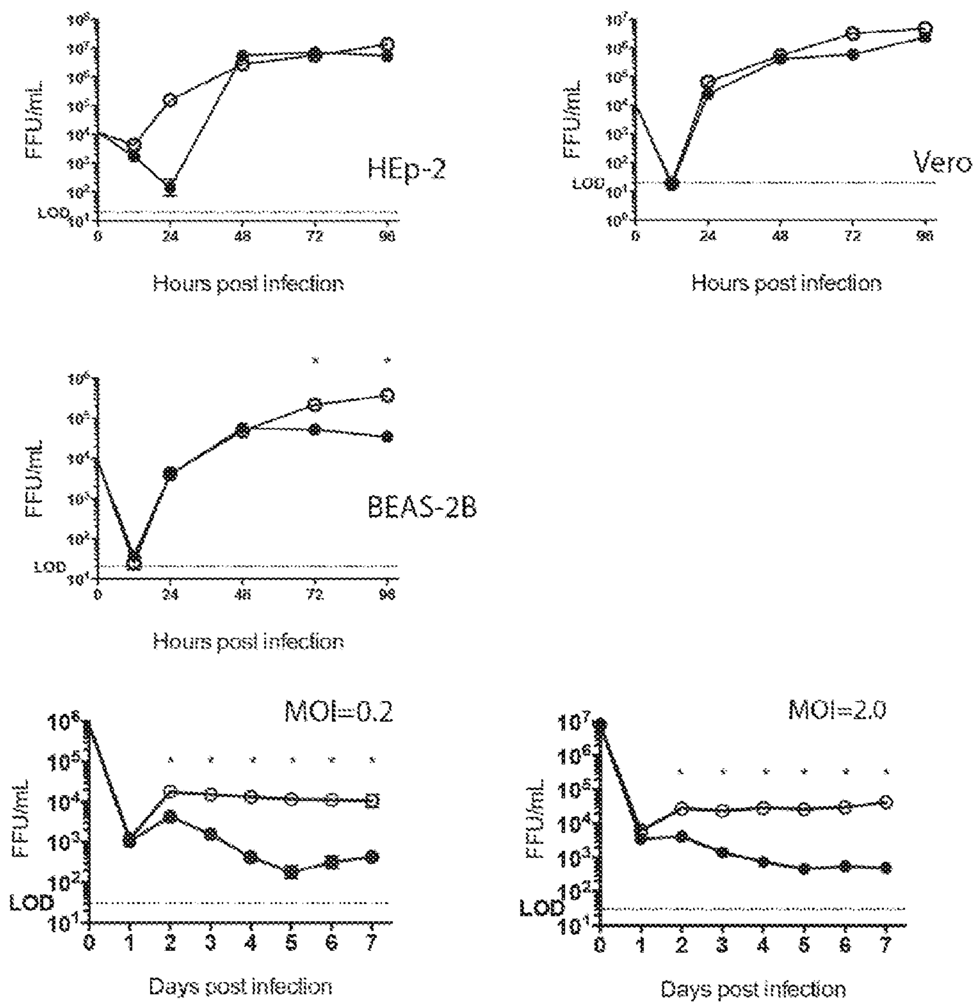
FIG. 2 shows growth data for kRSV-dNS1h in BEAS-2B (top) and Vero cell lines (bottom). Growth curves of kRSV-A2 (open circle) and kRSV-dNSh (closed circle) in HEp-2 (A), Vero (B) and BEAS-2B (C) at 37° C. infected at MOI of 0.01, as well as in differentiated NHBE/ALI cells infected at MOI of 0.2 (D) or 2.0 (E).

Mutants disclosed herein overcome the limitations of over-attenuation and instability. Mutants were generated with partial NS1 and NS2 function to bridge the attenuation-immunogenicity gap for a pediatric vaccine. Gene synthesis and the RSV BAC rescue system was used to generate NS1/NS2 mutants by altering codon usage across the NS1 and NS2 genes. Codon de-optimization reduces translation efficiency by multiple mechanisms (e.g., tRNA concentration and mRNA structure). One mutant disclosed herein ("dNSh") has 84/420 nt of NS1 mutated and 82/375 nt of NS2 mutated, reducing human codon preference without altering the amino acid sequences. This virus produces approximately 25% of wt NS1 levels, 25% of wt NS2 levels, 100% of wt nucleoprotein levels, and replicates like wt virus in Vero cells, the cell line commonly used to produce live attenuated RSV under GMP conditions (FIG. 2). In addition to reducing NS expression, this approach likely solves the genetic stability problem because there are too many mutations for reversion.

In certain embodiments, the disclosure relates to a vaccine, recombinant RSV genome, or an isolated recombinant nucleic acid encoding RSV NS1, NS2, N, P, M, G, F, M2-1, M2-2, and L genes comprising codon-deoptimization of the NS1 and NS2 genes, wherein codon-deoptimization is configured such that at least one codon to produce Gly is GGT, a codon to produce Asp is GAT, at least one codon to produce Glu is GAA, at least one codon to produce His is CAT, at least one codon to produce Ile is ATA, at least one codon to produce Lys is AAA, at least one codon to produce Leu is CTA, at least one codon to produce Asn is AAT, at least one codon to produce Gln is CAA, at least one codon to produce Val is GTA, or at least one codon to produce Tyr is TAT, wherein in greater than 25% of the Asp, Glu, His, Ile, Lys, Leu, Asn, Gln, Val, and Tyr amino acids are codon-deoptimized. In certain embodiments, greater than 75% of the amino acids are codon-deoptimized as compared to wild-type sequences, e.g., RSV A2 line 19.

In certain embodiments, the NS1 gene comprises (SEQ ID NO: 6) or variant thereof with greater than 70, 80, 90, 95, 97, 98, or 99% or more sequence identity thereto.

In certain embodiments, the NS2 gene comprises (SEQ ID NO: 9) or variant thereof with greater than 70, 80, 90, 95, 97, 98, or 99% or more sequence identity thereto.

In certain embodiments, the RSV small hydrophobic (SH) glycoprotein gene is deleted.

In certain embodiments, the nucleic acid has further codon-deoptimization of the G gene, wherein codon-deoptimization is configured such that at least one codon to produce Gly is GGT, a codon to produce Asp is GAT, at least one codon to produce Glu is GAA, at least one codon to produce His is CAT, at least one codon to produce Ile is ATA, at least one codon to produce Lys is AAA, at least one codon to produce Leu is CTA, at least one codon to produce Asn is AAT, at least one codon to produce Gln is CAA, at least one codon to produce Val is GTA, or at least one codon to produce Tyr is TAT, wherein in greater than 25% of the Asp, Glu, His, Ile, Lys, Leu, Asn, Gln, Val, and Tyr amino acids are codon-deoptimized.

In certain embodiments, the G gene comprises SEQ ID NO: 18 ATGTCGAAAAACAAAGACCAACGTACCGC-
GAAGACGTTAGAACGTACCTGGGA TACTCTAAAT-
CATTTACTATTCATATCGTCGTGC-
CTATATAAGCTAAATCTTAAA
TCGGTAGCACAAATAACACTATCCATACTGGCGA-
TAATAATCTCGACTTCGCTT ATAATAGCAGCGAT-
CATATTTATAGCCTCGGCGAACCATAAAGTCACGC-
CAACG
ACTGCGATCATACAAGATGCGACATCGCAGA-
TAAAGAATACAACGCCAACGTA CCTAAC-
CCAAAATCCTCAACTTGGTATCTCGCCCTCGAATC-
CGTCTGAAATAAC
ATCGCAAATCACGACCATACTAGCGTCAACGACAC-
CGGGAGTAAAGTCGACCC TACAATCCACGACAG-
TAAAGACGAAAAACACGACAACGACTCAAACG-
CAACCC
TCGAAGCCGACCACGAAACAACGCCAAAATAAAC-
CACCGAGCAAACCGAATAA TGATTTTCACTTT-
GAAGTATTCAATTTTGTACCCTGTAGCATATGTAG-
CAATAAT
CCAACGTGCTGGGCGATCTGTAAAAGAATAC-
CGAACAAAAAACCGGGAAAAAA AACCACGAC-
CAAACCCACGAAAAAACCAACGCTCAAAACAAC-
GAAAAAAGAT
CCCAAACCGCAAACCACGAAATCAAAAGAAGTAC-
CCACGACCAAACCCACGGA AGAGCCGAC-
CATAAACACGACCAAAACGAACATAATAACTACGC-
TACTCACGT
CCAATACCACGGGAAATCCGGAACTCACGAGT-
CAAATGGAAACGTTTCACTCG ACTTCGTC-
CGAAGGTAATCCATCGCCTTCGCAAGTCTCGA-
CAACGTCCGAATAC
CCGTCACAACCGTCATCGCCACCGAACACGC-
CACGTCAGTAG or variant thereof with greater than 70, 80, 90, 95, 97, 98, or 99% or more sequence identity thereto.

In certain embodiments, the G gene comprises SEQ ID NO: 19 ATGTCGAAAAATAAAGACCAACGTACGGC-
GAAGACGCTAGAACGTACCTGGGA TACGCTAAAT-
CATTTACTATTTATATCGTCGTGC-
CTATATAAACTAAATCTTAAA
TCGGTAGCGCAAATAACACTATCGATACTGGCGA-
TAATAATATCGACTTCGCTA ATAATAGCAGCGA-
TAATATTTATAGCCTCGGCGAATCATAAAGTCACGC-
CGACG ACTGCGATAATACAAGATGCGAC
ATCGCAAATAAAGAATACGACGCCAACGTA
TCTAACCCAAAATCCGCAACTTGGTATATCGC-
CCTCGAATCCGTCGGAAATAAC ATCGCAAATAAC-
GACCATACTAGCGTCGACGACACCGGGTG-
TAAAGTCGACGC
TACAATCCACGACGGTAAAGACGAAAAATACGA-
CAACGACGCAAACGCAACCG TCGAAACCGAC-
CACGAAACAACGTCAAAATAAACCACCGTC-
GAAACCGAATAA
TGATTTTCACTTTGAAGTATTTAATTTTGTACCCTGT-
TCGATATGTAGCAATAAT CCGACGTGCTGGGCGA-
TATGTAAAAGAATACCGAATAAAAAAC-
CGGGAAAAAA
AACGACGACCAAACCGACGAAAAAAC-
CAACGCTAAAAACAACGAAAAAAGAT CCGAAAC-
CGCAAACCACGAAATCGAAAGAAGTACCCACGAC-
GAAACCCACGG
AAGAACCGACCATAAATACGACCAAAAC-
GAATATAATAACTACGCTACTAACG TCCAATAC-
GACGGGAAATCCGGAACTAACGAGTCAAATG-
GAAACGTTTCATTC
GACTTCGTCGGAAGGTAATCCATCGCCGTCG-
CAAGTCTCGACGACTTCCGAATA TCCGTCACAAC-
CGTCGTCGC CAC CGAATACGCCACGTCAATAG or variant thereof with greater than 70, 80, 90, 95, 97, 98, or 99% or more sequence identity thereto.

In certain embodiments, the G gene comprises SEQ ID NO: 20 ATGTCGAAAAATAAAGATCAACGTACGGC-
GAAAACGCTAGAACGTACGTGGGA TACGCTAAAT-
CATCTACTATTTATATCGTCGTGTC-
TATATAAACTAAATCTAAAA
TCGGTAGCGCAAATAACGCTATCGATACTAGCGA-
TAATAATATCGACTTCGCTA ATAATAGCGGCGA-
TAATATTTATAGCGTCGGCGAATCATAAAGTAACGC-
CGAC
GACGGCGATAATACAAGATGCGACTTCG-
CAAATAAAAAATACGACGCCGACGT ATCTAACG-
CAAAATCCGCAACTAGGTATATCGCCGTCGAATC-
CGTCGGAAATAA
CGTCGCAAATAACGACGATACTAGCGTCGAC-
GACGCCGGGTGTAAAATCGACG CTACAATCGAC-
GACGGTAAAAACGAAAAATACGACGACGACG-
CAAACGCAACC GTCGAAACCGACGACGAAACAACGT-CAAAATAAACCGCCGTCGAAACCGAATA ATGATTTTCATTTTGAAGTATTTAATTTTGTACCGT-GTTCGATATGTTCGAATAA TCCGACGTGTTGGGC-GATATGTAAACGTATACCGAATAAAAAACCGGG-TAAAA AAACGACGACGAAACCGACGAAAAAAC-CGACGCTAAAAACGACGAAAAAAGA TCCGAAAC-CGCAAACGACGAAATCGAAAGAAGTACCGACGAC-GAAACCGACG GAAGAACCGACGATAAATACGACGAAAAC-GAATATAATAACGACGCTACTAAC GTCGAATAC-GACGGGTAATCCGGAACTAACGTCGCAAATG-GAAACGTTTCATTC GACtTCGTCGGAAGGTAATCCGTCGCCGTCGCAAG-TATCGACGACtTCGGAATAT CCGTCGCAAC-CGTCGTCGCCGCCGAATACGCCGCGTCAATAG or variant thereof with greater than 70, 80, 90, 95, 97, 98, or 99% or more sequence identity thereto.

In certain embodiments, F gene encodes a valine at position 557 and lysine at position 66. In certain embodiments, F gene encodes a valine at position 557 and the F gene comprises a sequence that encodes one or more of the follow amino acid sequences F gene comprises two, three, four, five or all of the follow amino acid sequences TTNIMI-TTIIIVIIVILLSLIAVGLLLYCK (SEQ ID NO: 11), ARST-PVPILKANAITTILAAVTFCFA (SEQ ID NO: 12), AVT-FCFASSQNITEEFYQST (SEQ ID NO: 13), QSTCSAVSKGYLSALRTGWYTSVITIELSNIKK (SEQ ID NO: 14), IKK NKCNGTDAKVKLMKQELDKYKNAV (SEQ ID NO: 15), and FPQAEKCKVQSNRVFC DTMYS-LTLPSEVNLCNV (SEQ ID NO: 16).

In certain embodiments, the F gene comprises two, three, four, five or all of the follow amino acid sequences (SEQ ID NO: 11), (SEQ ID NO: 12), (SEQ ID NO: 13), (SEQ ID NO: 14), (SEQ ID NO: 15), and (SEQ ID NO: 16).

In certain embodiments, the F gene encodes a valine at position 557 and the F gene encodes one or more of the follow amino acids: asparagine at position 8, phenylalanine at position 20, serine at position 35, lysine at position 66, methionine at position 79, lysine at position 124, arginine at position 191, arginine at position 213, glutamic acid at position 354, lysine at position 357, tyrosine at position 371, valine at position 384, asparagine at position at 115, and threonine at position 523.

In certain embodiments, the F gene encodes a valine at position 557 and lysine at position 66 and methionine at position 79.

In certain embodiments, the F gene encodes a valine at position 557 and lysine at position 66 and arginine at position 191.

In certain embodiments, the F gene encodes a valine at position 557, lysine at position 66, arginine at position 191, and lysine at position 357.

In certain embodiments, the F gene encodes a valine at position 557, lysine at position 66, methionine at position 79, and asparagine at position at 115.

In certain embodiments, the F gene encodes SEQ ID NO: 17 MELPILKANAITTILAAVTFCFASSQNITEEFY-QSTCSAVSKGYLSALRTGWYTSVITI ELSNIK-KNKCNGTDAKVKLMKQELDKYK-NAVTELQLLMQSTPAANNRARRELPRF MNYTLNNTKKTNVTLSKKRKRRFLGFLLGVGSA-IASGIAVSKVLHLEGEVNKIKSA LLSTNKAVVSL-SNGVSVLTSRVLDLKNYIDKQLLPIVNKQSCRISNIET-VIEFQQKNN RLLEITREFSVNAGVTTPVSTYM-LTNSELLSLINDMPITNDQKKLMSNNVQIVRQQS YSIMSIIKEEVLAYVVQLPLYGVIDTP-CWKLHTSPLCTTNTKEGSNICLTRTDRGWY CDNAGSVSFFPQAEKCKVQSNRVFCDTMYSLTLP-SEVNLCNVDIFNPKYDCKIMTS KTDVSSSVIT-SLGAIVSCYGKTKCTASNKNRGIIKTF-SNGCDYVSNKGVDTVSVGNT LYYVNKQEGKSLYVKGEPIINFYDPLVFPSDEFDA-SISQVNEKINQSLAFIRKSDELL HNVNAGKSTTNIMI-TTIIIVIIVILLSLIAVGLLLYCKARSTPVTLSKDQLS-GINNIAFSN or variants that contain one, two, three, four, five, six, seven, eight, nine, or ten amino acid substitutions provided F gene encodes a valine at position 557. In certain embodiments, the amino acid substitutions are conservative substitutions.

In certain embodiments, the disclosure relates to an isolated recombinant nucleic acid comprising an F gene encoding (SEQ ID NO: 17) or variants that contains one or two amino acid substitutions provided F gene encodes a valine at position 557 and lysine at position 66.

In certain embodiments, the F gene encodes a valine at position 557 and the F gene encodes one or more of the follow amino acids: asparagine at position 8, phenylalanine at position 20, serine at position 35, lysine at position 66, methionine at position 79, lysine at position 124, arginine at position 191, arginine at position 213, glutamic acid at position 354, lysine at position 357, tyrosine at position 371, valine at position 384, asparagine at position at 115, and threonine at position 523.

In certain embodiments, the F gene encodes a valine at position 557 and lysine at position 66.

In certain embodiments, the F gene encodes a valine at position 557 and lysine at position 66 and methionine at position 79.

In certain embodiments, the F gene encodes a valine at position 557, lysine at position 66, arginine at position 191, and lysine at position 357.

In certain embodiments, the F gene encodes a valine at position 557, lysine at position 66, methionine at position 79, and asparagine at position at 115.

In certain embodiments, the disclosure relates to a recombinant vector comprising a nucleic acid disclosed herein. In certain embodiments, the disclosure relates to a cell comprising the recombinant vector, recombinant RSV, or attenuated recombinant RSV disclosed herein.

In certain embodiments, the disclosure relates to an F gene encoding (SEQ ID NO: 17) or variants that contains one amino acid substitutions provided F gene encodes a valine at position 557.

In certain embodiments, the disclosure relates to an F gene encoding MELPILKANAITTILAAVTFCFASSQNI-TEEFYQSTCSAVSKGYLSALRTGWYTSVITI ELSNI-KENKCNGTDAKVKLMKQELDKYK-NAVTELQLLMQSTPAANNRARRELPRF MNYTLNNTKKTNVTLSKKRKRRFLGFLLGVGSA-IASGIAVSKVLHLEGEVNKIKSA LLSTNKAVVSL-SNGVSVLTSRVLDLKNYIDKQLLPIVNKQSCRISNIET-VIEFQQKNN RLLEITREFSVNAGVTTPVSTYM-LTNSELLSLINDMPITNDQKKLMSNNVQIVRQQS YSIMSIIKEEVLAYVVQLPLYGVIDTP-CWKLHTSPLCTTNTKEGSNICLTRTDRGWY CDNAGSVSFFPQAEKCKVQSNRVFCDTMYSLTLP-SEVNLCNVDIFNPKYDCKIMTS KTDVSSSVIT-SLGAIVSCYGKTKCTASNKNRGIIKTF-SNGCDYVSNKGVDTVSVGNT LYYVNKQEGKSLYVKGEPIINFYDP LVFPSDEFDA- SISQVNEKINQSLAFIRKSDELL HNVNAGKSTTNIMI-TTIIIVIIVILLSLIAVGLLLYCKARSTPVTLSKDQLS-GINNIAFSN (SEQ ID NO: 21). In certain embodiments, the F gene encodes a valine at position 557 and glutamic acid at position 66 and arginine at position 191.

In certain embodiments, the disclosure relates to recombinant polypeptides comprising an RSV F protein sequence disclosed herein. In certain embodiments, the disclosure relates to virus particles or virus like particles produced by recombinant methods comprising a RSV F protein sequence disclosed herein.

In certain embodiments, the disclosure relates to an isolated recombinant nucleic acid comprising an RSV genome OE1 of SEQ ID NO: 1 or variant with greater than 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or more sequence identity thereto.

In certain embodiments, the disclosure relates to an isolated recombinant nucleic acid comprising an RSV genome OE2 of SEQ ID NO: 2 or variant with greater than 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or more sequence identity thereto.

In certain embodiments, the disclosure relates to an isolated recombinant nucleic acid comprising an RSV genome OE3 of SEQ ID NO: 3 or variant with greater than 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or more sequence identity thereto.

In certain embodiments, the disclosure relates to an isolated recombinant nucleic acid comprising an RSV genome OE4 of SEQ ID NO: 4 or variant with greater than 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or more sequence identity thereto.

In certain embodiments, the disclosure contemplates isolated recombinant nucleic acids comprising RSV genomes OE1, OE2, OE3, and OE4, wherein one or both of the NS1 gene and NS2 gene are deleted.

Cultivating RSV in a Bacterial Artificial Chromosome

Cultivating RSV in *E. coli* bacteria may be accomplished by utilizing a bacterial artificial chromosome (BAC). A BAC is disclosed that contains the complete antigenomic sequence of respiratory syncytial virus (RSV) strain A2 except the F gene, which is the antigenomic sequence of RSV strain line 19. Along with helper plasmids, it can be used in the reverse genetics system for the recovery of infectious virus. The antigenome sequence on the plasmid can be mutated prior to virus recovery to generate viruses with desired mutations.

The plasmid is an improvement on current RSV antigenomic plasmids for several reasons. Each RSV gene is flanked by restriction endonuclease cleavage sites to allow for easy manipulation of any gene. As a basis for viral mutagenesis, this plasmid may be used to design attenuated viruses for use in vaccines. An extra gene encoding the monomeric katushka 2, mKate2, protein has been included in the antigenome prior to the first RSV gene. The mKate2 protein is a far-red fluorescent protein which would be expressed in concert with the other RSV genes and would serve as visual evidence of virus replication. Changes have also been made to the ribozyme sequences that flank the RSV antigenome and play a role in the production of infectious virus through reverse genetics.

The disclosed vectors allow for efficient mutagenesis through recombineering. This mutagenesis method requires little to no ligation cloning, but relies on the recombination machinery present in bacteria harboring certain genes from a bacteriophage. Because RSV cDNAs are often unstable in mid-to-high copy number cloning vectors within bacteria predominantly used for cloning, such as *Escherichia coli* (*E. coli*), the single digit copy nature of the bacterial artificial chromosome reduces the instability, and the reduced instability is thought to occur because the single copy nature limits the ability *E coli* to recognize crypic promoters in the RSV cDNA and produce toxic proteins.

Respiratory Syncytial Virus (RSV)

Typically, the RSV particle contains a viral genome within a helical nucleocapsid which is surrounded by matrix proteins and an envelope containing viral glycoproteins. The genome of wild-type RSV encodes the proteins, NS1, NS2, N, P, M, SH, G, F, M2-1, M2-2, and L. G, F, and SH are glycoproteins. The F gene has been incorporated into a number of viral vaccines. RSV polymerase activity consists of the large protein (L) and phosphoprotein (P). The viral M2-1 protein is used during transcription and is likely to be a component of the transcriptase complex. The viral N protein is used to encapsidate the nascent RNA.

The genome is transcribed and replicated in the cytoplasm of a host cell. Host-cell transcription typically results in synthesis of ten methylated and polyadenylated mRNAs. The antigenome is positive-sense RNA complement of the genome produced during replication, which in turn acts as a template for genome synthesis. The viral genes are flanked by conserved gene-start (GS) and gene-end (GE) sequences. At the 3' and 5' ends of the genome are leader and trailer nucleotides. The wild type leader sequence contains a promoter at the 3' end. When the viral polymerase reaches a GE signal, the polymerase polyadenylates and releases the mRNA and reinitiates RNA synthesis at the next GS signal. The L-P complex is believed to be responsible for recognition of the promoter, RNA synthesis, capping and methylation of the 5' termini of the mRNAs and polyadenylation of their 3' ends. It is believed that the polymerase sometimes dissociates from the gene at the junctions. Because the polymerase initiates transcription at the 3' end of the genome, this results in a gradient of expression, with the genes at the 3' end of the genome being transcribed more frequently than those at the 5' end.

To replicate the genome, the polymerase does not respond to the cis-acting GE and GS signals and generates positive-sense RNA complement of the genome, the antigenome. At the 3' end of the antigenome is the complement of the trailer, which contains a promoter. The polymerase uses this promoter to generate genome-sense RNA. Unlike mRNA, which is released as naked RNA, the antigenome and genome RNAs are encapsidated with virus nucleoprotein (N) as they are synthesized.

In certain embodiments, the disclosure relates to vectors and nucleic acids that contain RSV gene(s) such as the wild-type genome or antigenome. An example of an RSV antigenome is provided in U.S. Pat. No. 6,790,449, hereby incorporated by reference. Reference to RSV gene(s) and the genome is contemplated to include certain mutations, deletions, or variant combinations, such as cold-passaged (cp) and temperature sensitive (ts) derivatives of RSV, cpRSV, such as rA2cp248/404/1030ΔSH. rA2cp248/404ΔSH contains 4 independent attenuating genetic elements: cp which is based on 5 missense mutations in the N and L proteins and the F glycoprotein that together confer the non-ts attenuation phenotype of cpRSV; ts248, a missense mutation in the L protein; ts404, a nucleotide substitution in the gene-start transcription signal of the M2 gene; and ΔSH, complete deletion of the SH gene. rA2cp248/404/1030ΔSH contains 5 independent attenuating genetic elements: those present in rA2cp248/404ΔSH and ts1030, another missense mutation in the L protein. See Karron et al., J Infect Dis., 2005, 191(7): 1093-1104, hereby incorporated by reference. Within certain embodiments, it is contemplated that the RSV anitgenome may contain deletion or mutations in nonessential genes (e.g., the SH, NS1, NS2, and M2-2 genes) or combinations thereof.

Bacterial Artificial Chromosomes (BACs)

In certain embodiments, the disclosure relates to vectors and nucleic acids that contain bacterial artificial chromosomes. A bacterial cloning system for mapping and analysis of complex genomes has been disclosed in Shizuya et al., Proc. Natl. Acad. Sci., 1992, 89:8794-8797. The BAC system (for bacterial artificial chromosome) is based on *Escherichia coli* and its single-copy plasmid F factor which were described as useful for cloning large fragments of human DNA. The F factor encodes for genes that regulate its own replication including oriS, repE, parA, and parB. The oriS and repE genes mediate the unidirectional replication of the F factor while parA and parB typically maintain copy number at a level of one or two per *E. coli* genome. It is contemplated that the genes and the chromosome may contain mutations, deletions, or variants with desired functional attributes. The BAC vector (pBAC) typically contains these genes as well as a resistance marker and a cloning segment containing promoters for incorporating nucleic acid segments of interest by ligating into restriction enzyme sites. Exemplary BAC systems include those described in Shizuya & Kouros-Hehr, Keio J Med, 2001, 50(1): 26-30, hereby incorporated by reference.

One may reconstitute infectious RSV virus from the RSV BAC plasmids disclosed herein. BAC vectors can be transfected to bacteria such as *E. coli* by electroporation. The RSV-BACs disclosed herein may be stably maintained in bacteria, re-isolated from the bacteria, and inserted into a eukaryotic cell along with one or more vectors that express the N, P, L, and M2-1 proteins. These cells produce infective RSV particles. Production of infectious RSV results from co-transfection of plasmids encoding N, P, L, and M2-1 proteins and the antigenome under control of the T7 promoter into BHK-21 cells that express T7 RNA polymerase (BSR cells). See Buchholz et al., J Virol., 2000, 74(3):1187-1199, hereby incorporated by reference.

Vaccines

A number of attenuated RSV strains as candidate vaccines for intranasal administration have been developed using multiple rounds of chemical mutagenesis to introduce multiple mutations into a virus. Evaluation in rodents, chimpanzees, adults and infants indicate that certain of these candidate vaccine strains are immunogenic, and may be attenuated. Nucleotide sequence analysis of some of these attenuated viruses indicates that each level of increased attenuation is typically associated with two or more new nucleotide and amino acid substitutions.

The disclosure provides the ability to distinguish between silent incidental mutations versus those responsible for phenotype differences by introducing the mutations, separately and in various combinations, into the genome or antigenome of infectious RSV. This process identifies mutations responsible for phenotypes such as attenuation, temperature sensitivity, cold-adaptation, small plaque size, host range restriction, etc. Mutations from this menu can then be introduced in various combinations to calibrate a vaccine virus to an appropriate level of attenuation, etc., as desired. Moreover, the present disclosure provides the ability to combine mutations from different strains of virus into one strain.

The present disclosure also provides for methods of attenuation. For example, individual internal genes of RSV can be replaced with their bovine, murine or other RSV counterpart. This may include part or all of one or more of the NS1, NS2, N, P, M, SH, M2-1, M2-2 and L genes, or parts of the G and F genes. Reciprocally, means are provided to generate a live attenuated bovine RSV by inserting human attenuating genes into a bovine RSV genome or antigenome background. Human RSV bearing bovine RSV glycoproteins provides a host range restriction favorable for human vaccine preparations. Bovine RSV sequences which can be used in the present disclosure are described in, e.g., Pastey et al., J. Gen. Viol. 76:193-197 (1993); Pastey et al., Virus Res. 29:195-202 (1993); Zamora et al., J. Gen. Virol. 73:737-741 (1992); Mallipeddi et al., J. Gen. Virol. 74:2001-2004 (1993); Mallipeddi et al., J. Gen. Virol. 73:2441-2444 (1992); and Zamora et al., Virus Res. 24:115-121 (1992), each of which is incorporated herein by reference.

The disclosure also provides the ability to analyze other types of attenuating mutations and to incorporate them into infectious RSV for vaccine or other uses. For example, a tissue culture-adapted nonpathogenic strain of pneumonia virus of mice (the murine counterpart of RSV) lacks a cytoplasmic tail of the G protein (Randhawa et al., Virology 207: 240-245 (1995)). By analogy, the cytoplasmic and transmembrane domains of each of the RSV glycoproteins, F, G and SH, can be deleted or modified to achieve attenuation.

Other mutations for use in infectious RSV of the present disclosure include mutations in cis-acting signals identified during mutational analysis of RSV minigenomes. For example, insertional and deletional analysis of the leader and trailer and flanking sequences identified viral promoters and transcription signals and provided a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into the complete antigenome or genome as described herein. Other mutations involve replacement of the 3' end of genome with its counterpart from antigenome, which is associated with changes in RNA replication and transcription. In addition, the intergenic regions (Collins et al., Proc. Natl. Acad. Sci. USA 83:4594-4598 (1986), incorporated herein by reference) can be shortened or lengthened or changed in sequence content, and the naturally-occurring gene overlap (Collins et al., Proc. Natl. Acad. Sci. USA 84:5134-5138 (1987), incorporated herein by reference) can be removed or changed to a different intergenic region by the methods described herein.

In another embodiment, RSV useful in a vaccine formulation can be conveniently modified to accommodate antigenic variation in circulating virus, including antigenic subgroup A and B strains and variations within those subgroups. Typically the modification will be in the G and/or F proteins. The entire G or F gene, or the segment(s) encoding particular immunogenic regions thereof, is incorporated into the RSV genome or antigenome cDNA by replacement of the corresponding region in the infectious clone or by adding one or more copies of the gene such that several antigenic forms are represented. Progeny virus produced from the modified RSV cDNA are then used in vaccination protocols against the emerging strains. Further, inclusion of the G protein gene of RSV subgroup B would broaden the response to cover a wider spectrum of the relatively diverse subgroup A and B strains infecting human populations.

An infectious RSV clone of the disclosure can also be engineered to enhance its immunogenicity and induce a level of protection greater than that provided by natural infection, or vice versa, to identify and ablate epitopes associated with undesirable immunopathologic reactions. Enhanced immunogenicity of the vaccines produced by the present disclosure addresses one of the greatest obstacles to controlling RSV, namely the incomplete nature of immunity induced by natural infection. An additional gene may be inserted into or proximate to the RSV genome or antigenome which is under the control of an independent set of transcription signals. Genes of interest include those encoding cytokines (e.g., IL-2 through IL-15, especially IL-3, IL-6 and IL-7, etc.), gamma-interferon, and proteins rich in T helper cell epitopes. The additional protein can be expressed either as a separate protein or as a chimera engineered from a second copy of one of the RSV proteins, such as SH. This provides the ability to modify and improve the immune response against RSV both quantitatively and qualitatively.

For vaccine use, virus produced according to the present disclosure can be used directly in vaccine formulations, or lyophilized, as desired, using lyophilization protocols well known to the artisan. Lyophilized virus will typically be maintained at about 4 degrees C. When ready for use the lyophilized virus is reconstituted in a stabilizing solution, e.g., saline or comprising SPG, Mg, and HEPES, with or without adjuvant, as further described below.

Thus RSV vaccines of the disclosure contain as an active ingredient an immunogenetically effective amount of RSV produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art.

Upon immunization with a RSV composition as described herein, via aerosol, droplet, oral, topical or other route, the immune system of the host responds to the vaccine by producing antibodies specific for RSV virus proteins, e.g., F and G glycoproteins. As a result of the vaccination the host becomes at least partially or completely immune to RSV infection, or resistant to developing moderate or severe RSV infection, particularly of the lower respiratory tract.

The host to which the vaccines are administered can be any mammal which is susceptible to infection by RSV or a closely related virus and which host is capable of generating a protective immune response to the antigens of the vaccinating strain. Thus, suitable hosts include humans, non-human primates, bovine, equine, swine, ovine, caprine, lagamorph, rodents, etc. Accordingly, the disclosure provides methods for creating vaccines for a variety of human and veterinary uses.

The vaccine compositions containing the RSV of the disclosure are administered to a host susceptible to or otherwise at risk of RSV infection to enhance the host's own immune response capabilities. Such an amount is defined to be an "immunogenically effective dose." In this use, the precise amounts again depend on the host's state of health and weight, the mode of administration, the nature of the formulation. The vaccine formulations should provide a quantity of modified RSV of the disclosure sufficient to effectively protect the host patient against serious or life-threatening RSV infection.

The RSV produced in accordance with the present disclosure can be combined with viruses of the other subgroup or strains to achieve protection against multiple RSV subgroups or strains, or protective epitopes of these strains can be engineered into one virus as described herein. Typically the different viruses will be in admixture and administered simultaneously, but may also be administered separately. For example, as the F glycoproteins of the two RSV subgroups differ by only about 11% in amino acid sequence, this similarity is the basis for a cross-protective immune response as observed in animals immunized with RSV or F antigen and challenged with a heterologous strain. Thus, immunization with one strain may protect against different strains of the same or different subgroup.

In some instances it may be desirable to combine the RSV vaccines of the disclosure with vaccines which induce protective responses to other agents, particularly other childhood viruses. For example, the RSV vaccine of the present disclosure can be administered simultaneously with parainfluenza virus vaccine, such as described in Clements et al., J. Clin. Microbiol. 29:1175-1182 (1991), incorporated herein by reference. In another aspect of the disclosure the RSV can be employed as a vector for protective antigens of other respiratory tract pathogens, such as parainfluenza, by incorporating the sequences encoding those protective antigens into the RSV genome or antigenome which is used to produce infectious RSV as described herein.

Single or multiple administrations of the vaccine compositions of the disclosure can be carried out. In neonates and infants, multiple, sequential administrations may be required to elicit sufficient levels of immunity. Administration may begin within the first month of life, or before, about two months of age, typically not later than six months of age, and at intervals throughout childhood, such as at two months, six months, one year and two years, as necessary to maintain sufficient levels of protection against native (wild-type) RSV infection. Similarly, adults who are particularly susceptible to repeated or serious RSV infection, such as, for example, health care workers, day care workers, family members of young children, the elderly (over 55, 60, or 65 years), individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be advantageous for different recipient groups. For example, an engineered RSV strain expressing an additional protein rich in T cell epitopes may be particularly advantageous for adults rather than for infants.

In yet another aspect of the disclosure, RSV is employed as a vector for transient gene therapy of the respiratory tract.

According to this embodiment, the recombinant RSV genome or antigenome incorporates a sequence which is capable of encoding a gene product of interest. The gene product of interest is under control of the same or a different promoter from that which controls RSV expression. The infectious RSV produced by coexpressing the recombinant RSV genome or antigenome with the N, P, L and M2-1 proteins and containing a sequence encoding the gene product of interest is administered to a patient. Administration is typically by aerosol, nebulizer, or other topical application to the respiratory tract of the patient being treated. Recombinant RSV is administered in an amount sufficient to result in the expression of therapeutic or prophylactic levels of the desired gene product. Examples of representative gene products which are administered in this method include those which encode, for example, those particularly suitable for transient expression, e.g., interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

In certain embodiments, the disclosure relates to immunogenic compositions (e.g., vaccines) comprising an immunologically effective amount of a recombinant RSV of the invention (e.g., an attenuated live recombinant RSV or inactivated, non-replicating RSV), an immunologically effective amount of a polypeptide disclosed herein, and/or an immunologically effective amount of a nucleic acid disclosed herein.

In certain embodiments, the disclosure relates to methods for stimulating the immune system of an individual to produce a protective immune response against RSV. In the methods, an immunologically effective amount of a recombinant RSV disclosed herein, an immunologically effective amount of a polypeptide disclosed herein, and/or an immunologically effective amount of a nucleic acid disclosed herein is administered to the individual in a physiologically acceptable carrier.

Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, or combinations thereof. The preparation of such solutions ensuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, oral, topical, etc. The resulting aqueous solutions can e.g., be packaged for use as is or lyophilized, the lyophilized preparation being combined with a sterile solution prior to administration.

In certain embodiments, the RSV (or RSV components) is administered in a quantity sufficient to stimulate an immune response specific for one or more strains of RSV (e.g., an immunologically effective amount of RSV or an RSV component is administered). Preferably, administration of RSV elicits a protective immune response. Dosages and methods for eliciting a protective anti-viral immune response, adaptable to producing a protective immune response against RSV, are known to those of skill in the art. See, e.g., U.S. Pat. No. 5,922,326; Wright et al. (1982) Infect. Immun. 37:397-400; Kim et al. (1973) Pediatrics 52:56-63; and Wright et al. (1976) J. Pediatr. 88:931-936. For example, virus can be provided in the range of about $10^3$-$10^6$ pfu (plaque forming units) per dose administered (e.g., $10^4$-$10^5$ pfu per dose administered). Typically, the dose will be adjusted based on, e.g., age, physical condition, body weight, sex, diet, mode and time of administration, and other clinical factors. The prophylactic vaccine formulation can be systemically administered, e.g., by subcutaneous or intramuscular injection using a needle and syringe or a needleless injection device. Preferably, the vaccine formulation is administered intranasally, e.g., by drops, aerosol (e.g., large particle aerosol (greater than about 10 microns)), or spray into the upper respiratory tract. While any of the above routes of delivery results in a protective systemic immune response, intranasal administration confers the added benefit of eliciting mucosal immunity at the site of entry of the virus. For intranasal administration, attenuated live virus vaccines are often preferred, e.g., an attenuated, cold adapted and/or temperature sensitive recombinant RSV, e.g., a chimeric recombinant RSV. As an alternative or in addition to attenuated live virus vaccines, killed virus vaccines, nucleic acid vaccines, and/or polypeptide subunit vaccines, for example, can be used, as suggested by Walsh et al. (1987) J. Infect. Dis. 155:1198-1204 and Murphy et al. (1990) Vaccine 8:497-502.

In certain embodiments, the attenuated recombinant RSV is as used in a vaccine and is sufficiently attenuated such that symptoms of infection, or at least symptoms of serious infection, will not occur in most individuals immunized (or otherwise infected) with the attenuated RSV—in embodiments in which viral components (e.g., the nucleic acids or polypeptides herein) are used as vaccine or immunogenic components. However, virulence is typically sufficiently abrogated such that mild or severe lower respiratory tract infections do not typically occur in the vaccinated or incidental host.

While stimulation of a protective immune response with a single dose is preferred, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type RSV infection. Similarly, adults who are particularly susceptible to repeated or serious RSV infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of virus-neutralizing secretory and serum antibodies, and dosages adjusted or vaccinations repeated as necessary to elicit and maintain desired levels of protection.

Alternatively, an immune response can be stimulated by ex vivo or in vivo targeting of dendritic cells with virus. For example, proliferating dendritic cells are exposed to viruses in a sufficient amount and for a sufficient period of time to permit capture of the RSV antigens by the dendritic cells. The cells are then transferred into a subject to be vaccinated by standard intravenous transplantation methods.

Optionally, the formulation for prophylactic administration of the RSV also contains one or more adjuvants for enhancing the immune response to the RSV antigens. Suitable adjuvants include, for example: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvant QS-21.

If desired, prophylactic vaccine administration of RSV can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the RSV, or can be administered separately. Either the protein or an expression vector encoding the protein can be administered to produce an immunostimulatory effect.

Although vaccination of an individual with an attenuated RSV of a particular strain of a particular subgroup can induce cross-protection against RSV of different strains and/or subgroups, cross-protection can be enhanced, if desired, by vaccinating the individual with attenuated RSV from at least two strains, e.g., each of which represents a different subgroup. Similarly, the attenuated RSV vaccines can optionally be combined with vaccines that induce protective immune responses against other infectious agents.

EXPERIMENTAL

The A2-line19F-I557V Virus is Immunogenic in BALB/c Mice

This is demonstrated in FIG. 7, which shows that this virus induces higher levels of RSV-neutralizing serum antibodies than RSV A2 and RSV A2-line19F. FIG. 7B demonstrates that, even low input doses, this virus provide complete protection to challenge with a heterologous strain of RSV, when challenged 29 days post-primary infection. This complete protection with low dose immunization is not seen for two other strains of RSV, A2-K-line19F and A2-K-A2GF, which allow for breakthrough reinfection. Those two viruses are similar to A2-line19F-I557V except for the F protein, indicating that the I557V F protein encoded by this virus is important for the phenotype.

In addition to being immunogenic (FIG. 7A), the A2-line19F-I557V virus is thermostable. Thermostability of the virus was measured as the ability of the virus to retain titer over multiple days when incubated at either 4° C. or 37° C. The results indicated indicate that this virus is more thermostable than the A2-K-A2GF virus at both temperatures tested and more stable than A2-line19F at 4° C. As stated above, the F gene is the only difference between these two viruses, indicating this unique F protein is responsible for the phenotype.

The A2-line 19 F RSV strain is more stable than the A2 strain, and Val at 557 in the context of the line 19 F protein makes the virus even more stable. Val at position 557 in other strains is also likely stabilizing—557 position and stability. In certain embodiments, the disclosure contemplates other mutations at position 557 (any amino acid, e.g., alanine, valine, isoleucine, leucine), in any F strain context, that affect thermostability of the virus.

Generation of Recombinant RSV with NS1 and NS2 Codon Silent Mutations and Growth Attenuation Codons that are uncommon in humans were used to prepare recombinant RSV with the NS1 and NS2 genes designated dNS1h and dNS2h below. Codons that are uncommon in RSV were used to prepare recombinant RSV with the NS1 and NS2 genes designated dNS1 v and dNS2v below. FIG. 1 provides a table used to determine optimal sequences. Recombinant RSV was prepared with the following nucleotide sequences for the NS1 and NS2 gene. It is important to note that prior to testing codons, it was unpredictable if either the uncommon human codons or uncommon RSV codons would produce a desirable RSV vaccine candidate. Experiments using codons uncommon for RSV sequences had the unanticipated and undesirable effect of increased expression. Using codons uncommon for human sequences had the desirable effect of decreased expression. Experiments comparing NS codons uncommon for human sequences and NS codons uncommon for RSV sequences indicated that the codons uncommon for human sequences were preferential for vaccine development.

dNS1h nucleotide sequence (SEQ ID NO: 6) has which as 84 out of 420 nucleotides (20%) different and 68 out of 140 codons (48%) than NS1 in wild-type A2

SEQ ID NO: 6

ATGGGTTCGAATTCGCTATCGATGATAAAAGTACGTCTACAAAATCTATT

TGATAATGATGAAGTAGCGCTACTAAAAATAACGTGTTATACGGATAAAC

TAATACATCTAACGAATGCGCTAGCGAAAGCGGTAATACATACGATAAAA

CTAAATGGTATAGTATTTGTACATGTAATAACGTCGTCGGATATATGTCC

GAATAATAATATAGTAGTAAAATCGAATTTTACGACGATGCCGGTACTAC

AAAATGGTGGTTATATATGGGAAATGATGGAACTAACGCATTGTTCGCAA

CCGAATGGTCTACTAGATGATAATTGTGAAATAAAATTTTCGAAAAAACT

ATCGGATTCGACGATGACGAATTATATGAATCAACTATCGGAACTACTAG

GTTTTGATCTAAATCCGTAA dNS1v nucleotide sequence (SEQ ID NO: 7) has which as 145 out of 420 nucleotides (34%) different and 122 out of 140 codons (87%) than NS1 in wild-type A2

SEQ ID NO: 7

ATGGGGTCGAACTCGCTCTCGATGATCAAGGTCCGCCTCCAGAATCTCTT

CGACAACGACGAGGTCGCGCTCCTCAAGATCACGTGTTACACGGACAAGC

TCATCCACCTCACGAACGCGCTCGCGAAGGCGGTCATCCACACGATCAAG

CTCAACGGGATCGTCTTCGTCCACGTCATCACGTCGTCGGACATCTGTCC

GAACAACAACATCGTCGTCAAGTCGAACTTCACGACGATGCCGGTCCTCC

AGAACGGGGGGTACATCTGGGAGATGATGGAGCTCACGCACTGTTCGCAG

CCGAACGGGCTCCTCGACGACAACTGTGAGATCAAGTTCTCGAAGAAGCT

CTCGGACTCGACGATGACGAACTACATGAACCAGCTCTCGGAGCTCCTCG

GGTTCGACCTCAACCCGTAA dNS2h nucleotide sequence (SEQ ID NO: 9) has which as 82 out of 420 nucleotides (21%) different and 73 out of 140 codons (58%) than NS1 in wild-type A2

SEQ ID NO: 9

ATGGATACGACGCATAATGATAATACGCCGCAACGTCTAATGATAACGGA

TATGCGTCCGCTATCGCTAGAAACGATAATAACGTCGCTAACGCGTGATA

-continued

```
TAATAACGCATAAATTTATATATCTAATAAATCATGAATGTATAGTACGT

AAACTAGATGAACGTCAAGCGACGTTTACGTTTCTAGTAAATTATGAAAT

GAAACTACTACATAAAGTAGGTTCGACGAAATATAAAAAATATACGGAAT

ATAATACGAAATATGGTACGTTTCCGATGCCGATATTTATAAATCATGAT

GGTTTTCTAGAATGTATAGGTATAAAACCGACGAAACATACGCCGATAAT

ATATAAATATGATCTAAATCCGTAA
```

dNS2v nucleotide sequence (SEQ ID NO: 10) has which as 103 out of 420 nucleotides (27%) different and 92 out of 140 codons (73%) than NS1 in wild-type A2

SEQ ID NO: 10

```
ATGGACACGACGCACAACGACAACACGCCGCAGCGCCTCATGATCACGGA

CATGCGCCCGCTCTCGCTCGAGACGATCATCACGTCGCTCACGCGCGACA

TCATCACGCACAAGTTCATCTACCTCATCAACCACGAGTGTATCGTCCGC

AAGCTCGACGAGCGCCAGGCGACGTTCACGTTCCTCGTCAACTACGAGAT

GAAGCTCCTCCACAAGGTCGGGTCGACGAAGTACAAGAAGTACACGGAGT

ACAACACGAAGTACGGGACGTTCCCGATGCCGATCTTCATCAACCACGAC

GGGTTCCTCGAGTGTATCGGGATCAAGCCGACGAAGCACACGCCGATCAT

CTACAAGTACGACCTCAACCCGTAA
```

BEAS-2B cell lines at 60-70% confluence are infected with the recombinant virus indicated as above at MOI (multiplicity of infection) of 0.01 (i.e., for each 100 cells, there is one infectious virus particle). This is done by first counting the cells before infection, calculating the total number of cells in each well, then calculating the amount of each virus for infection. Infection is done at room temperature for 1 hour, then washed off. The infected cells are left in 37° C. incubator with 5% $CO_2$ for up to 96 hours. Samples are taken at 12, 24, 48, 72, and 96 hours after infection and frozen. After collecting all the time point samples, the amount of virus in each sample is determined by titering on Vero cell lines according to standard protocol and the titer (FFU/mL, meaning Fluorescent Focus-forming Unit per mL) is calculated for each sample. Since viruses used have a red fluorescent gene in the genome, the infected cells are counted under the fluorescent microscope providing fluorescent focus-forming units. Each data point represents duplicate samples from two independent experiments.

As illustrated in FIG. 2, growth of kRSV-dNS1h (human deoptimized NS1+NS2 virus) is attenuated in the BEAS-2B cell line at 72 and 96 hours post infection. It is believed that this is due to lower NS1 and NS2 proteins than wild type virus.

Expression of RSV in Plasmid Designed for Low Copy Number

Infectious recombinant RSV (rRSV) can be recovered from transfected plasmids. Co-expression of RSV N, P, L, and M2 1 proteins as well as the full-length antigenomic RNA is sufficient for RSV replication. Infectious RSV may be produced from the co-transfection of plasmids encoding N, P, L, and M2-1 proteins and the antigenomic cDNA under control of the T7 promoter into BHK-21 cells that stably express T7 RNA polymerase (BSR cells). Currently research labs typically use a RSV antigenomic cDNA cloned in the plasmid pBR322 (mid-range copy number, 15-20 copies per *E coli*). In order to maintain the antigenomic cDNA in this plasmid, the bacteria is grown at 30° C. and low aeration. Nevertheless, plasmid rearrangements and clone loss is frequently experienced.

A fraction of RSV cDNA containing the attachment glycoprotein (G) and fusion (F) genes of the virus was found to be unclonable in pUC-based plasmids (500-700 plasmid copies in *E coli*). This fragment was cloned in a low copy number (approximately 5 copies per *E. coli*) plasmid called pLG338-30.5. The plasmid pLG338-30 was developed to increase the stability of cloned lentivirus glycoproteins. Cunningham et al., Gene, 1993, 124, 93-98. It is hypothesized that cDNA instability in *E coli* results from the presence of cryptic *E coli* transcription promoters within viral glycoprotein sequences. Thus, instability of cDNA in "promoterless" plasmids in bacteria can arise because aberrant proteins are expressed from cryptic promoters, leading to toxicity exacerbated by plasmid copy number.

An antigenomic plasmid was generated containing the RSV strain A2 genome with the strain line 19 F gene in place of the A2 F gene. It had been derived from the antigenome plasmid first disclosed in Collins et al., Proc Natl Acad Sci USA., 1995, 92(25):11563-11567 and U.S. Pat. No. 6,790,449 hereby incorporated by reference. The antigenome was digested out of the plasmid vector and ligated into the pKBS3 BAC.

GalK recombineering reagents were obtained from the NCI and successfully established a BAC-RSV reverse genetics protocol (FIGS. 4 and 5). See http://web.ncifcrf.gov/research/brb/recombineeringInformation.aspx, hereby incorporated by reference. Mutation of RSV cDNA via BAC recombineering has enhanced the ability to manipulate RSV for generation of mutants. An added benefit of the system is enhanced stability of the full-length antigenomic cDNA in the BAC vector.

The BAC-based RSV antigenome vector was propagated at 32° C. and 250 RPM without observing any vector rearrangements or clone loss in *E coli*. Thus, BAC-RSV not only enables manipulations via recombineering but also facilitates RSV reverse genetics in general owing to elimination of cDNA instability.

RSV Antigenome in BAC Vector (pSynkRSV_Line 19 F Construction)

The RSV-BAC pSynkRSV_line 19 F contains the modified katushka gene (mKate2, fluorescent protein), and restriction sites for convenient standard cloning methods. To build pSynkRSV, three nucleic acid pieces were synthesized by Gene Art, a company that synthesizes DNA. These three pieces then have to be put together in the bacterial artificial chromosome (BAC). The three pieces are designated pSynkRSV-BstBI_SacI (#1), pSynkRSV-SacI_ClaI (#2), and pSynkRSV-ClaI_MluI (#3). One uses the plasmid pKBS3 as the backbone for constructing pSynkRSV. See FIGS. 6A-E. pSynkRSV contains the bacterial artificial chromosome sequences needed to regulate copy number and partitioning in the bacteria.

To insert the three synthesized segments, one puts oligonucleotide adapters into pKBS3 between two existing restriction enzyme cut sites, BstBI and MluI.

The overhangs were designed such that the adapter would ligate into pKBS3 at the BstBI and MluI sites. Underlined sequences indicate restriction sites: SacI, ClaI, and AvrII from right to left respectively. This produces a multi-cloning site containing the restriction sites BstBI, SacI, ClaI, AvrII, and MluI, in that order, and a plasmid termed pKBS5. See FIG. 6A. One cuts and ligates the SacI_ClaI segment (#2) from Gene Art into pKBS5. See FIG. 6B. The next one cuts and ligates the #3 segment using the enzymes AvrII and MluI (cannot use ClaI again due to an inactive ClaI restriction site in pSynkRSV-ClaI_MluI). See FIG. 6C. At this point, the plasmid pKBS5 contains the Gene Art sequences from SacI to ClaI, some intervening nucleotides (less than 10), and the Gene Art sequences from AvrII to MluI. One cuts and ligates the #1 segment using BstBI and SacI. See FIG. 6D. This RSV BAC contains about 10 unwanted nucleotides between two ClaI sites (that from segment #2 and segment #3). Recombineering is used to delete those nucleotides, thus generating pSynkRSV_line 19 F. See FIG. 6E. The three segments should be ligated in this order to avoid potential interference from multiple restriction sites.

Recombinant Respiratory Syncytial Virus (RSV) as Live-Attenuated Vaccine (LAV)

Four expression plasmids were generated, one that expresses RSV nucleoprotein (N), one that expresses RSV phosphoprotein (P), one that expresses RSV matrix 2 ORF 1 protein (M2-1), and one that expresses RSV large polymerase (L)-pA2-Nopt, pA2-Popt, pA2-M2-lopt, and pA2-Lopt. The nomenclature reflects the fact that these genes are of the A2 strain of RSV and that these cDNAs are optimized for human codon bias in order to increase expression levels in mammalian cells. Recovery of recombinant RSV from cDNA includes five components: full length RNA (e.g. provided by pSynk-RSV119F), and RSV N, P, M2-1, and L proteins. The four helpers plasmids pA2-Nopt, pA2-Popt, pA2-M2-lopt, and pA2-Lopt useful for driving RSV rescue.

A recombinant respiratory syncytial virus strain A2-line19F was generated with a point mutation at residue F557, at which the isoleucine was changed to a valine (virus name: A2-line19F-I557V). A protein expression plasmid was also generated which encodes the line 19 F protein with the same isoleucine to valine mutation at position 557 (protein name-line 19F-I557V). A2-line19F-I557V has higher thermostability, at 4° C. and 37° C., than the A2-line 19F parent virus. This increased stability likely contributes to an increased induction of neutralizing antibodies and protection by A2-line19F-I557V relative to A2-line 19F.

Development of a live-attenuated RSV vaccine has been hindered by low RSV immunogenicity in young infants, which constitute the target population, and limited genomic stability. A desirable vaccine is immunogenic and genetically and thermally stable and safe for vaccination in young infants.

RSV nonstructural (NS) proteins 1 and 2 (NS1 and NS2) are associated with inhibition of host cell interferon pathways and thus potentially limiting the immunogenicity of the virus. The small hydrophobic (SH) glycoprotein forms cationic pores in membranes, modulates the host apoptotic pathways and inhibits tumor necrosis factor-a (TNF-a) signaling. SH, NS1 and NS2 are dispensable for virus replication. However, deletion of NS1 and NS2 together results in an over-attenuation. Deletion of the SH protein has little apparent effect on attenuation in experimental vaccine candidates currently being evaluated. However, deletion of SH enhances RSV replication in vitro and presumably enhances expression of downstream genes, such as the antigenic G and F genes.

RSV vaccine candidates disclosed herein combine multiple technologies to overcome the challenges of poor immunogenicity and limited genetic and thermal stability in a safe viral vaccine candidate. RSV LAV OE1 combines limited expression of immune inhibitory proteins NS1 and NS2 through codon-deoptimization and SH protein through deletion without the potential for rapid reversion in a stable and immunogenic viral background.

Vaccine candidates were generated using BAC-based RSV reverse genetics codon-deoptimization of nonstructural (NS) genes NS1 and NS2 were combined with the A2-line 19F gene containing a mutation at residue 557, as well as deletion of the RSV small hydrophobic (SH) glycoprotein.

OE1 Virus Genome (SEQ ID NO: 1)

RSV vaccine candidate genotype:

A2-mKate2-dNSh-deltaSH-A2G-line19F-I557V (tagged)

and A2-dNSh-deltaSH-A2G-line19F-I557V (untagged)

RSV attachment glycoprotein (G) is a heavily glycosylated protein, which exists in two variant forms: membrane-bound and secreted. Studies evaluating the functional role of RSV G have shown that it plays a role in inhibition of toll-like receptor activation and its secreted form likely acts as an immune antigen decoy. In addition to RSV F, G protein is also immunogenic, however due in part to its extensive glycosylation, it is a poor antigen for generation of neutralizing antibodies. RSV G is indispensible for virus replication, but deletion results in over-attenuation. Thus, G can be considered a non-essential virulence gene.

An RSV A2 G protein sequence was substituted which contains a M48I mutation and has 50% of the codons deoptimized [dGm(50%)] into the background of the RSV LAV OE1 virus genome. The OE2 virus background includes codon-deoptimization of nonstructural (NS) genes NS1 and NS2 with the A2-line 19F gene containing a mutation at amino acid residue 557, as well as deletion of the RSV small hydrophobic (SH) glycoprotein.

OE2 Virus Genome (SEQ ID NO: 2)

RSV vaccine candidate genotype:

A2-mKate2-dNSh-deltaSH-dGm(50%)-line19F-I557V (tagged)

and A2-dNSh-deltaSH-dGm(50%)-line19F-I557V (untagged)

RSV LAV OE2 combines reduced expression of immune inhibitory glycoprotein G through codon-deoptimization of 50% of codons, 100% codondeoptimization of immunomodulatory proteins NS1 and NS2, and deletion of SH protein without the potential for rapid reversion in a stable and immunogenic viral background.

In a third vaccine candidate, an RSV A2 G protein sequence substituted with one which contains a M48I mutation and has 75% of the codons deoptimized [dGm(75%)] into the background of the RSV LAV OE1 virus genome. The OE3 virus background includes codon-deoptimization of nonstructural (NS) genes NS1 and NS2 with the A2-line 19F gene containing a mutation at residue 557, as well as deletion of the RSV small hydrophobic (SH) glycoprotein.

OE3 Virus Genome (SEQ ID NO: 3)

RSV vaccine candidate genotype:

A2-mKate2-dNSh-deltaSH-dGm(75%)-line19F-I557V (tagged)

and A2-dNSh-deltaSH-dGm(75%)-line19F-I557V (untagged)

RSV LAV OE3 combines reduced expression of immune inhibitory glycoprotein G through codon-deoptimization of 75% of codons, 100% codon deoptimization of immunomodulatory proteins NS1 and NS2, and deletion of SH protein without the potential for rapid reversion in a stable and immunogenic viral background.

An RSV A2 G protein sequence which contains a M48I mutation and has 100% of the codons deoptimized [dGm (100%)] into the background of the RSV LAV OE1 virus genome was generated. The OE4 virus background includes codon-deoptimization of nonstructural (NS) genes NS1 and NS2 with the A2-line 19F gene containing a mutation at residue 557, as well as deletion of the RSV small hydrophobic (SH) glycoprotein.

OE4 Virus Genome (SEQ ID NO: 4)
RSV vaccine candidate genotype:
A2-mKate2-dNSh-deltaSH-dGm(100%)-line19F-I557V (tagged)
and A2-dNSh-deltaSH-dGm(100%)-line19F-I557V (untagged)

What is claimed is:

1. An isolated recombinant nucleic acid comprising a NS1 gene of the RSV genome, wherein the NS1 gene has at least 90% sequence identity to SEQ ID NO: 6.

2. A recombinant vector comprising a nucleic acid of claim 1.

3. A recombinant RSV comprising the nucleic acid of claim 1.

4. A recombinant RSV comprising a nucleic acid of claim 1 and further comprising a NS2 gene having at least 90% identity with SEQ ID NO 9.

5. The isolated recombinant nucleic acid of claim 1, wherein the NS1 gene comprises SEQ ID NO 6.

6. The recombinant RSV of claim 3, comprising SEQ ID NO:6 and SEQ ID NO 9.

7. A recombinant RSV genome comprising: a NS1 gene comprising SEQ ID NO. 6, a codon deoptimized G gene, and wherein the small hydrophobic glycoprotein gene is not present in the RSV genome.

8. The recombinant RSV genome of claim 7 further comprising a NS2 gene comprising SEQ ID NO 9.

9. A recombinant RSV genome comprising: a NS1 gene comprising SEQ ID NO. 6, a NS2 gene comprising SEQ ID NO 9, a codon deoptimized G gene, and wherein the small hydrophobic glycoprotein gene is not present.

10. An expression system comprising an attenuated recombinant RSV of claim 3.

11. An expression system comprising an attenuated recombinant RSV of claim 6.

12. A vaccine comprising a recombinant RSV of claim 3.

13. A vaccine comprising the recombinant RSV genome of claim 7.

14. A vaccine comprising the recombinant RSV of claim 9.

* * * * *